US010508266B2

(12) United States Patent
González Biosca et al.

(10) Patent No.: US 10,508,266 B2
(45) Date of Patent: Dec. 17, 2019

(54) METHOD FOR THE PREVENTION AND/OR THE BIOLOGICAL CONTROL OF BACTERIAL WILT CAUSED BY *RALSTONIA SOLANACEARUM*, VIA THE USE OF BACTERIOPHAGES SUITABLE FOR THIS PURPOSE AND COMPOSITIONS THEREOF

(71) Applicants: UNIVERSITAT DE VALÈNCIA (ESTUDI GENERAL), Valencia (ES); INSTITUTO VALENCIANO DE INVESTIGACIONES AGRARIAS (IVIA), Moncada Valencia (ES)

(72) Inventors: Elena González Biosca, Valencia (ES); María Milagros López González, Valencia (ES); María Belén Álvarez Ortega, Valencia (ES)

(73) Assignees: UNIVERSITAT DE VALÈNCIA (ESTUDI GENERAL), Valencia (ES); INSTITUTO VALENCIANO DE INVESTIGACIONES AGRARIAS (IVIA), Moncada Valencia (ES)

( * ) Notice: Subject to any disclaimer, the term of this patent is extended or adjusted under 35 U.S.C. 154(b) by 0 days.

(21) Appl. No.: 15/576,798

(22) PCT Filed: May 24, 2016

(86) PCT No.: PCT/ES2016/070392
§ 371 (c)(1),
(2) Date: Nov. 24, 2017

(87) PCT Pub. No.: WO2016/189180
PCT Pub. Date: Dec. 1, 2016

(65) Prior Publication Data
US 2018/0312814 A1 Nov. 1, 2018

(30) Foreign Application Priority Data
May 26, 2015 (ES) .................................. 201530730

(51) Int. Cl.
*C12N 7/00* (2006.01)
*A01N 63/00* (2006.01)
(Continued)

(52) U.S. Cl.
CPC ................. *C12N 7/00* (2013.01); *A01M 7/00* (2013.01); *A01N 63/00* (2013.01); *A01G 25/02* (2013.01);
(Continued)

(58) Field of Classification Search
None
See application file for complete search history.

(56) References Cited

FOREIGN PATENT DOCUMENTS

| JP | 2005-278513 A | 10/2005 |
|----|---------------|---------|
| JP | 2007-252351 A | 10/2007 |
| KR | 20120055801 A | 6/2012 |

OTHER PUBLICATIONS

International Search Report for PCT/ES2016/070392, dated Jul. 27, 2016.
(Continued)

*Primary Examiner* — Michelle S Horning
(74) *Attorney, Agent, or Firm* — Merchant & Gould P.C.; Daniel R. Evans

(57) ABSTRACT

A method is for prevention and/or biological control of wilt caused by *Ralstonia solanacearum*, by use of suitable bacteriophages. In addition a method uses the structural characterisation, genome sequence and activity of three specific lytic bacteriophages of *R. solanacearum*. Podovirus presents an elevated stability between 4° C. and 30° C. in an aqueous medium in the absence of a host. As a result of the high level of stability, lytic activity, elevated specificity towards *R. solanacearum* and the absence of activity against the microbiota associated with the plants to be protected, bacteriophages are used for the biological control of *R. solan-*
(Continued)

*acearum* in river courses and irrigation water, as well as in a method for preventing and/or controlling the wilt produced by the bacteria, in which at least one of the bacteriophages, or combinations thereof, are delivered to the plants and/or the soil in the irrigation water.

22 Claims, 7 Drawing Sheets

Specification includes a Sequence Listing.

(51) Int. Cl.
*A01M 7/00* (2006.01)
*A01G 25/02* (2006.01)
*A01G 25/06* (2006.01)
*A01G 27/00* (2006.01)
*A01G 31/00* (2018.01)

(52) U.S. Cl.
CPC .............. *A01G 25/06* (2013.01); *A01G 27/00* (2013.01); *A01G 31/00* (2013.01); *C12N 2795/10221* (2013.01); *C12N 2795/10231* (2013.01)

(56) References Cited

OTHER PUBLICATIONS

Young et al., "Biocontrol Potential of a Lytic Bacteriophage PE204 against Bacterial Wilt of Tomato", Journal of Microbiology and Biotechnology, 22(12): 1613-1620 (2012).

```
SEQ ID NO:1  TCCAGAACTTCGCCATGATCCACGACTCCTTCGGGACCACCGCGGGTGACGTGGAGGAGA  8081
SEQ ID NO:3  TCCAGAACTTCGCCATGATCCACGACTCCTTCGGGACCACCGCGGGTGACGTGGAGGAGA  8080
SEQ ID NO:2  TCCAGAACTTCGCCATGATCCACGACTCCTTCGGGACCACCGCGGGTGACGTGGAGGAGA  8159
             ************************************************************

SEQ ID NO:1  TGTATCGGGTGGTCCGCGAGAGCTTCGTGGAGATGTACTCCGAGGTGCGCGTCCTGGAAG  8141
SEQ ID NO:3  TGTATCGGGTGGTCCGCGGGAGCTTCGTGGAGATGTACTCCGAGGTGCGCGTCCTGGAAG  8140
SEQ ID NO:2  TGTATCGGGTGGTCCGCGAGAGCTTCGTGGAGATGTACTCCGAGGTGCGCGTCCTGGAAG  8219
             ******************  ****************************************

SEQ ID NO:1  ACTTCCGGGATGAGATCGCGGAGCAACTTTCGAGAAGGCCCAAGCGAAGATGCCGCCGC   8201
SEQ ID NO:3  ACTTCCGGGATGAGATCGCGGAGCAACTTTCGAGAAGGCCCAAGCGAAGATGCCGCCGC   8200
SEQ ID NO:2  ACTTCCGGGATGAGATCGCGGAGCAACTTTCGAGAAGGCCAGGGCCAAGATGCCTGATC   8279
             ****************************************  ** *******    *

SEQ ID NO:1  TACCCGAGCGCGGTCTCCTGGAGTTGTCTCGCGTCTGCGAGAGCCGCTATTGCTTTGC--  8259
SEQ ID NO:3  TACCCGAGCGCGGTCTCCTGGAGTTGTCTCGCGTCTGCGAGAGCCGCTATTGCTTTGC--  8258
SEQ ID NO:2  TACCGGCCCGCGGCCTCCTGGAGTTGTCTCGTGTGTGCGAGAGCCGGTACTGTTTTGCGT  8339
             ****  *  *****  *************** ** ********** ** ** *****

SEQ ID NO:1  ------------------------------------------------------------
SEQ ID NO:3  ------------------------------------------------------------
SEQ ID NO:2  AGACTGTTTCACATTTGCAACTATTCCTTATGAGTGAGTGTAAGAAGTGCGGGGTTGCCT  8399

SEQ ID NO:1  ------------------------------------------------------------
SEQ ID NO:3  ------------------------------------------------------------
SEQ ID NO:2  TGGTGCCAGGTGAGAACTGGTATCCGTCCCTCGCAAAGAAGAACAACCAGGTGTGTAAGC  8459

SEQ ID NO:1  ------------------------------------------------------------
SEQ ID NO:3  ------------------------------------------------------------
SEQ ID NO:2  GGTGTCACACGGCACGGAGCGAGGCGAAGCGGATTGAAGACCGCGAGACCAACCTCCCGA  8519

SEQ ID NO:1  ------------------------------------------------------------
SEQ ID NO:3  ------------------------------------------------------------
SEQ ID NO:2  AGTGGATGCTGCGAAACGCCAGGAATCGGGCCAAGGCACAGGGACTCCCATTCGACCTGG  8579

SEQ ID NO:1  ------------------------------------------------------------
SEQ ID NO:3  ------------------------------------------------------------
SEQ ID NO:2  AGGAGTCGGACATCCAAATTCCGCTCCTCTGTCCCGTGCTGGGCATCCCGCTGGAAGTCT  8639

SEQ ID NO:1  ------------------------------------------------------------
SEQ ID NO:3  ------------------------------------------------------------
SEQ ID NO:2  CACGCGGGCACTTCACGGACAACTCCCCGGCTCTGGACAAGTTCATCCCGGAGCTTGGGT  8699

SEQ ID NO:1  ------------------------------------------------------------
SEQ ID NO:3  ------------------------------------------------------------
SEQ ID NO:2  ACGTGAAGGGCAACGTGGCCGTCATTTCTCAGAAGGCCAACGTGATGAAGTCCAACGCCA  8759

SEQ ID NO:1  ------------------------------------------------CTGAACCCTTCCAC  8273
SEQ ID NO:3  ------------------------------------------------CTGAACCCTTCCAC  8272
SEQ ID NO:2  CCATTCAGGAGGTGGAGGCACTGGCCGCGTGGATGCGTAGTCGCGCCTGAACCCCTCCAC  8819
                                                             ********  *****

SEQ ID NO:1  ATCTGGAAGAGTTGAGCCGGGGGAACGATTAGGTGCCACACATGGATAAACCAGCCGCCG  8333
SEQ ID NO:3  ATCTGGAAGAGTTGAGCCGGGGGAACGATTAGGTGCCACACATGGATAAACCAGCCGCCG  8332
SEQ ID NO:2  ATCTGGAAGAGTTGAGCCGGGGGAACGATTAGGTGCCACACATGGATAAACCAGCCGCCG  8879
             ************************************************************

SEQ ID NO:1  TTCCCCCGGTGGCCTCTCCCGAGACAACCGATGGAACGCAACGAACACGAAGTATCGGAC  8393
SEQ ID NO:3  TTCCCCCGGTGGCCTCTCCCGAGACAACCGATGGAACGCAACGAACACGAAGTATCGGAC  8392
SEQ ID NO:2  TTCCCCCGGTGGCCTCTCCCGAGACAACCGATGGAACGCAACGAACACGAAGTATCGGAC  8939
             ************************************************************

SEQ ID NO:1  CAGTACGAGTCCGCACTTGGCCGCGCGATTGCTCAGTGGCGCACCGGACGGCCCATCCCG  8453
SEQ ID NO:3  CAGTACGAGTCCGCACTTGGCCGCGCGATTGCTCAGTGGCGCACCGGACGGCCCATCCCG  8452
SEQ ID NO:2  CAGTACGAGTCCGCACTTGGCCGCGCGATTGCTCAGTGGCGCACCGGACGGCCCATCCCG  8999
             ************************************************************
```

Fig. 5

METHOD FOR THE PREVENTION AND/OR THE BIOLOGICAL CONTROL OF BACTERIAL WILT CAUSED BY *RALSTONIA SOLANACEARUM*, VIA THE USE OF BACTERIOPHAGES SUITABLE FOR THIS PURPOSE AND COMPOSITIONS THEREOF

This application is a National Stage Application of PCT/ES2016/070392 filed 24 May 2016, which claims benefit of Spanish Patent Application No. P201530730, filed 26 May 2015 and which applications are incorporated herein by reference. To the extent appropriate, a claim of priority is made to each of the above disclosed applications.

TECHNICAL FIELD

The invention relates to biological control of pathogenic organisms to crop plants. More specifically, the invention relates to a method for the prevention and/or biological control of bacterial wilt caused by *Ralstonia solanacearum*, to bacteriophages useful therefor and to the use of the aforementioned bacteriophages and of compositions containing them for biological control of this bacterium.

BACKGROUND OF THE INVENTION

*R. solanacearum* produces bacterial wilt worldwide in more than 200 plant species belonging to more than 50 botanical families, and many of these species susceptible to this pathogen are of agricultural interest. There are also many other crops that are colonized by the bacteria, but do not develop symptoms, which are considered tolerant crops. This bacterium especially attacks staple crops such as potatoes in more than eighty countries, with losses exceeding 950 million dollars. For this reason, it is considered as a potential agent of bioterrorism and in the European Union (EU) as a quarantine organism (Anonymous 2000: Council Directive 2000/29/EC), which is subject to strict prevention and control measures regulated by two European directives (Anonymous 1998, 2006: Council Directive 98/57/EC and Commission Directive 2006/63/EC).

*R. solanacearum* presents great intraspecific diversity, and has therefore long been considered a complex of species consisting of four phylogenetic groups or phylotypes. In 2014, after a taxonomic revision, a reclassification of this complex was proposed (Safni et al., 2014). The phylotypes I and III of *R. solanacearum* they have been classified as the new species *R. pseudosolanacearum* and phylotype IV in the new subspecies *R. syzygii* subsp. *indonesiensis*. Phylotype II retains the name of the species *R. solanacearum.*

In the text of this document the term "the species formerly known as *R. solanacearum*" is used to refer to *R. solanacearum* in studies, data, patents, publications, literature, etc., prior to the taxonomic revision of Safni et al (2014), regardless of whether the name corresponds or not with the current classification. Furthermore, the term "*R. solanacearum*" is used to refer to the species *R. solanacearum* as described after the aforementioned taxonomic revision, i.e. the species is constituted solely by strains of phylotype II.

In Spain, as in most EU countries, there have been outbreaks of the disease caused by *R. solanacearum* in several areas, usually in potatoes and in some cases tomatoes. In all cases of outbreaks the eradication measures set out in the relevant legal regulations were implemented. However, this bacterium can survive in the environment, water, soil or other reservoirs (Alvarez et al., 2007, 2008, 2010). Thus, subsequent outbreaks have been associated with irrigation with surface water contaminated with this bacteria (Caruso et al., 2005), as these are one of the main routes of introduction and spread of the pathogen into new areas, which comes through irrigation water. In fact, it described the presence of *R. solanacearum* in various waterways both in Spain and virtually all EU countries. Therefore, the EU Directives prohibit irrigation with water contaminated with this bacteria.

This represents a practical problem for the farmer, as the most affected crops are irrigated crops (tomato and potato) and irrigation water is a scarce commodity in Spain and other countries of the Mediterranean basin, where the bacteria are also present. Also in the area where outbreaks of the disease have been detected, host plants cannot be grown over a period of at least 4 years from the detection of an outbreak.

The large capacity of survival of *R. solanacearum* in the environment (water, soil or other reservoirs) impedes control. In the past and up to the present moment, control through farming practices and chemical control are being used. Thus, in areas of the world where this pathogen is present in the soil, usually in developing countries, growing host plants is problematic and the most widely used methods of control are farming techniques with varying results. Resistant cultivars have also been obtained, however, resistance may be unstable (Hartman and Elphinstone, 1994).

With respect to control via chemical or physical treatments, generally they are not effective. The application of copper compounds, antibiotics and soil fumigants have been used without much success (Lopez and Biosca, 2005), and are also expensive and have a great impact on the environment. Other chemical treatments such as chlorination or physical treatments, such as ultraviolet radiation of water contaminated with bacterial pathogens, have limited effectiveness where particles are present in the water, even if very small (Marco-Noales et al., 2008). Furthermore, it has been shown that both of aforementioned disinfectant treatments can induce various bacteria to enter into the viable but non-culturable state (VBNC) (Oliver et al., 2005 Santander et al, 2012.) Or cause reversible cell damage (McFeters and LeChevallier, 2000). These bacterial cells in the VBNC state or having reversible damage can recover cultivability and pathogenicity after coming into contact with susceptible host plants (Santander et al., 2012). These circumstances demonstrate the need for alternative methods that preferably destroy the bacterial cells.

An alternative would be biological control using specific bacteriophages of *R. solanacearum*. This biocontrol strategy has been successful in the treatment of other diseases caused by phytopathogenic bacteria (Jones et al., 2007).

In that vein, Japanese patent JP4532959-B2 (publication number JP2005278513) describes three types of bacteriophages with bacteriolytic activity on Japanese strains of the species formerly known as *R. solanacearum* and from 2014 belonging to the new species *R. pseudosolanacearum*. Type 1, with double-stranded DNA genome (dsDNA) of approximately 250 kbp, and types 2 and 3, with a genome of single-stranded DNA (ssDNA) of 4.5 and 6 kbp respectively. Bacteriophages are characterized and distinguished by the size of their genomes and their activity against six strains of bacteria (C319, M4S, Ps29, Ps65, Ps72 and Ps74), all of which are sensitive to type 1 bacteriophages, while the type 2 only lyses one strain (the C319 strain) and type 3 lyses four of the six strains (M4s, Ps29, PS65 and Ps74) and a fifth in one trial (the C319 strain). Trials with restriction endonucleases have only been performed with type 1 bacteriophages and show that its genome (dsDNA) targets PstI and KpnI, since in the resulting restriction profiles several distinct bands are observed. Finally, the use of two of the three types of bacteriophages (types 1 and 2) to control the disease caused by species formerly known as *Ralstonia solanacearum* (currently *R. pseudosolanacearum*) by addition to soil cultivation where the plant to be protected is growing.

Japanese Patent JP4862154-B2 arises from a limitation of the above because, as is indicated therein, "it is not enough to control the effect." In this second patent is included a new type of bacteriophage lytic activity against all strains of the species formerly known as *R. solanacearum* which were tested (only a total of 15 strains) and perform characterization, but do not demonstrate their capacity for biocontrol, since no biocontrol tests were performed on plants with this new type of bacteriophage. In short, the second patent only provides a new type of lytic bacteriophage with a range of hosts that is seemingly larger than previous types.

Yamada et al (2007) describe the isolation of four types of bacteriophages that infect specific strains of the species formerly known as *R. solanacearum*, from 2014 belonging to the new species *R. pseudosolanacearum*, from soil samples taken in different areas Japan. These authors perform structural characterization including a morphological characterization by electron microscopy virions and molecular characterization by restriction analysis of the four types of bacteriophages, and some lytic activity tests with cultured bacteria in Petri dishes. Two types of bacteriophages described are mioviruses, the genus to which all the bacteriophages infecting the species formerly known as *R. solanacearum* (now *R. pseudosolanacearum*) belong described before publication of the article by Yamada et al, and the other two types are filamentous bacteriophages of the inovirus type. Among other applications, the usefulness of the bacteriophages' lytic activity as biocontrol agents for the eradication of the species formerly known as *R. solanacearum* (now *R. pseudosolanacearum*) in contaminated soils and preventing wilting caused by the bacteria in vegetable crops is suggested, showing preference for bacteriophages capable of infecting a wide range of pathogenic strains, although only testing 15 strains of this host. The only tests with plants included in the aforementioned article referred to observing a plant injected with a strain previously infected with one of the isolated lysogenic bacteriophages, concluding that filamentous phages were not satisfactory for a disease control effect. This same test method has been used in other studies of the same group also with filamentous bacteriophages of the Inoviridae family [see Addy et al., 2012 and International Patent Application WO2012/147928], where it is shown that aforementioned method of inoculation, in the case of lysogenic bacteriophage type ΦRSM, leads to the emergence of avirulent strains of *R. solanacearum* that help control the disease caused by the virulent forms of aforementioned bacteria. However, besides the fact that the inoculation tests have only been performed in 5 plants per strain and without repetition [see material and methods Addy et al., 2012], the practical application of this test method in nursery or in the field is highly questionable because the work required to inject each individual plant.

In another article by the same research group (Fujiwara et al., 2011) test results demonstrating utility as biocontrol agents on the species formerly known as *R. solanacearum* (currently *R. pseudosolanacearum*) are provided for two types of bacteriophages of the Myoviridae family described by Yamada and collaborators (2007, 2010), ΦRSA1 and ΦRSL1, as well as the effect of other additional bacteriophage ΦRSB1, with was previously isolated (Kawasaki et al., 2009). The latter belongs to the Podoviridae family and, like ΦRSA1, is capable of causing lysis in a higher number of strains, up to 13 of 15 strains of the species formerly known as *R. solanacearum* (of which at least 13 are currently classified as *R. pseudosolanacearum*) (Yamada et al., 2007; Kawasaki et al, 2009). It is shown that treatment of the bacteria with ΦRSA1, ΦRSB1 and ΦRSL1 either individually or in possible combinations, except treatment with ΦRSL1 alone, results in a rapid decrease in cell density of the host bacteria, which is only an initial decrease because is followed by the appearance of resistance visible by OD (optical density) in less than 2 days. To avoid such resistance, Fujiwara and colleagues (2011) selected the use of miovirus ΦRSL1 individually with respect to other combinations with ΦRSA1 and ΦRSB1, although it is noteworthy that this is the lowest bacteriophage lytic potential of the three.

Tests performed on plants described in the article by Fujiwara et al (2011), all done with ΦRSL1, entailed two treatments with a suspension of aforementioned bacteriophage at high concentrations conducted with a spacing of one month, first to the seed and then to the resulting plants; after two days these plants were individually inoculated with the bacterial suspension by direct contact to the cut tips of the roots (for 30 seconds) and then transplanted. This method of inoculation, like the previous used by these authors in other publications and patents, it is very difficult if not impossible to implement in nurseries or in cultivated fields. Furthermore, in aforementioned publication the reproducibility of the results is not indicated.

Fujiwara et al (2011) also describe stability tests on ΦRSL1 on two plants pre-treated with aforementioned bacteriophage and soil in contact therewith, detecting bacteriophages in the roots and in the rhizosphere soil 4 months after inoculation, although it was not verified whether the recovered bacteriophages are of the same type as those inoculated. Also, the effect of temperature on the stability of ΦRSA1, ΦRSB1 and ΦRSL1 was tested in presence and absence of soil (in SM buffer, Tris-HCl, NaCl, $MgSO_4$ and gelatine). The stability was monitored for only 15 days. At the same temperature, major differences in the stability of the three bacteriophages in the presence of soil were observed. Both in the absence and presence of soil, the differences were greater with increasing temperature but, in the absence of soil, marked differences start from 28° C. After 15 days incubation in the absence of soil at 50° C., 10% of ΦRSL1 bacteriophages survived, ΦRSB1 bacteriophages were not detected after 9 days of incubation, and after 3 days of incubation in the case of ΦRSA1.

Thus, the work of the Japanese group which includes Yamada, Addy and Fujiwara, show that in some cases and with some bacteriophages that infect the species formerly known as *R. solanacearum* (now *R. pseudosolanacearum*), can be used as agents for prevention of disease caused by the bacteria. Except in one case, the podovirus ΦRSB1, ruled out by these authors for biocontrol (Fujiwara et al., 2011), bacteriophages described and used in aforementioned tests belong to families Myoviridae or Inoviridae. In aforementioned tests, the bacteriophages are applied directly to the soil, seedlings or in roots or stems of plants. No evidence of the potential effectiveness of other means of administration of bacteriophages are given, such as perhaps through irrigation water. This is not surprising, because in Japan *R. pseudosolanacearum* has not been detected in natural watercourses, unlike the case in many European countries and in some areas of the US where this type of water is one of the reservoirs and routes of dissemination of *R. solanacearum.*

The ability to control *R. solanacearum* in water by using bacteriophages has been seen in other studies in some areas of eastern and western Europe. Thus, the summary of the Georgian patent application GEU20041089 suggests neutralization of aforementioned bacteria in plants, soil and water using a mixture of polyvalent bacteriophages in equal proportion.

The present group of inventors, however, has previously suggested the use of specific bacteriophages of the species formerly known as *R. solanacearum* in irrigation water to control bacterial wilt caused by aforementioned pathogen (Alvarez et al., 2006a; Alvarez et al, 2006b). The influence of the conditions of watercourses in the survival of the bacteria have been verified, finding that the presence of native microbiota and temperatures of 24° C. favoured the disappearance with respect to the temperature of 14° C. and sterile water used as a control (Alvarez et al., 2006a). None of these disclosures provides information about the phylotype of the tested strains, so it cannot be aforementioned that these phages could act on the current *R. solanacearum*, consisting of strains phylotype II.

The group of the present inventors have also reported the isolation of specific lytic bacteriophages of the species formerly known as *R. solanacearum* from rivers in Spain (Alvarez et al., 2006a, Alvarez et al., 2006b), but without specifying the method of isolation and the specific place of isolation of each. The authors have reported initial data on the characterization of one of them, saying that it seems to show lytic activity between 14° C. and 31° C., but not at lower temperatures (9° C.) or higher temperatures (32-39° C.) even in natural irrigation water pH ranges from 6.5 to 8.2. The initially characterized bacteriophage appears to be specific to the species formerly known as *R. solanacearum*, it shows lytic activity on 30 strains of different origins, of which the phylotype has not been disclosed. The bacteriophage showed lytic activity against other bacterial isolates of river water. Aforementioned bacteriophage also results in the reduction of bacterial wilt in tomato plants irrigated with water containing mixtures of bacteriophage and the species formerly known as *R. solanacearum*.

The data obtained by Alvarez and his colleagues support the possibility of using bacteriophages to prevent and/or control bacterial wilt, in particular by addition to irrigation water. However, data released by the group so far do not identify the specific watercourses from which the lytic bacteriophages obtained by them can be isolated. Nor was specific data given on any of aforementioned bacteriophages in order to facilitate the identification via the structural characteristics. Data on the range of temperatures and pH in which aforementioned bacteriophages are active has only been reported for one, which was also claimed to be able to lyse 30 different strains of the species formerly known as *R. solanacearum*, without specifying the particular strains in which it has proven activity.

Therefore, there is still a lack of specific lytic bacteriophages which have been established to, individually, be able to reduce bacterial wilt when added to irrigation water. For the single bacteriophage on which this type of tests have been carried out, reflected in the academic presentation made by the present group of inventors (Alvarez et al, 2006a; Alvarez et al 2006b), data have not been disclosed to allow identification other than by the lytic activity at different pHs and temperatures and the claim that decreases bacterial wilt in tomato plants, not revealing the genus or family or any concrete data on watercourses in which it is present (and from which it could be isolated) or the specific method of the isolation or the phylotype of the host strains that are affected.

Thus, neither for bacteriophages isolated by Alvarez et al. or for the bacteriophages whose use is suggested in the Georgian patent application GEU20041089 in the form of polyvalent mixtures, are there available data on survival under natural conditions, in particular on their survival in the conditions of the waters in which they would be used. A central factor in determining the suitability of a bacteriophage as biocontrol agent is precisely the survival under natural conditions. When bacteriophages of phytopathogenic are applied to soil or plants to eliminate aforementioned pathogenic bacteria, the time they can stay active until they find their target cell is the limiting factor in the process, which causes repeated applications of these bacteriophages to be required for effective control. And in the case of the species formerly known as *R. solanacearum*, its control in watercourses, especially in irrigation water and containers (tanks, storage vessels, reservoirs . . . ) it is important, especially in Europe, because:

i) the main crops affected by *R. solanacearum* are irrigated (especially potato and tomato), ii) there is currently a shortage of water in Spain and other countries of the Mediterranean basin where the pathogen is present, iii) there are official prohibitions throughout the EU to use contaminated water for irrigation of host plants (Anonymous, 1998, 2006 water: Council Directive 98/57/EC and Commission Directive 2006/63/EC), iv) no control methods available for use in water, v) a priority objective of EU policy is the conservation of the environment (Montesinos et al, 2008; Horizon 2020 Program).

Therefore, it would be desirable to control the populations of bacteria in river water and/or irrigation in a biological treatment that is effective and respectful of the natural environment. And, as was aforementioned previously, it is preferable for the method to result in the death of the bacteria.

In the case of plant pathogen *R. solanacearum*, the habitats of which are the host plants and soil, a biological agent that is supplied by water must have biological characteristics that allow it to survive in that environment, which is not the usual environment of the bacteria or its specific bacteriophages. If such survival is be prolonged and bacteriophages maintain their lytic activity on the host after long periods in water, this further favours applicability in the field as they can be transferred directly by natural and simple means such as water, without needing to encapsulated them or to provide other physical and/or biological means to protect their viability until contact with the target cell. This high survival rate would also facilitate the preparation of a commercial form, which could be in an aqueous medium without requiring refrigeration (or even lower temperatures) to maintain effectiveness.

However, it should be noted that bacteriophages are obligate intracellular parasites, and as such, require the host cell for perpetuation. Since they reach the cell in different ways, depending on the types of bacteriophages and types of host cells, survival time in the environment is expected in order to allow them to come into contact with the host cell. It is known that this time can vary between different bacteriophages, which requires study in each particular case. For example, significant variations are observed in the survival of bacteriophages the same serotype/genotype (Brion et al., 2002) or even between bacteriophages of aquatic pathogenic fish bacteria, the natural habitat of which is water (Pereira et al., 2011). In the latter case, three months has come to be regarding as good survival time of bacteriophages in water, accepting that bacteriophages displaying increased survival in water are good candidates for the control of bacterial fish diseases in aquiculture (Pereira et al., 2011).

It should be noted that R. solanacearum is a phytopathogenic bacterium whose natural environment is frequently the xylem of plants and soil, but not water. Since it is not an indigenous bacteria to aquatic environments, specific bacteriophages are not expected to have a high water survival rate. In fact, none of the previously mentioned publications and patents describes the viability and specific lytic activity of lytic bacteriophages of the species formerly known as Ralstonia solanacearum in environmental water in the absence of host cells.

And yet, it would be beneficial to have specific lytic bacteriophages against R. solanacearum, particularly that show a broad spectrum of strains of that species on which they are active and that also have a high survival rate in water, preferably of at least a month or more, more preferably several months. This could make possible biological treatment of irrigation water contaminated with R. solanacearum, using specific bacteriophages of the pathogen, which could prevent or reduce bacterial wilt in polluted areas that may impact susceptible plants. Treatment with these bacteriophages present the usual advantages over chemical treatments, as well as those associated with other treatments of biocontrol, especially with bacteriophages:

High specificity for the host cell,
Natural replication only in the host cell,
Harmless to other living beings, including microbiota beneficial to the plants to be protected,
Using biological treatment via irrigation water is easier and cheaper than chemical control, and does not require protective measures for staff during application, since it is harmless to humans,
Lower environmental impact, especially compared to copper compounds and antibiotics used in agriculture, for which many pathogens have developed resistance, reducing the effectiveness of such chemical treatments and also increasing the chemical contamination of soil, plants and fruit,
Less legal use restrictions, can be applied where chemical control is prohibited,
Since they are inert in their extracellular state, bacteriophages can be combined with other control strategies and/or biocontrol to increase disease control,
Easy, low-cost production because they increase their number in the presence of target bacteria,
Easy adjustment of the dose of bacteriophages to be used depending on the concentration of pathogen to be treated.

The present invention provides a solution to the problem of the absence of bacteriophages that display a broad spectrum of strains of the bacterium on which they are active and that also have a high survival rate in water, preferably at least one month, or more preferably, of at least several months.

SUMMARY OF THE INVENTION

The present invention is based on isolation, from river water from various regions of Spain, several bacteriophages capable of lysing the bacteria R. solanacearum, and the results of structural, functional and molecular characterization, as well as the genomics, from which the following have been established:

They all belong to the same viral species, the a new species belonging to the Podoviridae family,
They are specific to aforementioned bacteria,
They are active on a wide range of strains of R. solanacearum,
They are active at different temperatures, pHs, salinity and aeration and in the presence of light,
They have a high survival rate in water, more than three years, in natural waters of different chemical and pH compositions and at different temperatures, in the absence of the host, maintaining their lytic capacity after such long periods,
They are able to decrease wilt caused by Ralstonia solanacearum if plants are irrigated with water containing at least one of aforementioned bacteriophages.

Tests were able to verify that these features are also shared by the bacteriophage for which a partial functional characterization (lytic activity in liquid medium at different temperatures and pHs, initial host range and ability to control wilting in plants) was already described in previous work of the present group of inventors (Alvarez et al., 2006a, Alvarez et al., 2006b), without the specific origin, method of isolation, survivability having been described and without a molecular and genomic characterization having been made that would allow taxonomic classification, for which until now the family to which it belongs is unknown.

Their high specificity, the wide range of strains they are active on and, most particularly, their high survival rate in water, makes all these bacteriophages very suitable agents for biocontrol of R. solanacearum in water in natural watercourses and/or irrigation water and reservoirs, and for the prevention and/or treatment of wilt produced by aforementioned bacteria in plants. This is because maintaining lytic activity after long periods favours the use in field crops or in greenhouses or nurseries or in other situations, to which they can be transferred directly via water, a natural and simple way, without encapsulating them or any other physical, chemical and/or biological means to protect the viability until contact with the target cell. Thus, implementation costs are reduced since the number of applications required over time is reduced, the long-term efficiency of the product is increased in agricultural systems in which it is intended to be used, and outbreaks of disease caused by R. solanacearum can be prevented and combated more effectively. Thus, control agents of R. solanacearum based on these bacteriophages have a greater "added value" than other products for farmers and nursery keepers, the major potential consumers of aforementioned product.

In addition, as it was previously stated, such very high survival rate in water of the bacteriophages of the invention, while maintaining the lytic capacity after long periods in aforementioned medium in the absence of a host was not expected for a specific bacteriophage of a bacterium whose natural environment is not water as it is the case of R. solanacearum, and this ability has not been observed in other specific lytic bacteriophages of aforementioned bacteria, isolated from natural watercourses of Spain by the present inventors.

Therefore, in a first aspect, the invention relates to a bacteriophage capable of lysing cells of Ralstonia solanacearum selected from the group of:

a) vRsoP-WF2 (DSM 32039), vRsoP-WM2 (DSM 32040), vRsoP-WR2 (DSM 32041), or b) a podovirus whose genome has the sequence of SEQ ID NO:1 (corresponding to vRsoP-WF2), SEQ ID NO:2 (corresponding to vRsoP-WM2) or SEQ ID NO:3 (corresponding to vRsoP-WR2).

Hereinafter, the term "bacteriophage of the invention" is used to refer to any one of these bacteriophages.

In another aspect, the invention relates to a composition comprising at least one of the bacteriophages of the invention, or combinations of them. This composition will be considered a composition of the present invention.

In a further aspect, the invention relates to the use of at least one of the bacteriophages of the invention, or combinations, to control R. solanacearum in natural watercourses, streams of channelled water, natural water reservoirs, irrigation water and irrigation water reservoirs, by adding one or more of these bacteriophages to irrigation water or reservoirs.

In another aspect, related to the previous aspect, the invention relates to the use of at least one of the bacteriophages of the invention, or combinations, or compositions of the invention to control R. solanacearum in soil by addition of one or more of the aforementioned bacteriophages or a composition of the invention to aforementioned soil through irrigation water with which the soil is watered, or pre-treated with the aforementioned bacteriophages or aforementioned composition.

In an additional aspect, the invention relates to a method for preventing or controlling bacterial wilt caused by Ralstonia solanacearum in plants, comprising the steps of:

a) adding a composition to the water to be used for watering plants, comprising bacteriophages belonging to at least one of the bacteriophages of the invention, or combinations;

b) watering plants with aforementioned treated water.

As indicated previously, the term "*Ralstonia solanacearum*," without reference to the previous meaning of this term is used in the invention to refer to the species *R. solanacearum* as described after the last taxonomic review, i.e. the species constituted by phylotype II strains. Conversely, when the term "species formerly known as *R. solanacearum*" is used, it refers to the bacteria that were considered to be within the term *R. solanacearum* in studies, data, patents, publications, literature, etc., prior to the taxonomic revision of Safni et al. (2014), regardless of whether the name corresponds or not to the current classification.

Accordingly, the present invention, i.e. the "method for the prevention and/or biological control of wilt caused by *Ralstonia solanacearum*, by means of the use of bacteriophages useful therefor and compositions", refers to *R. solanacearum* as described after taxonomic revision of Safni et al. (2014). The three inventions of other authors mentioned in this document refer to the "species previously known as *R. solanacearum*" that, in cases where information is available (patent documents, publications, etc.), it mostly refers to strains reclassified as the new species *R. pseudosolanacearum*.

BRIEF DESCRIPTION OF THE FIGURES

Figures 1, 2:
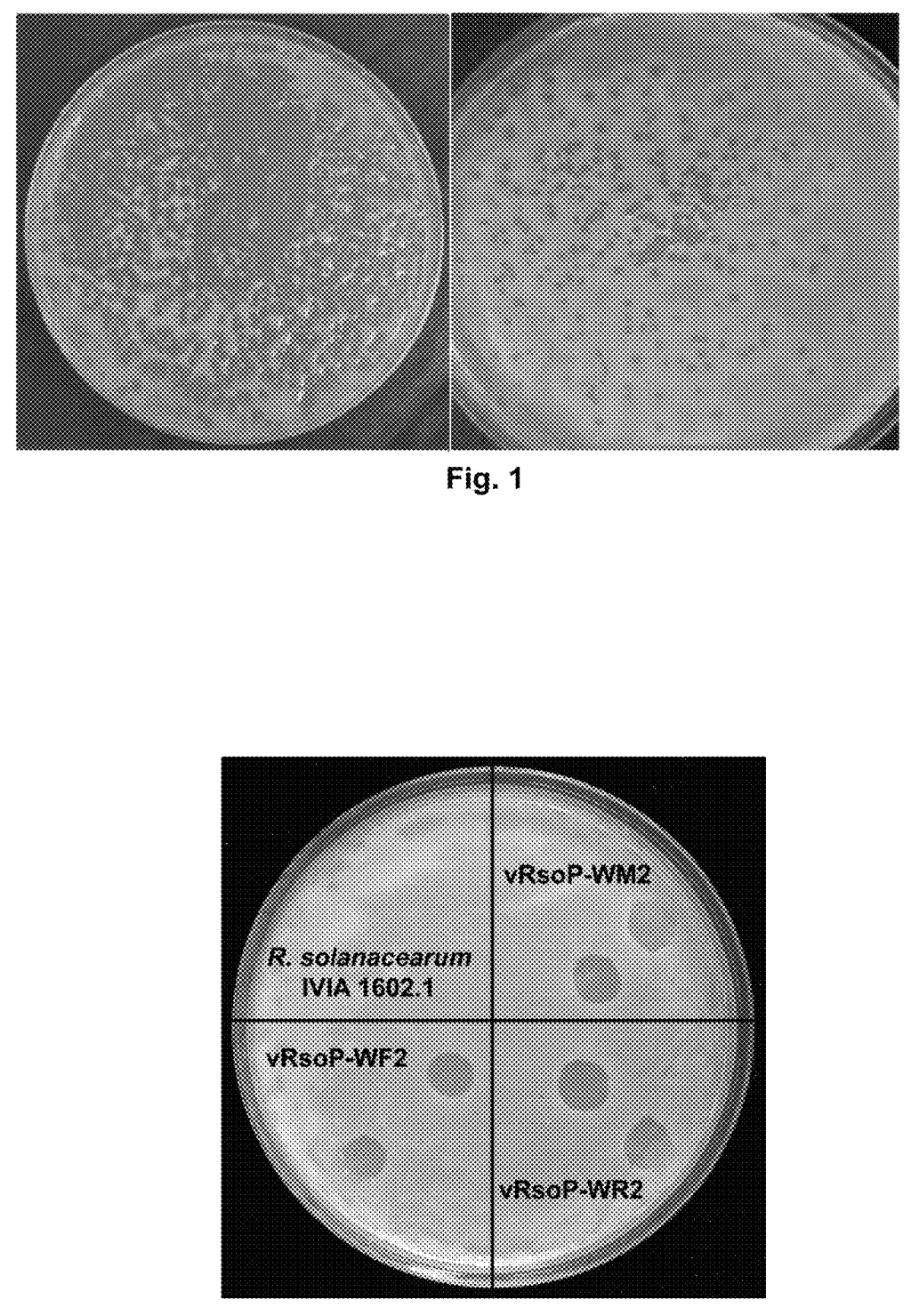

FIG. 1 shows photographs of the culture medium dishes from the lytic activity tests on the bacteriophages isolated from river water against *Ralstonia solanacearum*. Darker areas correspond to areas of lysis and/or isolated plaques, which are bacteriophage breeding areas in the bacterial lawn, which allow the lysis of the bacteria to be observed in the culture medium, the massive growth of the aforementioned bacterium being seen in whitish and opaque areas.

FIG. 2 shows a photograph of a culture medium dish with bacterial lawn from strain IVIA 1602.1 of *R. solanacearum* on which lysis tests were performed. In each quadrant, the bacteriophage contained in the suspension added to the bacterial lawn is indicated; the location of the control quadrant without bacteriophages (upper left quadrant, marked with the name of the bacterial strain) is also indicated.

FIG. 5 shows the area in which SEQ ID NO:2 (the sequence corresponding to the vRsoP-WM2) bacteriophage presents an insertion of 468 nucleotides to the sequences SEQ ID NO:1 and SEQ ID NO:3, the sequences corresponding to the bacteriophages vRsoP-WF2 and vRsoP-WR2, as well as areas close to this sequence. The presence of a hyphen in a sequence indicates a position where a nucleotide is absent in the aforementioned sequence with respect to one of or both of the other sequences, such absence allowing continued alignment in the same area. In the lower line below the corresponding sequence lines, the presence of an asterisk indicates coincidence between the nucleotides situated at that position in the three sequences.

Figure 3:
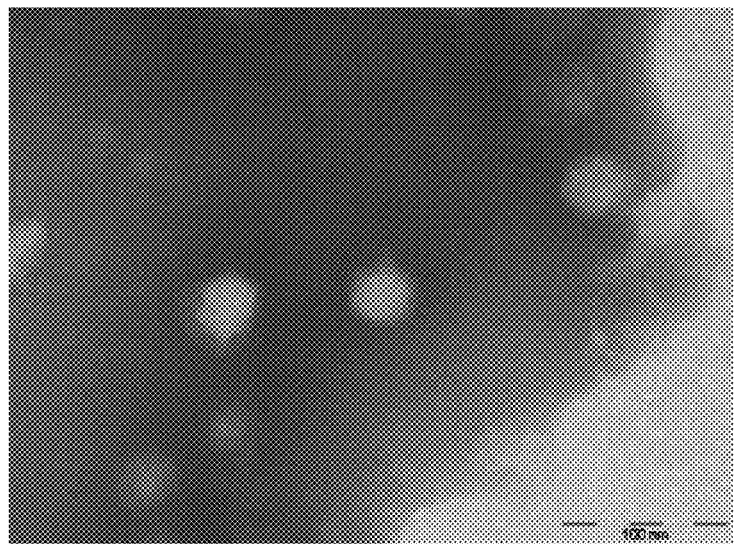
FIG. 3 shows a photograph of the bacteriophages of the present invention obtained by transmission electron microscopy after negative staining. It is observed that they present a non-enveloped, polygonal head (40 to 60 nm in diameter depending on the bacteriophage) and a short tail.

The specificity for *Ralstonia solanacearum* was also confirmed, no lytic activity being observed with bacteria isolated from river water with which tests were conducted, or with strains of other species of pathogenic plant bacteria. Again, these data are valid both for the three bacteriophages of the present invention and for combinations.

Therefore, the three bacteriophages separately, as well as combinations, fulfil the desirable characteristics for biological control agents such as high specificity by the host cell, and not posing a risk to the microbiota of water, soil or plants; being specific against *Ralstonia solanacearum*. Nor they pose a threat to the health of humans, animals or plants, being bacteriophages viruses that only infect bacteria. They are active also in a pH range compatible with the characteristics of different watercourses of Spain, and in a range compatible with the characteristics temperatures. This supports the use of bacteriophages of the present invention, individually or as combinations, and of compositions comprising such bacteriophages, to control *R. solanacearum*, whether in water from natural watercourses such as rivers, streams or creeks, natural reservoirs of water such as lakes, lagoons, ponds, springs and underground accumulations, artificial water reservoirs and dams, covered storage vessels, tanks, ponds (with or without surface covers), wells, irrigation water in general, or reservoirs of irrigation water as well as the aforementioned natural or artificial reservoirs.

In that sense, the field data collected by the present inventors on natural waters contaminated with *R. solanacearum* in different Spanish autonomous communities reveal that in the summer months (when the bacteria in water is detected and prohibits its use for irrigation) the highest daytime temperatures of these waters are between 13° C. and 17° C. and decrease at night. For example, in Salamanca and Guadalajara sampled water temperatures vary between 14° C. and 4° C. In addition, in countries in central and northern Europe with environmental water contaminated with *R. solanacearum* temperatures are lower in the summer months. Therefore, the range of activity observed for the bacteriophages of the present invention is compatible with use in natural watercourses, particularly in Spain. So is the pH range of action. However, it is not easy to add bacteriophages to a river watercourse in sufficient amount to achieve effective control of microorganisms therein, especially in the particular place where this water will be drawn for irrigation, as bacteriophages will be very diluted and will be carried along watercourse so that although their survival time is very high, such use does not favour bacteriophages to come into contact with the host cell in the section of watercourse that may be of interest, unless bacteriophages are used in short watercourses and/or watercourses with reduced flow, such as rivulets, brooks and artificial pipes, especially those leading to a reservoir where the water will stay for a longer time. Therefore, it is preferred that use should take place in a natural or artificial water reservoir, such as lakes, lagoons, ponds, streams, reservoirs, covered vessels, tanks, ponds (with or without surface covering) or wells. In them, if contamination with *R. solanacearum* is suspected, it is easier to estimate the extent of such contamination and determine the amount or concentration of bacteriophages to add depending thereon. In any case, it is preferred that the water in the reservoir should be maintained at a temperature in the temperature range of 4° C. and 30° C. inclusive, interval in which the bacteriophages of the present invention survive prolonged periods, keeping their lytic activity, both alone and as part of compositions containing at least one of them. This temperature range also comprises the ambient temperatures of survival and/or multiplication of the pathogen *Ralstonia solanacearum*, i.e. the environmental range of 4° C. and 24° C., so that the lytic activity of the bacteriophages of the present invention is effective at the temperatures that such bacteria presents a real threat of development of disease in crops. Since temperatures approaching 30° C. are not common in reservoirs of environmental water, and taking into account fluctuations in daily and seasonal environmental temperature, conditions where the average water temperature in the reservoir is between 4° C. and 24° C. inclusive are preferred.

It should be noted that the tests described in Example 4 of the present application confirm the applicability of bacteriophages of the present invention via irrigation water and the usefulness in reducing damage caused by *R. solanacearum* wilting in plants. That is why the present invention also provides a method for preventing or controlling wilt caused by *Ralstonia solanacearum* in a plant, comprising the steps of adding to the water be used to water the plant a composition comprising at least one of the bacteriophages of the present invention, or combinations, and watering the plant with the aforementioned treated water.

The proposal of pre-treatment of irrigation water before use for irrigation is an option not considered in previous studies of Japanese authors discussed hereinbefore and is an option of great interest, since the main crops affected by *R. solanacearum* are irrigated crops. Thus, although it is compatible with the invention that plant cultivation may be carried out in any of the conditions under which cultivation is possible, a possible embodiment of the invention which may be very important use on plants growing in a field, in a nursery, in a greenhouse or any other type of substrate, or hydroponics, where it can be easy to plan and implement the method of the invention within the irrigation system and also do so in ways that benefit many plants simultaneously. Moreover, but perfectly compatible with the aforementioned embodiment, within the possible application to any crop of a species susceptible and/or tolerant to *R. solanacearum*, one embodiment of the invention of great interest is that in which the plant is a species belonging to the family of the Solanaceae (Solanaceae family) and in particular one in which the plant is selected from among tomatoes (*Solanum lycopersicum*), potatoes (the two crops most frequently affected) (*Solanum tuberosum*), sweet peppers (*Capsicum annuum*) or aubergines (*Solanum melongena*). The application of the method of the invention is perfectly compatible whether the plant is in a growing area dedicated to plants of a single species, or growing areas where there are plants of different species, usually with specific sections for each, as is the case of traditional orchards, usually with an irrigation system common to them all and a common irrigation water reservoir. The characteristics of the bacteriophages of the present invention allow for individual application (plant by plant), as is the case with the applications proposed by Japanese authors and with other biocontrol agents is not necessary, to be unnecessary. Irrigation can be performed by any known system, such as traditional systems of partial or total flooding, drip irrigation, subsurface irrigation via perforated pipes, by exudation via porous pipes, or spray irrigation.

As discussed above, it is desirable that, prior to irrigation, the water which the composition with one or more bacteriophages of the present invention will be added to should be maintained at a temperature in the range of 4° C. and 24° C. which can be considered a usual environmental range, although, as bacteriophages of the invention are active up to a temperature of 31° C., this range can be extended to the range of 4° C. and 30° C. inclusive, although the latter value is unusual in environmental water reservoirs. As discussed above, conditions where the average water temperature in the reservoir is between 4° C. and 24° C. inclusive are considered suitable, given the daily and seasonal fluctuations of ambient temperature.

It is also desirable that the water pH should be in the range of 6.5 to 9.0 (both inclusive) to favour the lytic activity of the bacteriophage of the present invention.

For the same reasons discussed above, it is preferable that, prior to irrigation of the plant with water, irrigation water should stay in a reservoir, natural or artificial, from the time when the composition comprising one or more bacteriophages of the present invention is added; this approach is consistent with the addition of the bacteriophages when the water is not necessarily in such reservoir, but it is a watercourse that feeds or pours into the reservoir, especially when it is a pipe or a natural watercourse with a low flow rate that flows off of a natural watercourse with a high flow rate or a large reservoir, natural or artificial, such as a lake or a dam reservoir.

As for the reservoir itself, can be a storage vessel with or without surface coverage, including tank-type or pond-type; it can also be a natural accumulations of water, such as those that occur in the upwelling of certain springs, or artificial, natural or semi-natural wells as those formed in certain natural cavities, which are accessed by man at a later time.

On the other hand, it is important to note, as previously commented that one of the key points that determine the effectiveness of bacteriophages as biocontrol agents is their survival in the environmental conditions in which they are intended to be applied. In general, survival of the bacteriophages outside the host, as discussed previously, is extremely variable and depends on the particular nature of each bacteriophage, being strongly influenced by the surrounding environment, by conditions such as pH of the medium, temperature or sunlight (Iriarte et al., 2007). Because sunlight is a factor that often adversely affects the survival of bacteriophages under natural conditions, in considering the use in surface water, it is important for them to survive adequately in the presence of this factor. In this regard, the bacteriophages of the invention were isolated from different Spanish watercourses exposed to different levels of sunlight, unlike Japanese bacteriophages isolated from soil and plant material. Moreover, as bacteriophages of the invention were isolated from water samples in which host cells were present, the unexpected survival in water in the absence of host cells was unknown.

For all these reasons, survival of the bacteriophages isolated by the present inventors is considered an important factor, nearly a crucial feature that is an important advantage for use as a biocontrol agent in water. As described below in Example 3, the aforementioned survival was tested in the absence of the host cell in natural water from two Spanish rivers (the Tormes River in Salamanca and the Turia River in Valencia) of different chemical composition and pH, and at different temperatures. These two types of water show substantial differences in the main physico-chemical parameters referenced in the composition: specifically with the water of the Turia River values were comparatively 100 times higher in Mn, 10 times higher in Fe, between 5 and 10 times higher in chlorides and triple in nitrates; with water from the Tormes River values being approximately 4 times higher in phosphate; the average values of pH were around 8.13 in the water from the Turia River and 7.36 in the water from the Tormes river. Temperature ranges of water ranged from 3.5° C. to 20.9° C. for the Tormes River and from 11.5° C. to 22.0° C. for the water from the Turia River, i.e. temperature ranges for both environmental waters are within the temperature values used for testing survival of the bacteriophages, which were: 4° C., 14° C. and 24° C., and the pH values were 7.2 for water from the Tormes River and 8.1 for the water from the Turia River. Of these rivers, the Tormes River is contaminated with *R. solanacearum* and the use of the water is prohibited for irrigation, while contamination has not been observed in the Turia River so far. For tests of the present invention, the aforementioned natural water was filtered through a 0.22 μn filter and sterilized, so that survival tests were performed in the absence of the host. As demonstrated in Example 3, the three bacteriophages of the present invention were active and at high levels of lytic activity for more than 5 months, longer than three months considered good survival period for bacteriophages of aquatic bacteria that affected fish and which are therefore in their natural environment (Pereira et al., 2011). This high survival was observed at the three temperatures tested (4° C., 14° C. and 24° C.), which were intended to cover the environmental range of interest for use in watercourses and natural reservoirs of water, artificial reservoirs and irrigation water. Subsequently, as mentioned in Example 3, the test was continued, and it was found that, after 3 years in natural water, they remain active. This long period of survival with maintenance of lytic activity is unexpected and surprising, particularly for a lytic bacteriophage of *R. solanacearum* because it is not a native bacteria from aquatic environments, but rather its natural environment is the xylem of plants and often the ground, and it was not expected that this bacteriophages specific of such bacteria would present a high survival rate in water outside the host. In fact, in the studies of Fujiwara et al (Fujiwara et al., 2011), for example, stability was monitored only for 15 days, in which clear differences were observed among the stability of the three bacteriophages tested, more pronounced in a buffer than in the presence of soil, with marked differences observed in the survivability of the two bacteriophages of the Myoviridae family, ΦRSL1 and ΦRSA1.

As discussed previously, survival outside the host varies greatly between different bacteriophages, even among those belonging to the same serotype/genotype (Brion et al., 2002) or even among those who share a common natural habitat such as water (Pereira et al., 2011), habitat in which survival of aquatic bacteriophages of at least three months previously was considered a suitable characteristic for selecting good candidates for the control of bacterial fish diseases transmitted via water. Thus, the survival of the bacteriophages isolated by the present inventors was not predictable at all, especially considering that not even the family to which they belong was known and a high survival rate in water was not expected, since the usual habitat of its host are plants and soil, not water.

Therefore, the survival results in the absence of the host are noteworthy of the bacteriophages of the invention obtained at 24° C. because the previous results of the present inventors in survival studies of *R. solanacearum* in which lytic activity of other bacteriophages was tested in the presence of the aforementioned host bacteria indicated that the temperature of 24° C. promotes the rate of disappearance of the pathogen with respect to a temperature of 14° C. (Alvarez et al., 2007). However, at a temperature of 14° C., the bacteriophages of the invention maintain lytic activity on the host in natural water even after three years of the absence, and it has been observed that, in conditions similar to natural conditions, studies by the present inventors with other bacteriophages of this pathogen, lysis also causes a significant reduction of the populations of this bacterium (Alvarez et al., 2007). In addition, 14° C. is a temperature closer to those recorded in most aquatic habitats where the pathogen has been detected in Spain and other European countries.

Moreover, it is noteworthy that it is common conserve biocontrol agents, prior to their use, at low temperatures, preferably at 4° C., but they can also be stored at 14° C., as well as 24° C. Therefore, it is noteworthy that the bacteriophages of the present invention remain active and at high levels at all three test temperatures for more than 5 months and the survival with lytic activity can be as long as a period of three years.

Therefore, a particularly novel feature of the bacteriophages of the present invention is the survival for more than 5 months in natural water in the absence of the host cell. This is an adequate and very advantageous feature for a biological control agent, which must have features that enable it to survive in the medium in which it is intended to be applied, in this case, water.

As a result, it is compatible with the use of the method and use of the present invention that the composition containing bacteriophages should be maintained during storage and/or use, preferably at a temperature in the range from 4° C. to 24° C., inclusive, which can be considered a regular environmental range, however, since bacteriophages of the invention are active up to 31° C., this range may extend to a range from 4° C. to 30° C. inclusive, despite the latter value not being usual in environmental water reservoirs. As discussed above, an average temperature of the water in the reservoir from 4° C. to 24° C. inclusive, given the daily and seasonal fluctuations of ambient temperature, is also considered to be a suitable condition. This enables the compositions of the present invention to be easily preserved for a long time prior to their use in the form of suspensions in which the bacteriophages are in an aqueous vehicle which can be water (environmental, natural, distilled, previously sterilized, or subjected to another usual treatment for aqueous vehicles) or an aqueous solution (such as sterile saline, phosphate buffered saline, etc.) and ready to use and apply directly where needed. Therefore, the compositions of the present invention may comprise any carrier or excipient agronomically acceptable, and may be in liquid form, e.g. as an aqueous suspension, which can be prepared in water or in an aqueous solution and/or dilutions. In this way, they can be used to control *R. solanacearum* and can be applied with the method of prevention or treatment of wilt caused by the aforementioned bacteria and can be therefore ready for direct use from the stored and marketed form.

The high survival rate, with maintained lytic activity on the host, of the bacteriophages of the present invention, favours the use in the field because they can be transferred directly via water, a natural and simple way, without encapsulating or adding other physical, chemical and/or biological mediums to protect their viability until coming in contact with the target cell. This facilitates the production process, lowers costs and eliminates the need for complex formulations for implementation as well as the addition of chemicals to the environment. Thus, the high survival rate of the bacteriophages in water in the absence of the target cell reduces the implementation costs by decreasing the number of uses required over time, and increases long-term product efficiency in the agricultural systems where they are intended to be applied, and can thus more effectively prevent outbreaks of disease caused by *R. solanacearum*. All this leads to a product with more "added value" for farmers and nursery keepers, the major potential consumers of the aforementioned product, i.e. the bacteriophages of the present invention and/or compositions comprising them.

Moreover, this high survival in natural water while in the extracellular state facilitates combination with other control strategies (chemical and/or physical, and even biological) for the same plant pathogen or others, which may be an additional optional step of the method of the present invention. The method of the present invention is also compatible with the use of copper compounds, antibiotics and/or soil fumigants, whose application to the soil where plant is growing can also be considered an additional optional step of the method of the present invention.

The present invention is also compatible with additional use not only an agent of chemical or physical control, but rather as one or more additional biological control agents other than any of the bacteriophages of the present invention (other microorganisms such as bacteria, fungi and other bacteriophages, etc.). One possibility is any of the lytic or lysogenic bacteriophages previously known, which have activity against the aforementioned bacteria. For use, the additional agent may be further comprised in a composition of the present invention, or may be applied separately.

Although the preferred form of the compositions of the present invention is the liquid form, in aqueous medium, especially when applied to water to control *R. solanacearum* and/or preventing or reducing bacterial wilt caused by the aforementioned bacteria in plants which are to be irrigated with the aforementioned water, other forms of the composition are also compatible with the invention, especially those known to those skilled in the art for the conservation of bacteriophages, such as in a lyophilized form (which facilitates preservation at room temperature) or as a refrigerated and/or frozen aqueous suspension, preferably from 4° C. to –20° C., and even lower temperatures, such as –20° C. to –80° C.

As already mentioned, the compositions of the present invention may contain one of three bacteriophages whose isolation and morphological and genomic characterization is described in the present application (vRsoP-WF2, vRsoP-WM2 or vRsoP-WR2), or combinations (vRsoP-WF2 and vRsoP-WM2, vRsoP-WF2 and vRsoP-WR2, vRsoP-WM2 and vRsoP-WR2, or vRsoP-WF2, vRsoP-WM2 and vRsoP-WR2). The tests performed and described in Example 4 suggest that combinations, either two of or all three of the bacteriophages of the present invention are more effective than the use of the bacteriophages separately, so they may be a good choice for use against *Ralstonia solanacearum* in water to be treated, and particularly in water that is to be used for irrigation in order to prevent or reduce wilt caused by this bacteria. In compositions with combinations of several bacteriophages, each may be at the same concentration as in Example 4 of the present application, but different concentrations are also compatible with the invention.

Moreover, an advantage to consider of using the combination of two or more bacteriophages of the present invention is that mixtures prevent the appearance of strains of *R. solanacearum* that are resistant to the lytic action of any one of them.

Regarding the total concentration of bacteriophages in the compositions of the present invention, there are no limitations except those imposed for chemical reasons, resulting in the suspension being saturated and bacteriophages precipitating or settling. However, in practice, this is highly unlikely. One option is for the total concentration of bacteriophages of the invention to range between $10^5$ and $10^9$ plaque forming units per millilitre (PFU/ml), which are concentrations that have been tested in the Examples section of the present application and which can also be a suggested range of concentrations in order to choose the final concentration of bacteriophages desired to be present in the irrigation water. However, concentrations may be higher or lower than those included in that range, with concentrations of $10^3$ PFU/ml being able to be maintained and/or used as in section 4.1 of Example 4, or even lower, as the present inventors have obtained lysis data in liquid medium with bacteriophages of the present invention at concentrations of about $10^2$ PFU/ml. Thus, the range $10^2$ to $10^9$ PFU/ml or $10^3$ to $10^9$ PFU/mL are also possible concentration ranges of the compositions of the present invention or the conditions of action of the bacteriophages of the present invention, as well as other upper or lower limits, since the bacteriophages multiply inside the bacteria.

As far as the different bacteriophages of the present invention, under the envisaged use and/or maintenance conditions, survival data may lead to a preference for vRsoP-WM2, while macrotests carried out on plants described in Example 4, specifically on tomato plants, can lead to a preference for vRsoP-WR2, because in such tests a greater reduction in bacterial wilt was observed from applying this bacteriophage individually with respect to the other two bacteriophages of the present invention.

The invention will now be explained in more detail by the Examples and Figures described hereinafter.

EXAMPLES

Example 1

Origin and Isolation of the Bacteriophages

Lytic bacteriophages against *R. solanacearum* were isolated from several rivers of Castilla-Leon, Extremadura and Andalusia, in the vicinity of fields affected by bacterial wilt. A selection of these bacteriophages was purified and their lytic activity was tested in the laboratory against *R. solanacearum*, as shown in FIG. 1.

Among them, three bacteriophages (vRsoP-WF2, vRsoP-WM2 and vRsoP-WR2), from different origins, were chosen for further characterization.

VRsoP-WF2: isolated from the Tormes River in the vicinity of Salamanca.

VRsoP-WM2: isolated from the Cayo River in the province of Badajoz.

VRsoP-WR2: isolated from the Yator River in the area of the Alpujarras, in the province of Granada.

The three bacteriophages were purified via successive plaque passages in general LPGA medium (yeast extract [5 g]-peptone [5 g]-glucose [10 g]-agar [20 g], dissolved in distilled water [1 litre]; the glucose is sterilized by filtration and subsequently added to the rest of the medium sterilized by autoclaving) with host cells of a standard strain of *R. solanacearum* (IVIA 1602.1 strain, deposited at the French Collection of Plant-associated Bacteria [CFBP] under CFBP number 4944 and at the DSMZ free access collection under the number DSM 100387). This method is also preferred for amplification of any of the aforementioned bacteriophages of the present invention on a solid medium.

Once purified, the lytic activity, pH and temperature range, and range of hosts of them were characterized as described hereinafter.

1.1. Temperature Range.

The lytic activity observed of the characterized bacteriophages against the selected strain of *R. solanacearum* (IVIA-1602.1) is observed between 14° C. and 31° C. in all three cases.

Within this range, the routine incubation temperature of the bacteriophages to multiply in the host, both on solid medium and in liquid medium, under laboratory conditions, is between 28-30° C., because they are the values that are considered optimal for the growth of *R. solanacearum* in these conditions.

Mixtures of two (vRsoP-WF2-vRsoP-WM2, vRsoP-WF2-vRsoP-WR2, vRsoP-WM2-vRsoP-WR2) or all three bacteriophages (vRsoP-WF2-vRsoP-WM2-vRsoP-WR2) were also tested. Each of the four mixtures of bacteriophages also showed activity in the same temperature range.

1.2. pH Range.

The lytic activity observed of the characterized bacteriophages against the selected strain of *R. solanacearum* (IVIA-1602.1) tested in different irrigation water, river water, canal water and lake water, was positive in all of the aforementioned types of water at pHs ranging between 6.5 and 9.0. Similarly, the mixtures of bacteriophages showed lytic activity in the same irrigation water and, thus, within the same pH range. The minimum and maximum pH values for the lytic activity of the bacteriophages have not yet been determined.

1.3. Salinity

Since it has been reported that *R. solanacearum* can grow in the presence of NaCl at concentrations of 1%, and even sometimes up to 2%, the lytic activity of bacteriophages in brackish water of different origins was tested, with salt concentrations of about 1.5%. Lytic activity was observed with all three bacteriophages. The four mixtures of bacteriophages of the invention mentioned in point 1.1 also showed lytic activity in the tested salinity conditions.

1.4. Visible Light

Since visible light can sometimes affect the lytic activity of bacteriophages, their activity was tested in conditions of light and darkness. It was observed that after 48 hours of uninterrupted exposure to intense light (approximately 15,000 lux), the lytic activity was similar to that observed in dark conditions, so the presence of light does not affect the lytic activity of the bacteriophages of the invention. Similarly, the different mixtures of tested bacteriophages had similar lytic activity both in the presence of light and in darkness.

1.5. Aeration

Since *R. solanacearum* is an aerobic bacteria and typically grows in liquid medium with stirring (aeration), the effect of the absence of aeration on the lytic activity was determined, as in field conditions aeration is not always assured (by example in tank storage). Activity was observed both in the presence and absence of stirring, of the same magnitude, being faster with aeration. Similarly, the mixtures of the bacteriophages showed lytic activity both with and without aeration.

1.6. Specificity

Specificity was tested in Petri dishes against bacterial lawns of *R. solanacearum* strains in the LPGA general culture medium, on which two drops of a suspension of each of the three bacteriophages (FIG. 2) were poured. The lytic activity was visualized by the appearance of areas of clearance formed by lysed bacteria in the bacterial lawn where drops of the suspensions with bacteriophages were placed (FIG. 2, corresponding to the test on R. solanacearum strain IVIA-1602.1).

According to experimental data, the lytic activity of the characterized bacteriophages was positive for 35 strains of *R. solanacearum* of different origins, hosts and years of isolation (Table 1). Among the aforementioned, 13 are international in scope and/or standard. The remaining are all strains isolated in Spain, belonging to the collection of the Valencian Institute of Agricultural Research (IVIA).

TABLE 1

*R. solanacearum* strains sensitive to the lytic action of the three bacteriophages of the present invention.

| STRAIN CODE | COUNTRY OF ORIGIN | HOST | YEAR |
| --- | --- | --- | --- |
| International Strains | | | |
| NCPPB[a] 1115 | United Kingdom (Ex Egypt) | Potato | 1961 |
| NCPPB 1584 | Cyprus | Potato | 1963 |
| NCPPB 2505 | Sweden | Potato | 1972 |
| NCPPB 2797 | Sweden | Solanum dulcamara | 1974 |
| BR 264 | United Kingdom | Solanum dulcamara | 1993 |
| Bordeaux 11-47 | France | Aubergine | 1994 |
| Nantes 9-46 | France | Tomato | 1994 |
| 550 | Belgium (Ex Turkey) | Potato | 1995 |
| IPO-1609 | Netherlands | Potato | 1995 |
| Port 448 | Portugal | Potato | 1995 |
| W 12 | Belgium | Potato | 1996 |
| WE 4-96 | United Kingdom | River Water | 1996 |
| Tom 1 | United Kingdom | Tomato | 1997 |
| Strains from Spain | | | |
| IVIA[b]-1602.1 | Canary Islands | Potato | 1996 |
| IVIA-2049.53 | Canary Islands | Soil | 1999 |
| IVIA-2068.58a | Canary Islands | Potato | 1999 |
| IVIA-2068.61a | Canary Islands | Potato | 1999 |
| IVIA-2093.3.1 | Canary Islands | Potato | 1999 |
| IVIA-2093.5T.1a | Canary Islands | Potato | 1999 |
| IVIA-2128.1b | Castile-Leon | Potato | 1999 |
| IVIA-2128.3a | Castile-Leon | Potato | 1999 |
| IVIA-2167.1a | Castile-Leon | River Water | 1999 |
| IVIA-2167.2b | Castile-Leon | River Water | 1999 |
| IVIA-2528.A$_{1-2}$ | Castile-Leon | River Water | 2001 |
| IVIA-2528.A$_3$.1 | Castile-Leon | River Water | 2001 |
| IVIA-2528.54.A$_2$ | Castile-Leon | River Water | 2001 |
| IVIA-2751.11 | Extremadura | River Water | 2003 |
| IVIA-2762.1 | Extremadura | Tomato | 2003 |
| IVIA-2762.4 | Extremadura | Tomato | 2003 |
| IVIA-3090.1 | Andalusia | Tomato | 2005 |
| IVIA-3090.5 | Andalusia | Tomato | 2005 |
| IVIA-3205.A.22 | Castile-La Mancha | River Water | 2006 |
| IVIA-3243 | Andalusia | Tomato | 2006 |
| IVIA-3359.9 | Castile-La Mancha | River Water | 2007 |
| IVIA-3359.10 | Castile-La Mancha | River Water | 2007 |

[a]NCPPB: National Collection of Plant Pathogenic Bacteria, United Kingdom.
[b]IVIA: Bacteria Collection of the Valencian Institute of Agricultural Research, Spain.

Strains from the NCPPB are available in this international collection. The other strains are available in the IVIA collection of phytopathogenic bacteria.

Specificity was also tested against other species of plant pathogenic bacteria and various bacterial isolates of river water to assess the possible impact of the isolated bacteriophages on the microbiota of natural water.

The lytic activity was negative for the 14 bacterial isolates of river water in the tests, which were selected from various water samples and presented different colonial morphologies from each other and with respect to the host. The activity was also negative for the 11 tested phytopathogenic bacteria strains belonging to other genera, demonstrating the specificity of the selected bacteriophages against *Ralstonia solanacearum*. The same results were obtained with the four possible mixtures of the aforementioned bacteriophages.

Example 2

Structural Characterization: Morphological and Molecular Characterization 2.1. Morphological Characterization.

A study of the morphology of the selected bacteriophages was carried out via transmission electron microscopy of the viral particles after negative staining with phosphotungstic acid. It is observed that they present the characteristic morphology of the Podoviridae family: polygonal, non-enveloped heads 40 to 60 nm in diameter and short tails (FIG. 3). The bacteriophages of this family are also characterized by a genome of double-stranded DNA, a fact which was confirmed in the tests described below.

2.2. Molecular Characterization.

2.2.1. Extraction of the DNA of the Three Bacteriophages.

Concentrated capsid suspensions were obtained from the three types of bacteriophages from the corresponding bacterial lysates (filtered and treated with DNAse and RNAse to degrade the bacterial nucleic acids), by polyethylene glycol capsid precipitation protocol. After treatment of the aforementioned capsids with proteinase K, extraction of genomic DNA was performed after the addition of phenol, chloroform and isoamyl alcohol. After confirming that concentration and purity were adequate, the obtained DNAs were analysed by electrophoresis in agarose gel to verify the integrity as a preliminary step to the restriction analysis (see section 2.2.2) and purification for subsequent sequencing (see section 2.2.3).

2.2.2. Restriction Analysis of the Genomes of the Three Bacteriophages.

From the obtained genomic DNAs of the three bacteriophages, restriction analysis was carried out with various restriction enzymes, chosen to give a banding pattern belonging to T7 genus bacteriophages of the Podoviridae family. These enzymes were KpnI, ScaI, SpeI and XmnI. PstI was also tested because it is an enzyme used to cut the genome of bacteriophages of the species formerly known as *R. solanacearum* described in Japanese Patent JP4532959-B2 (publication number JP2005278513).

Figure 4:
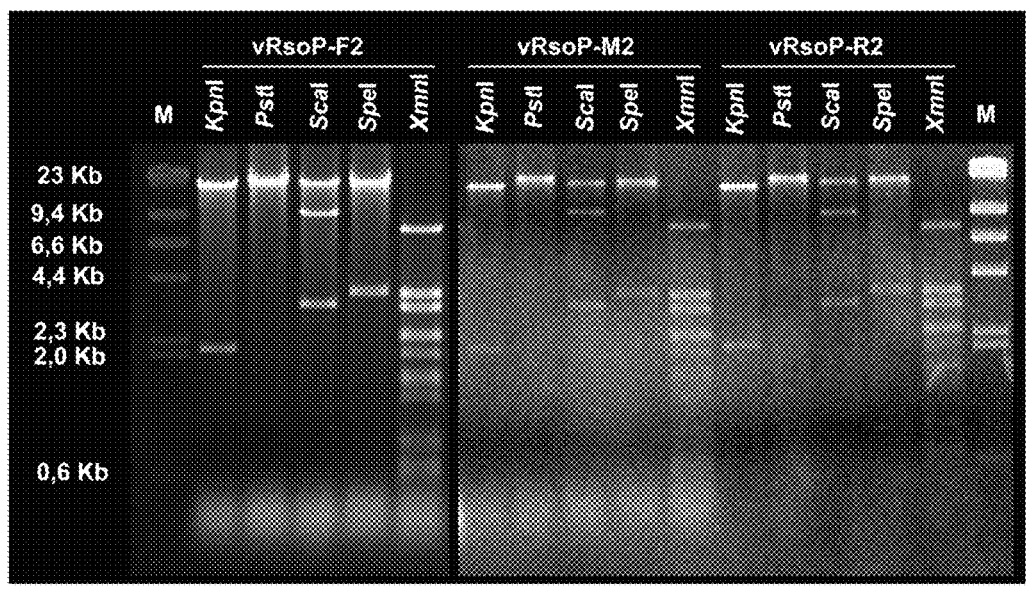
FIG. 4 is a photograph obtained after subjecting to electrophoresis the samples in which digestion of the DNA of bacteriophages vRsoP-WF2, vRsoP-WM2 or vRsoP-WR2 (as indicated at the top of the photograph) had been carried out with various restriction enzymes indicated above each column. The columns at the extreme right and left ends correspond to the pattern of molecular weights (M): λ phage DNA digested with HindIII.

As shown in FIG. 4, the profile bands obtained with these five restriction enzymes is apparently the same for the three bacteriophages: complete digestion with XmnI and partial digestion with KpnI, ScaI and SpeI was observed, while no PstI digestion was appreciable. These results indicate the genetic proximity of the three bacteriophages to each other, and the difference from the bacteriophages of Japanese patent application JP4532959-B2, whose genomes themselves are cut by PstI.

2.2.3. Mass Sequencing of Genomic DNAs of the Three Bacteriophages and Bioinformatic Analysis.

From the resulting genomic DNA belonging to each of the three bacteriophages, we proceeded to the massive sequencing of the nucleotide bases and subsequent bioinformatic analysis and complete annotation of the genomic sequences found (SEQ ID NO: 1, corresponding to vRsoP-WF2; SEQ ID NO: 2, corresponding to vRsoP-WM2 and SEQ ID NO: 3, corresponding to vRsoP-WR2). This part was entrusted to the Valgenetics, S.L. (University of Valencia Science Park, Valencia, Spain).

The main findings were as follows:

The assembly of sequences obtained by massive sequencing yielded final sequences assembled with 100% fidelity, whose sizes are shown in Table 2.

TABLE 2

Size of the Genomic Sequences Obtained for Each Bacteriophage.

| SEQ ID NO: | Bacteriophage | Number of Base Pairs (bp) |
|---|---|---|
| 1 | vRsoP-WF2 | 40,409 |
| 2 | vRsoP-WM2 | 40,861 |
| 3 | vRsoP-WR2 | 40,408 |

The results indicated that each of the majority sequences included in the samples of SEQ ID NO: 1 (corresponding to vRsoP-WF2), SEQ ID NO: 2 (corresponding to vRsoP-WM2) and SEQ ID NO: 3 (corresponding to vRsoP-WR2) is readily identifiable as a complete genome of a bacteriophage belonging to the genus of T7-like viruses, which is the type species of enterobacteria bacteriophage known as T7 (enterobacteria phage T7), which belongs to the Podoviridae family.

Comparing the genomes of the three bacteriophages, it was showed that they were 99% identical over the whole of the genome. However, analysis of these sequences made obvious the presence of small genomic differences such as mutations, insertions and deletions distributed throughout the genome. These differences are higher in the sequence of SEQ ID NO: 2 (corresponding to vRsoP-WM2) than in the sequences of SEQ ID NO: 1 (corresponding to vRsoP-WF2) and SEQ ID NO: 3 (corresponding to vRsoP-WR2), which are almost identical. Thus, the sequence of SEQ ID NO: 2 contains an insertion of 468 nucleotides compared to the sequences of SEQ ID NO: 1 and SEQ ID NO: 3. FIG. 5 shows the sequence alignment extract corresponding to the area of the insertion. Small differences found in the nucleotide sequences indicated that bacteriophages vRsoP-WF2, vRsoP-WM2 and vRsoP-WR2 are different bacteriophages of the same viral species (Table 3).

TABLE 3

Comparison of the Sequences of the Genomes of Bacteriophages vRsoP-WF2, vRsoP-WM2 and vRsoP-WR2

| Compared Sequence (SEQ ID NO:) | Pattern Sequence of the Comparison (SEQ ID NO:) | Coverage* | Identity** |
|---|---|---|---|
| 1 | 2 | 98% | 99% |
| 1 | 3 | 100% | 99% |
| 2 | 3 | 99% | 99% |

*Homology between sequences of compared genomes, expressed as a percentage.
**Nucleotides matching within areas of homology of the genomes compared, expressed as a percentage.

Additionally, using the BlastN and Blast2Seq analyses carried out with the tools accessible to the public via the website of the National Center for Biotechnology Information of the USA (www.ncbi.nlm.nih.gov/), it was found that the genomes of bacteriophages vRsoP-WF2, vRsoP-WM2 and vRsoP-WR2 exhibit some regions with high identity (about 70%) with bacteriophages: Ralstonia RSB1, Vibrio VP4 and, especially, Rhizobium RHEph01, all of them being T7-like bacteriophages (Table 4). These regions (corresponding to 5-23% of the entire genome of bacteriophages vRsoP-WF2, vRsoP-WM2 and vRsoP-WR2) belong to highly conserved regions.

TABLE 4

Comparison of the Sequences of the Genomes of Bacteriophages vRsoP-WF2, vRsoP-WM2 and vRsoP-WR2 with Several T7-like Bacteriophage Genomes.

| Compared Sequence (SEQ ID NO:) | Genome of the Virus Pattern Sequence of the Comparison (GenBank Access Number) | Coverage* | Identity** |
|---|---|---|---|
| 1 | Φ *Ralstonia* RSB1 (AB597179.1) | 2% | 84% |
| 1 | Φ T7 (NC_001604.1) | 5% | 67% |
| 1 | Φ *Rhizobium* RHEph01 (JX483873.1) | 19% | 68% |
| 1 | Φ *Vibrio* VP4 (NC_007149.1) | 5% | 70% |
| 2 | Φ *Ralstonia* RSB1 (AB597179.1) | 15% | 66% |
| 2 | Φ T7 (NC_001604.1) | 5% | 67% |
| 2 | Φ *Rhizobium* RHEph01 (JX483873.1) | 23% | 68% |
| 2 | Φ *Vibrio* VP4 (NC_007149.1) | 4% | 70% |
| 3 | Φ *Ralstonia* RSB1 (AB597179.1) | 15% | 66% |
| 3 | Φ T7 (NC_001604.1) | 5% | 67% |
| 3 | Φ *Rhizobium* RHEph01 (JX483873.1) | 22% | 68% |
| 3 | Φ *Vibrio* VP4 (NC_007149.1) | 2% | 70% |

*Homology between sequences of compared genomes, expressed as a percentage.
**Nucleotides matching within areas of homology of the genomes compared, expressed as a percentage.

These results reveal that, except in these conserved regions within the T7-like bacteriophages, the genomes of bacteriophages vRsoP-WF2, vRsoP-WM2 and vRsoP-WR2 contain a highly divergent nucleotide sequence with respect to other bacteriophages deposited in GenBank. Therefore, these high differences in nucleotide sequence guarantee that bacteriophages vRsoP-WF2, vRsoP-WM2 and vRsoP-WR2 correspond to a new species within the genus of T7-like viruses.

Figure 6:
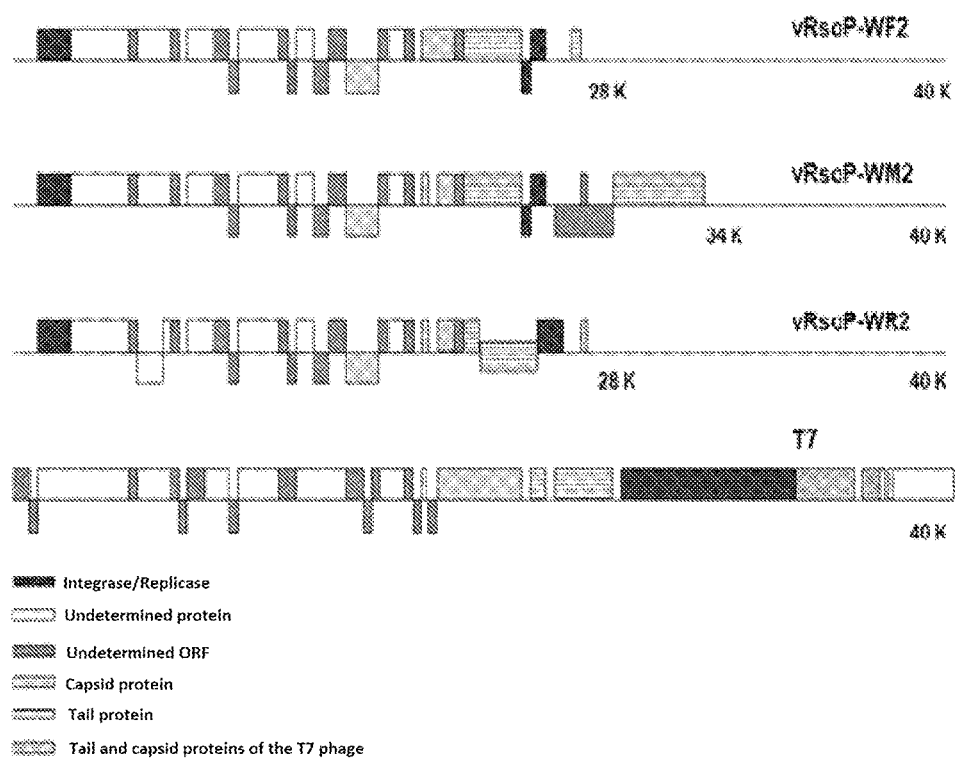
FIG. 6 shows the genomic organization of bacteriophages vRsoP-WF2, vRsoP-WM2, and vRsoP-WR2 as compared to bacteriophage T7. In various shades of grey or with weaves of parallel lines in different directions, the location of functional open reading frames (ORFs) that have been identified using the BLAST tool is indicated, as specified in the legends in the lower part of the figure. It is noted that the three bacteriophages possess a genomic organization and expression of the ORFs similar to bacteriophage T7 in part of the genome.

Moreover, the identification of open reading frames (ORF) and characteristic features of the bacteriophages revealed that the sequences of the genomes of bacteriophages vRsoP-WF2, vRsoP-WM2 and vRsoP-WR2 have genomic organization and ORF expression that is mutually similar, and similar to T7-like bacteriophages in part of the genome (FIG. 6).

In summary, the three bacteriophages of the present invention are three isolates of the same viral species, being a new species classified as belonging to the genus T7 of the Podoviridae family, with organization very similar but distinct from the T7 bacteriophages deposited in Gen Bank (FIG. 6). The novel bacteriophages have different sequences to T7 bacteriophages, only resembling in some highly conserved areas, such as those related to replication and encapsidation.

Example 3

Survival of the Three Bacteriophages in Natural River Water

The survival of the three selected bacteriophages was tested in two different types of river water: Tormes, from Salamanca, and Turia, from Valencia, both in Spain. These two types of water show substantial differences in the main physico-chemical parameters analysed of the composition: specifically with the water of the Turia River values were comparatively 100 times higher for Mn, 10 times higher for Fe, between 5 and 10 times higher for chlorides and triple for nitrates; with water from the Tormes River, values were approximately 4 times higher in phosphate; the average values of pH were around 8.13 in the water from the Turia River and 7.36 in the water from the Tormes river. Temperature ranges of water ranged from 3.5° C. to 20.9° C. for the Tormes River and from 11.5° C. to 22.0° C. for the water from the Turia River, i.e. temperature ranges for both types of environmental water are within the temperature values used for testing survival of the bacteriophages, which were: 4° C., 14° C. and 24° C., and the pH values were 7.2 for water from the Tormes River and 8.1 for the water from the Turia River.

Surprisingly, it was observed that all the bacteriophages maintained their lytic activity against *R. solanacearum* after more than five months under these conditions, in the absence of the host since, prior to inoculation, the water had been filtered through a 0.22 µm filter and autoclaved.

Figure 7:
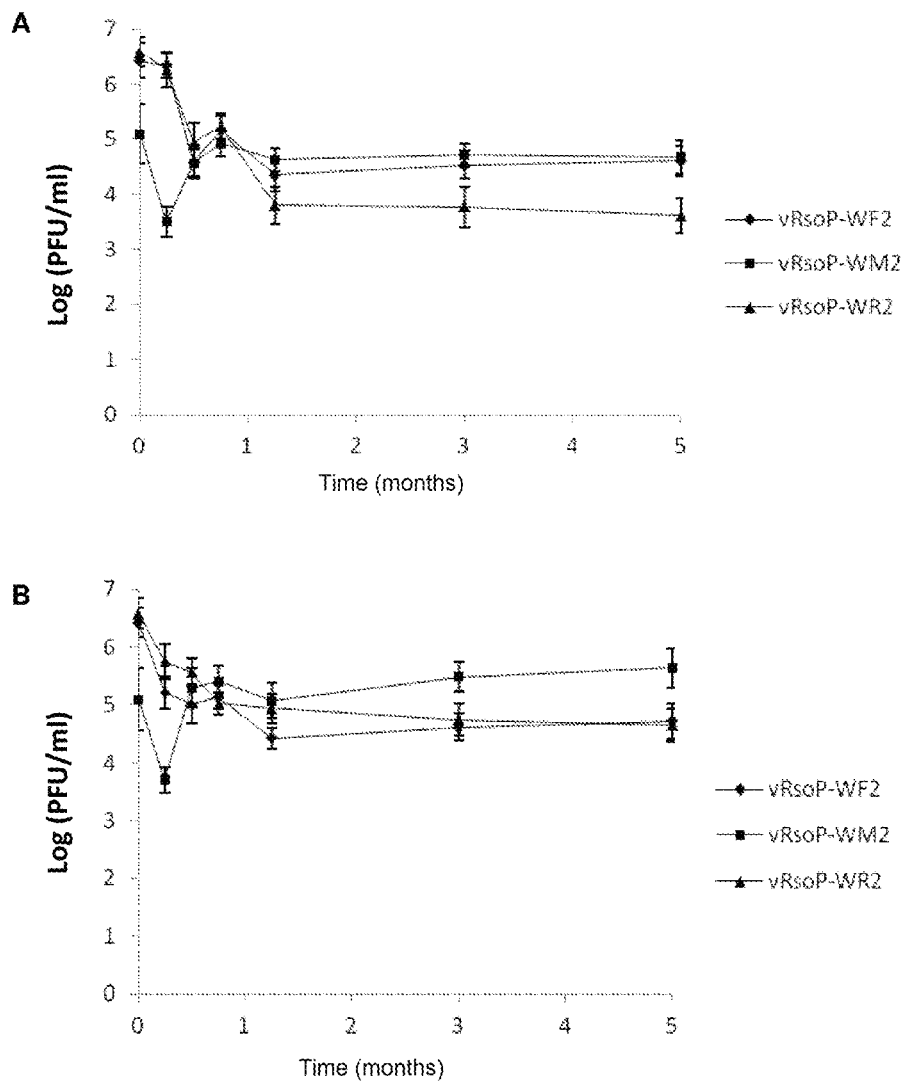
FIG. 7 shows the survival curves of bacteriophages vRsoP-WF2, vRsoP-WM2 and vRsoP-WR2, at incubated at 14° C. in the absence of host cells in water from the Tormes river (panel A, top) and the Turia River (panel B, bottom). Survival is expressed as the base 10 logarithm of the plaque forming units detected per millilitre (PFU/ml) in samples taken at the times indicated on the x/y graph.

FIG. 7 shows graphics for the evolution of plaque forming units per millilitre (PFU/ml) of the bacteriophages in both the water from the Tormes River (panel A) and from the Turia River (panel B), in samples incubated at 14° C. It is observed that PFU/ml are maintained in the absence of *Ralstonia solanacearum*. The survival curves of the three bacteriophages samples kept at 4° C. and 24° C. were similar.

Thus, it is noteworthy that the three bacteriophages are active and have high lytic activity at all three temperatures tested for more than 5 months.

In addition, survival and maintenance of the lytic activity of all bacteriophages were confirmed at 4° C. and 14° C. for a period of time as long as three years. This result is important for conservation within this temperature range when such long storage periods are required.

Example 4

Biocontrol of Bacterial Wilt Caused by *R. solanacearum*

4.1. Ability to Control Bacterial Populations in Natural River Water.

Since the three bacteriophages of the invention had similar lytic activity at the different tested temperatures and pH values in natural water, initially one of them was chosen as a model (bacteriophage vRsoP-WF2) to perform biocontrol tests of bacterial wilt caused by *R. solanacearum*.

Figure 8:
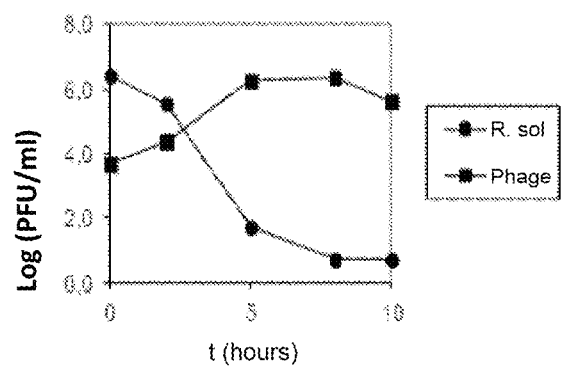
FIG. 8 shows a graph of the lytic activity of the bacteriophage vRsoP-WF2 added to an initial concentration of $10^3$ plaque forming units per millilitre (PFU/ml) in sterile river water, to which $10^6$ colony forming units per millilitre (CFU/ml) of *Ralstonia solanacearum* were added. A decrease within time of the CFU/ml corresponding to the bacteria (expressed in the form of the base 10 logarithm, points indicated with a filled circle) and an increase in PFU/ml corresponding to the bacteriophage (also expressed as the base 10 logarithm, points indicated with a filled square) were observed.

A bacteria-bacteriophage coinoculation test was carried out in sterile river water, in a closed system controlled in the laboratory, for simultaneous quantification of the population levels of both microorganisms over time. To do this, the bacteria was inoculated at a concentration of $10^6$ of colony forming units per millilitre (CFU/ml) in the liquid medium (sterile river water) and the bacteriophage was added at a concentration of $10^3$ plaque forming units per millilitre (PFU/ml). As shown in FIG. 8, it was confirmed that populations of the inoculated bacteria (reference strain IVIA-1602.1 of *R. solanacearum*) descended substantially in a few hours due to the lytic activity of the inoculated bacteriophages (bacteriophage vRsoP-WF2), the aforementioned pathogenic bacteria virtually disappearing after about 10 hours.

4.2. Tests of Biocontrol of Bacterial Wilt in Host Plants: Bacteriophage vRsoP-WF2.

Figure 9:
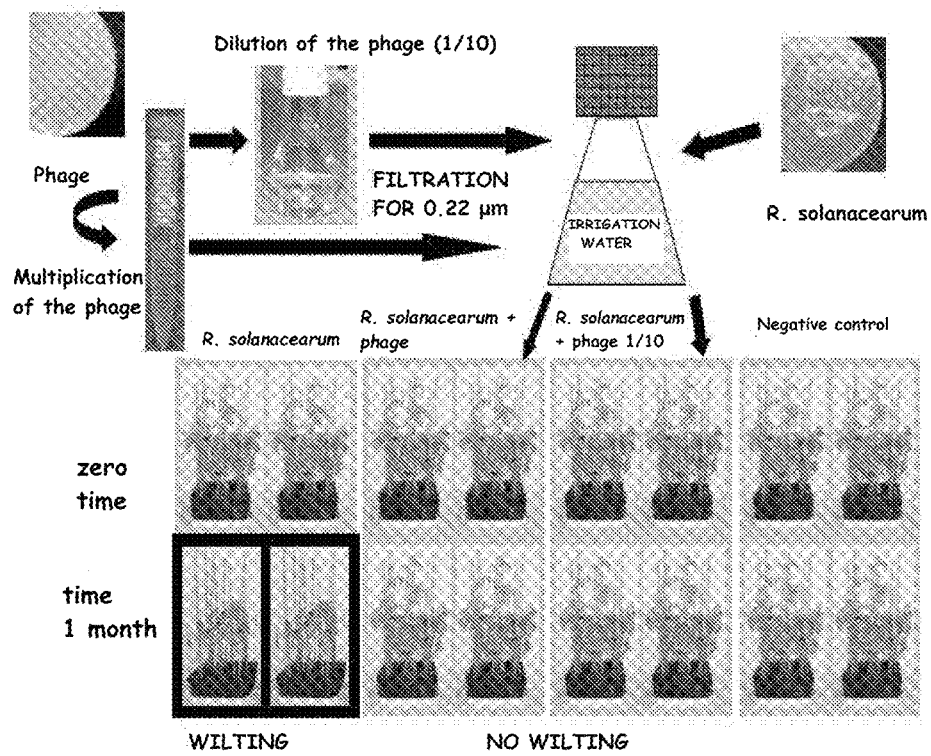
FIG. 9 shows an illustrating scheme of the experimental procedure of the use of the bacteriophages of the invention on irrigation water developed by the present inventors for the ability to control bacterial wilt. At the bottom, photographs of the condition of the plants at the beginning of the test (time zero, top row of photographs) and after 1 month (1 month, bottom row of photographs) are shown for each of the combinations of R. solanacearum and the bacteriophage vRso active in the same ranges of pH and temperature, thus expanding the aforementioned characterization to the three bacteriophages of the present invention. The same results were obtained with mixtures of two of the bacteriophages (vRsoP-WF2 with vRsoP-WM2, vRsoP-WF2 with vRsoP-WR2, or WM2-vRsoP with vRsoP-WR2) or the combination of all three (vRsoP-WF2, vRsoP-WM2 and vRsoP-WR2). Thus, mixtures comprising combinations of these bacteriophages as well as the compositions comprising at least one of the bacteriophages of the present invention are a possible embodiment of the compositions of the present invention.

The ability of the river water bacteriophage vRsoP-WF2 for biocontrol of the disease caused by *R. solanacearum* was tested in two independent experiments, watering plants of a susceptible host (tomato plants) with a concentration of the standard bacterial strain IVIA 1602.1 ($10^5$ CFU/ml) and two different concentrations of the aforementioned bacteriophage ($10^6$ and $10^9$ PFU/ml), and the decimal dilutions ($10^5$ and $10^3$ PFU/ml, respectively), in conditions of optimum temperature and humidity for the development of the disease. The experimental procedure is shown in FIG. 9.

Figure 10:
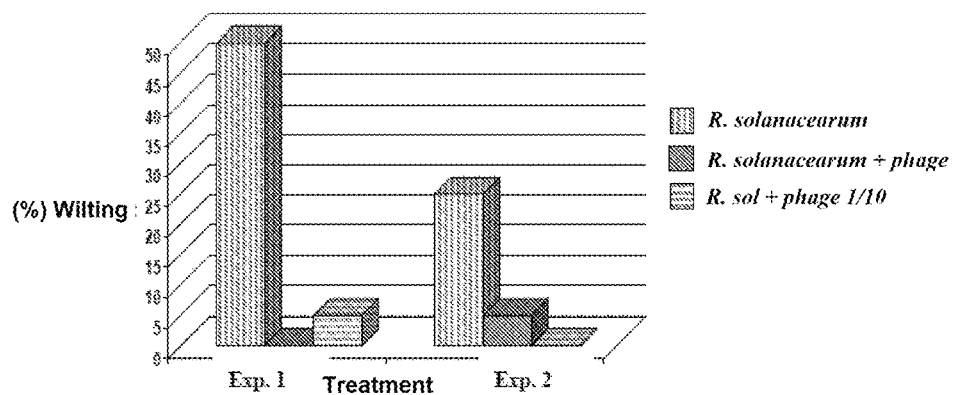

The results of both experiences are shown in FIG. 10. Overall, the disease incidence decreased to 0-5% in plants irrigated with the pathogen and the bacteriophage, in independent experiments, while in the controls without bacteriophages wilt incidence was 25-50%.

4.3. Tests of Biocontrol of Bacterial Wilt in Host Plants: vRsoP-WF2, vRsoP-WM2, vRsoP-WR2, and their Combinations.

Similar to the experiments of biocontrol in plants carried out with the bacteriophage vRsoP-WF2 described in section 4.2, a macrotest was carried out, which could simultaneously study the ability for biocontrol of each of the three bacteriophages vRsoP-WF2, vRsoP-WM2 and vRsoP-WR2, separately as well as in combinations of two and a mixture of all three. This is considered a macroassay, since it is performed with a large number of plants requiring sufficient room for incubation and people qualified for carrying it out. In all cases, tomato plants, which are a host susceptible to the pathogen, were tested, wherein approximately 35 plants per experimental condition were inoculated, which is approximately 315 plants. Inoculated plants were kept in a climatic chamber of suitable size, in day/night cycles of 16 hours of light at 26° C. and 8 hours dark at 22° C. and a humidity of about 70%, in conditions of biological containment, in a BSL3 laboratory. In the cited macroassay, the concentration of R. solanacearum (strain IVIA 1602.1) in irrigation water was $10^5$ CFU/ml, while the total concentration of bacteriophages was $10^7$ PFU/ml in all the tested experimental conditions.

Figure 11:
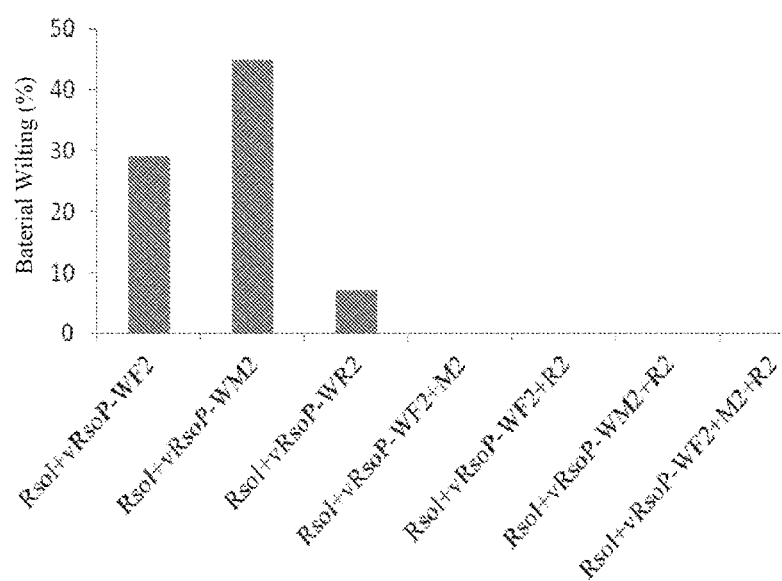

The graph of FIG. 11 shows the results obtained. These results indicate that:

The bacteriophage vRsoP-WR2 is the most effective of the three, resulting in a greater decrease of bacterial wilt when added to irrigation water at the same concentration as the other two bacteriophages.

Any mixture of the bacteriophages (either binary combinations, or the combination including the three) are more effective than the separate bacteriophages.

All these experiments demonstrate the lytic potential of the bacteriophages of the present invention, isolated at different places in Spain, for the biocontrol of R. solanacearum and, therefore, the applicability of the aforementioned lytic activity in both the treatment of environmental water for agricultural use that has been contaminated with the aforementioned pathogen, or other uses, such as in the prevention and/or control of the disease caused in the field. This biocontrol ability is especially important, since it is considered that there is currently no effective control methods available via soil or water. And, in this case, as previously discussed and demonstrated in the aforementioned experiments, the biocontrol agents provided by the present invention have the unexpected feature of a high survival rate in water under normal environmental temperatures in Spain, which it is an advantage for use on plants via irrigation water and for the control and prevention of the presence of R. solanacearum therein, and for easy and prolonged maintenance of the marketed forms of the bacteriophages of the invention prior to use. Such maintenance may take place in an aqueous medium for a long time without severe loss of lytic activity and not even require, prior to the application to water, pre-dilution of the bacteriophages or their mixtures with any kind of physical or chemical vehicle to facilitate the interaction with the target bacteria or to ensure the stability before coming into contact with it, so that applying bacteriophages to irrigation water, water streams or water reservoirs can be simply by pouring them into R. solanacearum contaminated water to be controlled.

Deposit of Microorganisms

The bacteriophages vRsoP-WF2, vRsoP-WM2 and vRsoP-WR2, with ability to lyse R. solanacearum cells, have been deposited in the German Collection of microbial cultures Leibniz-Institut DSMZ-Deutsche Sammlung von Mikro-organismen and Zellkulturen GmbH, Inhoffenstrasse 7B, 38124 Braunschweig, Germany, following the rules of the Budapest Treaty for the deposit of microorganisms for patent purposes, on the following dates and assigned the following access numbers (Table 5).

TABLE 5

Data on the Deposit of Bacteriophages in the DSMZ German Collection.

| Material | Deposit Date | Access Number |
|---|---|---|
| vRsoP-WF2 | 15 Apr. 2015 | DSM 32039 |
| vRsoP-WM2 | 15 Apr. 2015 | DSM 32040 |
| vRsoP-WR2 | 15 Apr. 2015 | DSM 32041 |

REFERENCES

Addy, H. S., Askora, A., Kawasaki, T, Fujie, M. & Yamada, T. 2012. Utilization of filamentous phage RSM3 to control bacterial wilt caused by Ralstonia solanacearum. Plant Diseases. 96:1204-1209.

Álvarez, B., Biosca, E. G. & Lopez, M. M. 2006a. River water biota affecting Ralstonia solanacearum survival: characterization of specific bacteriophages and its potential use for biocontrol in irrigation water. The 4th International Bacterial Wilt Symposium. Abst. p. 46. York (UK).

Álvarez, B., Biosca, E. G. & López, M. M. 2006b. Caracterizacion de fagos liticos de Ralstonia solanacearum aislados de agua de rio: use potencial en biocontrol. XIII Congreso de la Sociedad Española de Fitopatologia. Abst. p. 62. Murcia Álvarez, B., López, M. M. & Biosca, E. G. 2007. Influence of native microbiota on survival of Ralstonia solanacearum phylotype II in river water microcosms. Appl. Environ. Microbiol. 73:7210-7217.

Álvarez, B., López, M. M. & Biosca, E. G. 2008. Survival strategies and pathogenicity of Ralstonia solanacearum phylotype II subjected to prolonged starvation in environmental water microcosms. Microbiology. 154:3590-3598.

Álvarez, B., Biosca, E. G. & López, M. M. 2010. On the life of Ralstonia solanacearum, a destructive bacterial plant pathogen. En: Current research, technology and education topics in applied microbiology and microbial biotechnology. Mendez Vilas, A. ed., pp. 267-279. World Scientific Publishing, Singapore.

Anonymous. 1998. Council Directive 98/57/EC of 20 Jul. 1998 on the control of Ralstonia solanacearum (Smith) Yabuuchi et al. Off J Eur Communities L235, 1-39.

Anonymous. 2000. Council Directive 2000/29/EC of 8 May 2000 on protective measures against the introduction into the Community of organisms harmful to plants or plant products and against their spread within the Community. Off J Eur Communities L169, 1-112.

Anonymous. 2006. Commission Directive 2006/63/EC of 14 Jul. 2006: amending Annexes II to VII to Council Directive 98/57/EC on the control of Ralstonia solanacearum (Smith) Yabuuchi et al. Off Eur Communities L206, 36-106.

Brion, G. M., Meschke, J. S. & Sobsey, M. D. 2002. F-specific RNA coliphages: occurrence, types, and survival in natural waters. Water Research. 36:2419-2

Caruso, P., Palomo, J. L., Bertolini, E., Álvarez, B., López, M. M. & Biosca, E. G. 2005. Seasonal variation of Ralstonia solanacearum biovar 2 populations in a Spanish river: recovery of stressed cells at low temperatures. Appl. Environ. Microbiol. 2005. 71:140-8.

Fujiwara, A., Fujisawa, M., Hamasaki, R., Kawasaki, T., Fujie, M. & Yamada, T. 2011. Biocontrol of Ralstonia solanacearum by treatment with lytic bacteriophages. Appl. Environ. Microbiol. 77(12):4155-4162.

Hartman, G. L. & Elphinstone, J. G. 1994. Advances in the control of Pseudomonas solanacearum race 1 in major food crops. En: Bacterial wilt: the disease and its causative agent, Pseudomonas solanacearum. Hayward, A. C. & Hartman, G. L. eds., pp. 157-177. Wallingford: CAB International.

Jones J. B., Jackson, L. E., Balogh, B., Obradovic, A., Iriarte, F. B. & Momol, M. T. 2007. Bacteriophages for Plant Disease Control. Annu. Rev. Phytopathol. 45:245-62.

Kawasaki, T., Shimizu, M., Satsuma, H., Fujiwara, A., Fujie, M., Usami, S. & Yamada T. 2009. Genomic characterization of *Ralstonia solanacearum* phage φRSB1, a T7-like wide-host-range phage. *J. Bacteriol.* 191:422-427.

López, M. M. & Biosca, E. G. 2005. Potato bacterial wilt management: new prospects for an old problem. En: Bacterial wilt disease and the *Ralstonia solanacearum* species complex, Allen, C., Prior, P. & Hayward, A. C. eds., pp. 205-224. APS Press St. Paul, Minn.

Marco-Noales, E., Bertolini, E., Morente, C. & López M M. 2008. Integrated approach for detection of nonculturable cells of *Ralstonia solanacearum* in asymptomatic *Perlargonium* spp. cuttings. *Phytopathology* 98(8): 949-955.

McFeters, G. A. & LeChevallier, M. W. 2000. Chemical desinfection and injury of bacteria in water. En: Nonculturable microorganisms in the environment. Colwell R. R. & Grimes J. D: eds., pp 255-275. American Society for Microbiology Press, Washington, D.C.

Montesinos, E., Badosa, E., Bonaterra, A., Penalver, R. & López, M. M. 2008. Aplicación de la biotecnologia al control biológico de bacterias y hongos fitopatógenos. En: Herramientas biotecnologicas en fitopatología. 2008. Pallás, V., Escobar, C., Rodriguez-Palenzuela, P. & Marcos J. M. eds., pp. 317-343. Ediciones Mundi-Prensa.

Oliver, J D., Dagher, M. & Linden K. 2005. Induction of *Escherichia coli* and *Salmonella typhimurium* into the viable but nonculturable state following chlorination of wastewater. *J Water Health.* 3(3):249-57.

Pereira, C., Silva, Y J., Santos, A L., Cunha, A., Gomex, N. C. M. & Almeida, A. 2011. Bacteriophages with potential for inactivation of fish pathogenic bacteria: survival, host specificity and effect on bacterial community structure. *Mar. Drugs.* 9:2236-2255; doi:10.3390/md91112236.

Safni, I., Cleenwerck, I., De Vos, P., Fegan, M., Sly, L. & Kappler, U. 2014. Polyphasic taxonomic revision of the *Ralstonia solanacearum* species complex: proposal to emend the descriptions of *Ralstonia solanacearum* and *Ralstonia syzygii* and reclassify current *R. syzygii* strains as *Ralstonia syzygii* subsp. *syzygii* subsp. nov., *R. solanacearum* phylotype IV strains as *Ralstonia syzygii* subsp. *indonesiensis* subsp. nov., banana blood disease bacterium strains as *Ralstonia syzygii* subsp. *celebesensis* subsp. nov. and *R. solanacearum* phylotype I and III strains as *Ralstonia pseudosolanacearum* sp. nov. *Int. J. Syst. Evol. Microbiol.* 64:3087-3103.

Santander R. D., Catalá-Senent J. F., Marco-Noales, E. & Biosca, E. G. 2012. In planta recovery of Erwinia amylovora viable but nonculturable cells. *Trees.* 26 (1):75-82.

Yamada, T., Kawasaki, T., Nagata, S., Fujiwara, A., Usami S. & Fujie, M. 2007. New bacteriophages that infect the phytopathogen *Ralstonia solanacearum*. *Microbiology.* 153:2630-2639.

Yamada, T., Satoh, S., Ishikawa, H., Fujiwara, A., Kawasaki, T., Fujie, M. & Ogata, H. 2010. A jumbo phage infecting the phytopathogen *Ralstonia solanacearum* defines a new lineage of the Myoviridae family. *Virology.* 398(1):135-47.

---

The invention claimed is:

1. A composition capable of lysing cells of *R. solanacearum* comprising:
   a combination of bacteriophages comprised of:
   a) vRsoP-WF2 (SEQ ID NO: 1) and vRsoP-WM2 (SEQ ID NO: 2);
   b) vRsoP-WF2 (SEQ ID NO: 1) and vRsoP-WR2 (SEQ ID NO: 3);
   c) vRsoP-WM2 (SEQ ID NO: 2) and vRsoP-WR2 (SEQ ID NO: 3); or
   d) vRsoP-WF2 (SEQ ID NO: 1), vRsoP-WM2 (SEQ ID NO: 2), and vRsoP-WR2 (SEQ ID NO: 3).

2. The composition of claim 1 the concentration of at least one bacteriophage ranges from about $10^2$ to about $10^9$ plaque forming units per milliliter (PFU/mL).

3. The composition according to claim 1, wherein the concentration of at least one bacteriophage ranges from about $10^3$ to about $10^9$ PFU/mL.

4. The composition according to claim 1, wherein the concentration of at least one bacteriophage ranges from about $10^5$ to about $10^9$ PFU/mL.

5. The composition according to claim 2, wherein each of the bacteriophages of the combination is present in the same concentration.

6. The composition according to claim 1, comprising an agronomically acceptable carrier and/or excipient.

7. The composition according to claim 1, further comprising a chemical agent for the control of *R. solanacearum* or a biocontrol agent of *R. solanacearum* different from the at least one bacteriophage.

8. The composition according to claim 1, further comprising a biological control agent of *R. solanacearum* that is a lytic or lysogenic bacteriophage with activity against *R. solanacearum*.

9. A method of producing an irrigation water capable of lysing *R. solanacearum*, the method comprises:
   adding the composition of claim 1 to water to produce the irrigation water;

wherein the water is a natural watercourse, a channelled water stream, a natural water reservoir, an artificial water reservoir, or an irrigation water reservoir.

10. The method according to claim 9, further comprising maintaining the irrigation water in a reservoir at a temperature from 4° C. to 30° C.

11. The method according to claim 9, wherein the irrigation water pH ranges from 6.5 to 9.0.

12. A method for the treatment of *R. solanacearum*-contaminated soil, the method comprises:
adding the composition of claim 1 to water to produce an irrigation water; and
applying the irrigation water to the soil.

13. A method for preventing or treating wilt caused by *R. solanacearum* in a plant, the method comprising:
adding the composition of claim 1 to water to produce an irrigation water; and
applying the irrigation water to the plant.

14. The method according to claim 13, wherein the irrigation water pH ranges from 6.5 to 9.0.

15. The method according to claim 13, further comprising maintaining the irrigation water at a temperature from 4° C. to 30° C.

16. The method according to claim 13, wherein the watering occurs by an irrigation system that achieves partial or total flooding, drip irrigation, subsurface irrigation via perforated pipes, by exudation via porous pipes, or spray irrigation.

17. The method according to claim 16, wherein the irrigation system achieves partial flooding.

18. The method according to claim 13, wherein the plant is growing in a field, in a nursery, in a greenhouse, or in a hydroponic system.

19. The method according to claim 13, wherein the plant is a species belonging to the Solanaceae family and susceptible to and/or tolerant of *R. solanacearum* or any other species susceptible to and/or tolerant of *R. solanacearum*.

20. The method according to claim 19, wherein the plant is selected from the group consisting of a potato (*Solanum tuberosum*), a tomato (*Solanum lycopersicum*), a sweet pepper (*Capsicum annuum*), and an eggplant (*Solanum melongena*).

21. The method according to claim 13, further comprising prior to the watering step subjecting the plant to one or more other strategies selected from the group consisting of: chemical, physical, and/or biological control of *R. solanacearum* or other plant pathogens.

22. The method according to claim 13, further comprising applying a copper compound, an antibiotic, and/or a soil fumigant to the soil where the plant is growing.

* * * * *

SEQUENCE LISTING

```
<160> NUMBER OF SEQ ID NOS: 3

<210> SEQ ID NO 1
<211> LENGTH: 40591
<212> TYPE: DNA
<213> ORGANISM: T7-like viruses
<220> FEATURE:
<223> OTHER INFORMATION: /host="Ralstonia solanacearum"
      /isolate="vRsoP-WF2"
      /isolation_source="Tormes River, Salamanca, Spain"
      /note="Genome of the isolate vRsoP-WF2"

<400> SEQUENCE: 1
gacaactgat ggtgtccctg aagtgccccc ttaggggaa aacttccgac gcaaaaattt      60
gaaagcccca ctcgaaattc gacgcgggca gattcccccc gtgcccctc cgcggcccgg     120 ccctcgtggc ccctgccgac ccacctccgg gcaccctcca ggctgtacgc tccgctgact    180
cctggcacat cttctggcac actctgccgt aactccctga ttactaaggg gatgcactag    240
cttacgaagc tactgcgacc caataagcct cacgcatgag cactcactgg ctcactcgtg    300 gggcttttt ttctattctg tccccatttc cgcgccccc tgttcggcca tcagtttgct      360
ttggtttctc ctagggtttc ccctaagtgt ctccttggcg tgcatcgcta cgattctccc    420
aacggcccac ttgcggccca ccactggaga acatcatgca actgcaatac ttccgcgact    480
tggcaatcgg cacagcgttc actatcgctg gcacgcccta cgtgaagaaa agcgcacgga    540
ctgcgtacgc cgctcccggc caccctgggc attgggaagg ccgctggttc tggtttggtc    600
agactgaact ggtaatggcc taagggagca caccatgagc aaagtccgag cactcgccta    660
cttcttcgct gcaaccacgc tgcactcgc ctacgtgggc gcaagggcag cacatgcggc     720
catctcaagc ctcctcgtga tgcacctgca ttgatcccac tcagaacacc ctccttggcg    780
gcaaagccgc tacagaagcc tccagatcaa cgtctggggg cttttttgtt tgctcctggg    840
```

```
gctgacctac ctgcgtccca ctgcgtggct cctagggctt cctatcgttc cttcggagca    900
acgctcctga tatcggaact attgcagtga ttgaaaaata caattgggca gtctccgatg    960
tttcgtatgt aattcggtct caccaggggg acacgcccct gaagacaaaa agcgtggga   1020 ccggggcgga cgccagcagt cagggacaac ccgagtcaat ccaagagtaa gcacattgcg   1080
agtccttcca gtgtgctcat cactggagag acatcatgca atcattcacc ctgaacattg   1140
gccttatccc gagcaagaaa tcttcgcgta ccgctcgcat cactgcatcg gaagttaagg   1200
ccgcacttcg tggcgctggc ttcttcgtgt cgggctttcg catggcccag tcggccaccg   1260
agcctaccgc agtggtccgc gtgatcgcac gtcagccaat gagctatcac caagcgctct   1320
acaacgtgtc cctggcgctg gtgcaggact gcatcgcggt tgtccctgac acggtacggg   1380
gcgcgttgat tggcccggat gcggctgagt ggggtgagtt caatccggcc tacttcatcc   1440
cgtttgatgt cgaaccgcag gcaatcgctg cgtgacactt agggtgcccc ttcagggggct   1500 ccaggagtag ccgcattgcg ctgtgcagtg cgcctatcac tggaggacaa catgtacggg   1560
aactttgacc cgagcacgaa cgcatggccg ttcagtgtgg agtttgtgga cgctgtaggc   1620
tggcaagtgg aggacaaccg ggaccccacc aatgtcgtgg tgatggtcgc tggtctcacc   1680
ttcgaggaag ccaaacagcg cgcgtctgaa ctcaacctga accacttccg ggggtcctga   1740
catgccgact ctcaaggaag cgagcgtgaa tgctcagaga ccacgcggag gcgtccaagc   1800
gtggagcgta ggggacacct acccggtcac tgtagtgggc ctgggcaatg gcccccgcgt   1860
gcaatggtac gcggagaacc tgcacacggg cgaacgtggc cccgtgcgag atgcccaggg   1920
tgatgcagtg gtggaccagt atcgtctttg gcggagttc aacagaaatc gcctacaggc   1980
gtaattcggt ggccctgttc atgtgtcgtg aacagggctc caggagtgaa cgcattcaat   2040
cgtgagtgcg gtcatcactg gagaatgcaa catgcaaacg aaagaacagc gcatcgaact   2100
aatcgccgcg atgtttggtg agcaagaaac gggcctgatc ggtaagcaac tccgcgtgct   2160
ggataactcc caaagcgggg cgttctacaa tgttggtgat gtcggtaccg tagtcctcgt   2220
ggacgatgac ggtgaaatct gggtggactt tggcccggat ggcttcaaag gcgatggtac   2280 ggcataccg gtctgggccg ctggttcgct gggcgcagac gaccatgagt ttctggaaaa   2340
ctgacatggg cgtcatctgg cacgaactca tctacgccct gggagccctc gtggttgtcg   2400
gggtcctcat tctgatcctc accgagggag actgacatca tgcgcacctt tgcaatcgac   2460
ttcatgctca acggcaagcg cgttgggcgt gactacgtga cggcttccaa cgagaagcaa   2520
gccaccatca tcgcagaacg tactgcaccc gtgacgctgt atgacgaggt tgtggtcgca   2580
ccgctgtgat ggaccatcgg gctcccttat ggagccccca ggagtggacc ctttcaattc   2640
cgagagtgtc catcactgga gagaatcatg tcggacaaag ccaagcaatc catcgagttc   2700
gttcgcaacg gcctgggcga ggaaaacttc aacaagctcc tgagcatcac gggagtacgt   2760
gacatcgaac tggctgccgc gttcctggcg accaccaagg aggagcgtga ctctgtgaag   2820
acaggtgacg acctcatgcg cctgctgggc cgcaagcacg ctgagaaccg cgtggccatg   2880
gctctggtgc gcgcgggtgt gccggtggag gatgccgtgt ctttcgtgcg tgaaaccgct   2940
gcaagcctgt aagccccaag gtgcccctta ggggcctct aggagtgagc cgctggaatc   3000
gtccgaagtc tcatcactgg agatcgctat gtctgcacaa gccgaacaaa cccaaaccgc   3060
cccgaccatc atcgccctgc tgtctgctgc gaatatggct cagacgggcc ccggcgtctt   3120
cgctggcgtc atcaaccaag ccacacctga ggagcgcgcg ggtgtgaaga acatgaagga   3180
```

```
cctcctggcg ctgtacttca aggttcatgc gcgagtggtg gccgaaatct ccgcggaagt    3240
ggaagccacc acggaccatc gggctcctct ggtggacctg tccgacttcg ctgagaccct    3300
ggcggagtac ttcagccgtg ccgatgaagt ggtgccggaa ggcgtcacgc tgcaataacg    3360
ctgggtgccc cgaaaggggc tccaggagtg gatgtcttca ttgtgaggac ctccatcact    3420
ggagaaagca atggcacaga tgcgcgcctg ggtctacaag gcgcactgga ggcggcacct    3480
ggccgcgcaa ggcatcgtcc tgcgcaaata cgaggtggac aaggagtaca tgcaccgcgg    3540
catgacgcag gccatcttcc gccgcaacaa agcgaagttg gtggccgagt acacggagtt    3600
ctgacatgga catcgtagac gaactggaga taggaccctc ttacgccctg aactcggacg    3660
agaagtggct ccgcaagaga gccgctgagg aaatccgcag gctccgaaag caactggcgg    3720
acgctggttg ggctctcgaa gcggcccgtg aactcgaaga ccaacgagac aacgggggct    3780
ggctatgaaa cccgctgacg gtcaacccaa gcgcttcaag ctgcacacca gtatcccca    3840 caacaggtcc gagggtttga ctcatcggac caacaagggg accgcgcttc aagttctacc    3900
gaagaggtaa cgccatgaag atcactctga cactggagga caccgctgat ggtgtcgctg    3960
tgaactggac cgaggagcaa tctgaagctc agaacaaacc cagcgagagc ctggccacca    4020
tcatcgctgc caagttcatt cttgagataa atcaatctca ccgtatggga attttacggc    4080
tgtccggcac tgcattgggc gcagatcgcg catagctagt atgaggtgtg ttgcgtagag    4140
tgcgaaccag ttttatttgg ttcgccatgc ccgcatccag aagctcatcg caacagtaga    4200
ggagtagcaa tgccggtcat caaacgcggg aacaagtacc aggccagtgt gggctctggt    4260
actgatcgct ggcgcaagat gttcgacacc caggaggagg cggagaccgc agaactggca    4320
gagaagctgc gcaggaaggc cgctgggaag gacgagaagg gggctacaag ctccgcaaat    4380
ggggcgaagg tacagaagac cctaaaggag gcttacgacc gcaccttggc cctgatttgg    4440
aagggcaccg ctgcggagaa gacccacatc atcaactcga actccgtgat ggcggagttg    4500
ggcaaggaca cgctcctgtc cgacatcgcc accgaggacg taacggagat gatcctggct    4560
ctggaggaga agggcaactc aggcagcacg gtgaacaaga gctgtcctg cctgtccatg    4620 atcctcaaga ccgcctcgga tgagtggcct gggtgcatcg tggagatgcc caagctgaag    4680
cggcgcaagg agggggtctca ccggctccgg tggatcaacg aggccgagga gaagcggatg    4740
ctggaggccg cggagcacct ggggctctac gacctccggg actacatcat cgttggcatc    4800
gacaccgggt tccgccgcgg agaactcctc gggttccccc tgaaggacta ccagggcggt    4860
ctcatgatcc tccacgatgg tgagaccaag agcggcaagg ggcgcgccat cccggtcacc    4920
aagcgggtcc acgagatcat ccagcggagg agcaactact cgtacctctt ccaggactac    4980
acggtccaca gctgcgttg gcagttcgac caactgaagc tccacatggg gctccaggag    5040
gacacgcagt tcgtggtcca caccctgcgg cacacctgtg ccagccggat ggttcaacgt    5100
ggggtgcccc tgaaggtggt ccaggagtgg atgggtcacg ccaccatcgc cacgaccatg    5160
cgctacgcga agctagctcc gagcagcctg ctgatggcga agaaggccct ggaggaagaa    5220
ccccaggaac tcacattcat tcctcccccg cagatggatg tggtggggct tcacgacttc    5280
taaggaaagg aattggaaca cctcagagag acgttcaagg gaaaggtaca gagacaggca    5340
ggacgagatg ggtgctgggt ttggcaaggc tctaagacgg acagggata tgggaacctg    5400 tgggacccaa aaaccaagaa gcctgtctca gcacatcgac tgtcctacca actccacaag    5460
ggacaaatcc cggaggggtt gatggttctc caccggtgcg ataacagggc ttgtgtgaac    5520
ccaaagcacc tgtttgtggg gaccgcccag gacaatacgg ttgacatgta cctgaagggt    5580
```

-continued

```
agaggaacag ttccgcatta ggttccacat aaggataacc ctgaagggaa acctaatgtg    5640
taaatcctaa gtgtttatct tcatagatag acactattaa tgatatctac ttagagagaa    5700
cactttagtt gacactatga ctacccaaca agtggacaac gagaacgaag acctggtgac    5760
tattcagctt cgtctcgaag aagagatgac ccagcgggga gcagaccggt acatccgggg    5820
ggtatccaag gccatcgaga agggccgtga ggatgacacc gcctacggca agcaaatcct    5880
ggccgggagg ttggcgaagc tggcccaggc catcgctgag tggaaggcgg aggtggcctc    5940
tggtaagcct ggccggaagc actcggcctg gaagctcatc aaggacaagg acgacaacac    6000
cctcgccttc ctggccctca gcacgttcct ctcgggggtc tccgcagtcc gcaccgtcca    6060
gtacgtggcc gtggccatcg gcaccgcggt ggaggacgag atgcggttcg ccaaggtccg    6120
tgaggcggag cggaagaagt ttgagcagct agtcaccggg gcagcgaagc ggaccagcca    6180
gcactacaag cacgtctacg ccacccgcgt ggctgaggac gtgacggagt gggacaagtg    6240
gtcccggact gaccgcctcc acgtgggggt caagctcctg gacctcctga tgcagtccat    6300
cggcctggtg gaggtgtcca cgaacctgga caacagcgag cagggctcca gtacgtgaaa    6360
ggccctcccg gagaccctgg agtggatcga acggaagaac gaggtgaccg ccctgctgcg    6420
cccggtctat gagccgatgg tggttcagcc gcgggattgg accaacccgt tcgatggcgg    6480
ctacctgtcc tcgaacatca gccgctgaag ctggtgaagg acgaagaaca aggcgtacct    6540
ggaggaactc cgcggcgctg acatgcccat cgtctacgag gcagtgaacg ccatccagcg    6600
cacggcctgg cagatcaact cccaggttct cacggtgatg cggcacctgt gggactcagg    6660
ctccgagctt ggtggtcttc cccctcggga gggactgccg atgccaccga agccctacga    6720
catcgacacc aacgatgact cgaagaaggc gtaccgcatc gccgcagcga aggtccacat    6780
ggagaacctc tccattctgg gccagcgcat cggctttgac atggccctgg gcattgcggg    6840
ccgctacgag aagtaccggc gcatctactt cccgtaccag ttggacttcc ggggcgcat    6900 ctacgcggtc ccgcacctga acccgcaggg gtccgactac cagaaggctc tcctcagatt    6960
cgccaacggg aaaccgctgg gctccgaggg gtggaagtgg ttggccatcc acggtgcgaa    7020
cctggcgggc tatgacaagg tgagtttgga ggaccgcgtg gagtgggtcc tggagaacga    7080
agatgagatt ctcagaatcg caagtgatcc ctacgaccat cgtggttggg catcggaagt    7140 gggggggggtt aagatcgaca agccctggca gtttcttgcc ttctgctttg agtgggctgg    7200
gttcgttgag catggtgagt cgttcgtatc aaagctgccc gtggctatgg acggttcatg    7260
ctctggcatc cagcacttca gcgcgatgct ccggacgaa cgaggcgggg ccgcagtcaa    7320
cctcgtaccc caggacctcc cagccgatgt ctatagagcc gtcgctgaga gagtcattga    7380
acaggctgaa agtgatctcg ctcacggttc cgaggacgaa ctgaagcaca acggccaggg    7440
catcgcttac ctgtctgagg gctccaagac catcgcccag cagtggatca agttcggcat    7500
cacccgcaag gtcaccaagc ggagcgtgat gacgctggcc tacggctcca aggagtacgg    7560
cttcaaggag caactcatgg aggacatcct gtggccagcg aagagggcag cgatgcggcc    7620
tgatgggtcc atcgacacgg agaagttccc gttcagcggg gatggctacc gtgcggctct    7680
ctggatggcg aaggcaatct ggaacgcggt gaacgcagtc ctggtgaaag ctggcagagc    7740
gatgcgctgg ctccaggagg tggcagcact ggccgcgaag gaggaactgc ctgtccgctg    7800
gacaaccccg gtgggttcc cggtgatgca ggcgtatccg ccctggagg cacgtagggt    7860 gaagaccgcc atcaacggca tggtgctgaa gctcctcatg aaccaggaga aggactccct    7920
```

```
ggacaagcgg aagcaggggc agggcatctc gcccaacttc gtccactcct gcgatgcggc   7980
gcacctgatg ctcacggtgg tccgcgcgaa gcaggaaggt atccagaact tcgccatgat   8040
ccacgactcc ttcgggacca ccgcgggtga cgtggaggag atgtatcggg tggtccgcga   8100
gagcttcgtg gagatgtact ccgaggtgcg cgtcctggaa gacttccggg atgagatcgc   8160
ggagcaactt tccgagaagg cccaagcgaa gatgccgccg ctacccgagc gcggtctcct   8220
ggagttgtct cgcgtctgcg agagccgcta ttgctttgcc tgaacccttc cacatctgga   8280
agagttgagc cggggaacg attaggtgcc acacatggat aaaccagccg ccgttccccc   8340
ggtggcctct cccgagacaa ccgatggaac gcaacgaaca cgaagtatcg gaccagtacg   8400
agtccgcact tggccgcgcg attgctcagt ggcgcaccgg acggcccatc ccgatgacac   8460
tcgccgctga actgatgcaa cagggctatg acgtatccgc cctggaagcg cgtcacatga   8520
cctgaaccaa caatggcaga aagaaacaa cgcaacccga gcttcacctc gccgcgcggc   8580
atcgcccgct acccgccct caacaagccc gactacggca acgaacagtt cccgaagccg   8640
gatggtgagt acaaggtcca actcatcctg agcgaggccg aggcccagcc gctcatcgag   8700
aagctccagc cgctctatga cgcggccatc gaggaaggca aggcgaagtt caaggaactg   8760
aaggtggagc agcgcaagaa gctgggcgcg ctgaaggaga cgacctcta cgccaccgag   8820 tacgaccagg agaccgagga gccgaccggc aacctcatct tcaagttcac gatgcaggcc   8880
ggcggcaaga acaagaaggg tgagccgtgg tctcgcaagc ccgcgctgtt cgacgcgaag   8940
ggcaagccgc tgccgaagaa tgcaccggcc atctggggcg gttcggaagt caaggtctcg   9000
ttcgaggccg ctccgtactt catccccggc acgggtgctg ctggtctgaa gctgcgtctc   9060
caggcagcgc aggtgctcga actggtgact ggtggccagc gcagtgccga tgcctacggc   9120
ttcggtgccg aagacggcta cgaggcagac gacaacaatg aagagggcga tgaagccccg   9180
gacactgatg gcaagagcgg cagcggcgaa gacgagttct aaatcactga ctgccaaaca   9240
ggtggccctg aagtacggct tcaggagcgg cctggaagag aagatcgccg cggacctcac   9300
ctcgaaaggg gcggggttca cgtatgagga gctaaccatc ccttacgtga agcccgcgaa   9360
gccctcaaag tacacaccgg acttcgacct tctcaagaac ggcatcatcg tggagtccaa   9420
ggggcggttc ctaacagagg accgggccaa gcacctgctg gtgaaagccc agcacccaga   9480
cctggacatt cgtttcgttt tctcgaattc aaaggcaaag atcaacaagc gaagcccgac   9540
cacctatgcg atgtggtgcg agaaaaacgg cttcgcatat gcggacaaga gcgtgcccga   9600
ggcatggctc aaagagccgc cgaacctgga gtccctagca gccatcgaga ggctgcgggg   9660
agcatgacat ggcatacact tccaacacca agaagcgggc aagcacggac tacctggtgg   9720
tccattgctc cgcaacgaag ccctccgctg acatcggagc cgcggacatc gaccgctggc   9780
accggaagca ggggtggcgc tgcatcggct accacttcgt catccgccgt gatggcacca   9840
tcgaagaagg ccgttacgct gacgttatcg gcgcacacgt agaaggccac aacgagaact   9900
ccctgggcat ctgcctggcg ggtggtgtct ccgagaagga tgtgaacgtt gccgagaaca   9960
acttcacgcc cgagcagttc gccagcttac agaagctcct gacggacctc cgagcgaagt  10020
atcccaaggc caccatccag ggtcaccgcg atttccctgg tgtggcgaag tcgtgccctt  10080
ccttcagtgc gaaggattgg gccaagcaaa acggtttctg acgcaccacg aggagcaacc  10140
atgaaggcat ggcgtaaaga acccaatcag ggcgcagtcc gtattggtcg caagaccatc  10200
aacgcgaagg tgtgatgaa caagttcaaa ccgagcatgg tcaaccatgg ctccgtcctg  10260
tttcagcgga tgatgctcca ggccggtatc tgggcgctct aacctaaacc atctccagtg  10320
```

```
gtacttcggg ccggtccttc gggctggccc ccctttatg ctcaagattt gtaagaggtg   10380
cggtgaatgc aagccgttta gcgactttca caaagcaccc gcaggaaaat tcaagctcca   10440
gtcatattgc aagcagtgca agaaggaata cacgcgggac actggagcta acatcctacc   10500
ctccattcgt cagagagcac gaaagcaggg agtcccttc tcgcttacca agagaaacct    10560
cccacccatc cccgaagtgt gcccggtctt agggattccc cttcgacgga cactcggctt   10620
tgcggacgac aactcgccat cgctggatcg attgatccct gagcttgggt acgtgcctgg   10680
gaatgttgag tggatgagct accgagctaa tcgaatcaag aacgactcaa cctatgaaga   10740
actcgaaagg gtcactgcct gggtccgaga gcgagtttct acgacacatc ccatgtgagg   10800
gctgcggttc ctcagacggg aacagtctct tcagtgatgg gcaccagtgg tgcttcgtct   10860
gtgaaaccta cgtgcccggt gatggcagcg aaccaacaat aggaacaacg aagaagcgga   10920
tggaagggct gctaaccggg gagtttcgcc ccctactgaa acggaagatc accgaggaga   10980
cggcgcgcaa gttctcgtat caagtcggtg agttcaaggg aaagacggtg caactcgcgc   11040
cgtactttga caatgcaggt gtgatggtgg ctcagaaggt ccgattcccg gacaaggagt   11100
tcaccgtagt tggggatggc aaggccatct ctggaatcct cttggccag aacctatggg    11160 ctcctggcgg aaagaagatc gtggtcaccg aaggcgagat cgatgccatg tcggtgagcc   11220
aagcgcaggg caacaaatgg cctgtggtct ccgtaccaaa cggagcacaa ggcgcgaaga   11280
agtcgcttca gaaggcactc gaatacctgg agagctttga tgaagtgatt ttgatgttcg   11340
attccgatga tgcaggcaag aaggccgcta ctgagtgcgc ggagttgttc tcgcccggca   11400
agtgcaagat cgcgtccatc ccgatgaagg acgccaacga attgctgaag gctggccgtg   11460
agcaggagat catcactgca atctggcagg ccaaggagta ccgccccgat ggcatcatct   11520
cgggagcgga actgtgggag gcggtgtcag catctcagga tatcgtagag tccgttccgt   11580 accccctggga cgcactgaat gaagtcacga aaggcgcgcg tacaggcgag cttgtgactc   11640
tcactgcggg ttccggcatc ggcaaatctg ccgtggtacg cgagatcgct caccacctcc   11700
tgaggcgtgg agagacggtt ggcatgttga tgctcgaaga gaacccgaag cgcaccgcgc   11760
tgggtctcat tagcatctcc ctcaacaggc ctctccacat agaccgtgaa ggtgtcagca   11820
aggatcaact gaaggtagct ttcgatgata cggtaggctc tggccgacta ttcctctacg   11880
accacttcgg ctccagcgac atcgacaacc tggtgtcccg tgtccgcttc atggcgaagg   11940
gcctggggtg caagtgggtc atcctcgacc acctgagcat tgttgtctct ggcctcggtg   12000
acggagacga acggcgactc atcgacaacg caatgacgat gctgcgtacc ctcgtggagg   12060
agaccggcat cggcatgttt gtggtgtcac acctccgccg accggagggt gaccgcggcc   12120
acgaacaggg agcacgtacc tcgctcaccc aactccgcgg ttcccatagc atcgcgcaac   12180
tgtcggacat ggtgattggt ctcgaacgga accagcaggg tgagaacccg aacgtcacca   12240
cgctccgtgt gctgaagaac cgcttctccg gtgagaccgg tgaggccggg ttcctgctgt   12300
acgaccggga gaccggacgc ctggaagaga cggacgcacc tgctgcgccc ttcaaagacg   12360
aaaccaaatc ggacgttcag tccgagttct aaccaaaggt tacatcatga gtctgatttc   12420
gctgttcacg cagtccgctg ctgaccaacg tgctgccgcg ccccgtgctg cccgtgtccg   12480
cgccaagatc gcggacctga tcgactaagc gggagtctct gtgatcgatg acacccgcct   12540
ccaagagttc cgagaaatcc tcgatgtagt ccgctgggag ttccccggtt cacaccccgt   12600
gattgggggc ggggctctcc gcgattccta ccatggtcgc ccaatcaagg acgtggacgt   12660
```

```
gttcatgcgc aggcgtgacc acgagacgct gaactcggaa ctcacccgct tcatccgccc    12720
gccgatcctc gtggcccacg gctatggccg tcccgacatg cacggcgcat gggacctgat    12780
gcagtccgtt gctggctacg aggtgcaact catcctcgcg gacttcgaga acctggaaga    12840
cctggccggt acgttcgacc tggggattgc ccgagccacc ttcgatggtg accggctgtt    12900
cctccacccg gacttcctcc aggactccac ggataaggtc ttccgcatcc gtcgcgcgga    12960
caacctgttc gagaaggcgc gaagcctgaa gcgcatcaag cggctggcag agaagtaccc    13020
ggacttttca acaccggact cgagcattg ccctgtctgc gcacaaccca tcatcgagtt    13080
ccgcaacgct gccagcgtcc gagagcacca aatctccggg ctctgccagc aatgccagta    13140
ctcggtgttc gacaaggact gaccatgaac accttcctca ttctcctggt cctcatcgga    13200
ggccaaatcg aaggccgcgt gatcgctgag ttcgacactc cccgtgagtg cgaagcagcg    13260
aaggaacacg tgagggtcat caaccaaccc cctgtcgtcg cgtccacgtt ggtgtgcgca    13320
agggatggcc gcgcgtaatc accaaggacg gtatgaagct attcgacatt gaaacaaacg    13380
gtctgctgga taccgtcacc aaggttcact gtctcgtcat caaggatcgc accaccggga    13440
ggaagttccg ctgcatcccc gcaggcttcc cgatgcaagc ggacatgacc atcgagcaag    13500
ggctggggct tctcaagtcc ggccccatcg gtggccacgg aatcctcagg tacgacatcc    13560
cggtcctgga gaagctgtac ccggacttca cctacgacaa ggaccaggtg ttcgacaccc    13620
tggtggccgc gcgtctcatc tggacgcaca tcaaggacat cgacaacggg ctcctcaaaa    13680
agaagcaaat ccccggctcc ctctacggct cccactcgct ggaagcctgg ggttaccgcc    13740
tgaagctcca aagggcgag tacgcggctg agttcaaggc gcgcatgggg gacgcttacg    13800
aggggggcat ggagtggcga gagctttctc ctgagatgct cgactactgc gacctggacg    13860
tggatgtcac ggacgcactg ttcgaccgga tcgaaggcaa gaactactcc gcggaggcgc    13920
tggagcttga gcaccgcatc gcctggctga tggctcaaca ggaacgcaat gggttcccgt    13980
ttgacgtgac gaaggccagc gcgttgtacg ccaagctcgc gcaacgccgg ggcgaactgg    14040
agcgagaact gaaagagttc ttccgttct ggttcgctcc ggctggaaca gtgactccga    14100
aggttggaaa caaggcgcga ggaactgtag ccggtgtccc gtacaccaag gtgaagatcg    14160
tggagttcaa ccccggctcc cgcgaccaca tcgctaatcg ccttgtcacg ctctacggct    14220
ggaaaccgga ggtgttcacc gatggcgta agcctcgggt tgatgaagat gtgatggcac    14280
gcctggacta cccgcccacg aaactcctca cggaatacct gctggtctcc aagagaatct    14340
ctcagctagc tgaaggtgac caagcgtggc tcaaggttgt acgtgacgga agattcatg    14400 gctccgtgaa tccgaatggc gcggttacag gaagatgcac gcacgctttc ccgaacgtgg    14460
cccaggtgcc agccgtaggt tcccctatg gtgaggagtg ccggggattg ttcggggcac    14520
ctaagggttg gctgctggtt ggctccgatg cttccgggtt ggagcttcgc tgtctagccc    14580
acttcatggc caggcacgat ggcggcaagt atggaaaggt gatccttgag ggagacatcc    14640
acacggagaa tcagaaggcc gctggactgc ccacacgaaa caacgcgaag accttcatct    14700
acgcgttcct ctacggagcc ggggacgcca agattggtaa gatcgttggt aaggacgctg    14760
ctgaaggaaa aagctcaag gccgcgttcc tgaagaagac cccgcactc aagaagctcc    14820 tcgaagctgt ccgtgagtct gccaagcgcg gctacctggt tggcctcgac aagcgacaac    14880
tccatgtccg ctctcagcac gccgcattga acaccctgct gcaatccgca ggtgccctca    14940
tctgcaagta tttgggttgtc cgcacggcag agcgaatgga agctctgggc tacaagcacg    15000
gatgggatgg ggacttcgcg ttcgtcgcct atatccacga tgagcagcag gttgcagtac    15060
```

```
gaaatgagga agtcgccaag gtcctcgttg agcaggttgc attggccatg aaggacgccg   15120
aagcgtgggc cggattccgg tgcccgctgg cctgtgagtc caaggtcggt acggattggg   15180
cttcaacaca ctaaagtaat cagacaccaa catgagcatg ttccgagacg acctactcaa   15240
agaagtcctc tacgaggcgt tcaagactcc cttcaagctc cagtccgact tcgcccgaga   15300
gttcgctcag gaagtcgccg ctctggcctc gatgggatac atctcgacct acgaggggcc   15360
gcagcagttc ggcaagaagt ggcgcgtcac cggcatcggc ctggacaagc tgcgcaagct   15420
ggggatgctg tgagtgaagc cctacgcccc cattcgctga ggatcatggg ccggaagttc   15480
cgggtctctt acaaggatga cctggacggt gacctgggat actgcgaacc caccaagtgt   15540
aagatcgaga ttgagaacgg gcagcacccc gtggaggagg ccgatacggt cctccatgag   15600
gtgcttcacg cggtgttcta tctgatggac attgggctct ccgcggagga ggaggagcac   15660
gtggtccgta aggttgtcac cggactcacc caggtattcc aggacaaccc ccggctcctg   15720
acctacttgg caaacgccaa gtgatggacc atatagccaa gtttgattct ctccaggagg   15780
aactcatgac ggacaagaag tggaccatca cggttaacgt ggacaccccc gagggccacc   15840
gggagcggac catcgagttc ccccaccggc ccaccgagga ggagcttggt ctcaagctgg   15900
cgcagttctt cagccggatg aacttccgat tcaacgaaca cctgaaggag gtgaaggggt   15960
gtgcgctcct gacacctcgg agaccgtatg aaagtagcgc tgattgatgc tgacgttctg   16020
gtcttccagg cggctgtagt cgctgagaag gcaaccgatt ggggggacgg tgtttggacc   16080
ctccacgcag acgagggtga cggagaacga atcgttcgcc agtccgtcat caccctccag   16140
gagaagaccg gtgcggataa ggtcatcctg gcattctccg atgaggagaa ctggcgcaag   16200
gccatactgc ccacctacaa ggccaaccga gcgggttccc gccagccgat catccgcgcg   16260
catctgaagc ggtgggcttc cgacgaatac gagagcttca cccggccaac cctcgaaggg   16320
gatgacgtgc tgggcatcct ggccacccgc gagggcaagc caggcgagaa cttcatcgtg   16380
tgctccatcg acaaggacat gcgaaccatc cctggcaccc acttcaactt cggcaagaac   16440
gaagagttcg tggtgacgga ggaggggggca gactactggc atctcttcca gaccctcacg   16500
ggtgacccgg tggatggcta cgcaggctgt cccggcattg gccggtggc cgcgaagaag   16560 attctcgaca gagcccccac ctggggtgcc gtggtctctg cctacgacaa ggcaggcttc   16620
ggtgaagagg aagctctcgt gcaggcccga gtggcgcgca tctgccgcgc tgaagactac   16680
gacttcaaga agaaacaagt tcgactgtgg accccaaaga aatcctgaaa gaactggaac   16740
agcagcaacg ccgcaagttc gagaaaggcc ctctcaccgg caaacgcgcc gatgtcatca   16800
tcatggacga catccaggac accaaggaca ccaacccgaa ggacgccatc ggctccacca   16860
agctccccct cgacctcgtt cctgactcgc tctcggtctt cgccgcgctg cgttcaccg   16920 agggtgccac caagtacggt gcctacaact ggcgtgtcgc tggtgtccgt gcgtccatct   16980
acaaggccgc gctggagcgt cacctgaaga agtggtggaa cggtgagtgg gccgacccga   17040
agacgaaggt gccgcacctg ccagcgtca tcgcgtgtgc tgcgatcatc ctggacgcgg   17100
acctcgcagg caagttgacg gatgaccgcc ctccggcaat cgacctgagt tccttcatcg   17160
actcccttga ggagaccgtg aagcacctca aggaactgca caaggacaag aacccgaagc   17220
actacaccga actcaacgta tgaacccgaa gcgaaacact ctgaccggct gggtcatcta   17280
tgatgcagag cggcgactg gccgaagcac cgcgattgcg ctgagtcttc taggcaaggc   17340
cattgcaaat ccaggtgtgg ccgtacaaat ccgagaacat cacggtactc gtccggctga   17400
```

```
cgagagtctg atgcgcctga tgcgggatat ggtctttcgg ctgggcctca agggcatgac      17460
gttcagccag aacctgactg tgacgttcaa cctttgggag cctgtgtgag ccagagccga      17520
aagggctctc tcattgaggc cctcatcaac accgcaatcg gcttcgggat caacttcacg      17580
gcgaacctca tcatcctccc actgttcggc ttcaccagtt tgacggtgca gacgaacctg      17640
gtgattggcg tggtctacac gctcatctcc gtggtgcgga gttacgtggt tcgccgctgg      17700
ttcaacgcac acatcgtccg agccgccaag aaactctcag gggcctgaag gtctcttttag     17760 gttccacaat aggagaatca aattggcgaa cgacaagttt ccgccgattc ccaaagaatt      17820
acttgaggcg cttgagaagc ggttcccgga gacaccactc gaaaatatcg ggtctgtgga      17880
tcaacttcga ttggctcagg gtgagctacg tgttgtccgg tttctccgag cccaattcga      17940
gaagcagacc aagaacattt tggagaacac atagtgtgca tgtctcaacc gtccgcccca      18000
cctccggccc caccgccacc gccacctccg ccccgcccg ttgatccgat tccggtccaa       18060
cctgcgcagc aaaccggtgg agcggtgacc agcggcaaga gcaagggacg cgactccctc      18120
cgtatcgacc tggcccagaa gacatcgggt ggtggcgccg gtctgaacat cccgatgtaa      18180
cgaagggcag ggatggaaca agaaaagaaa acctgcgcct ccctctacca gaaactcacc      18240
accgaccgag acccgttcct gaagcgggcc tacgactgcg ccgaactgac gattccctcc      18300
ttgcttcctc gtgagggaca caacggctcc accaaactcg tcactccgtg gcagggcatt      18360
ggtgctcgtg gggtgaacaa cctcgcatcc aaactcctgc tgacgcagct tcctcccgga      18420
actcctccgt tcaagttgtc gattgacgac ttcacgctgg aggaactgac gaagcaggaa      18480
gggatgcggg cgaaggtaga ggaggggctc aacaagatcg aacgcgcggt tcagactgag      18540
atcgaagcga actacatccg cgtggctgcc ttcgaggcgc tgaagcatct catcgttagt      18600
ggcaatgccc tgctgtacat tccgcctgaa ggtggactga gagtattcca cctgaccgc       18660 tacgttgtcc gccgtgaccc gatgggcaac gtgctggaca tcatcaccaa ggagaacgtc      18720
tcccgagacg cactccccga caacctcgtc ctccctgatg acaccgagga gaaccaggag      18780
cccgcggctg gtacgaagga tgtggagctt tacacccacg tctatcgcca gggccgcagg      18840
tggaaggtct accaggaagt caagggtgtc cgcattcccg gcaccgaggg ttcgtacccg      18900
ctcgataaga gcccgtggat tcccgttcgc ttcacgcaga tcgacggtga gagctacgga      18960
cgcggttacg tggaggagta catcggggac ctgaagagtc tcgaaggact ctcccaggcc      19020
atcgttgagg gctccgctgc cgcagcgaag atcctgttcc tggtgaaccc gaatggcacc      19080
acggacatgg ctgacgtgtc cgaggctgag aacggtgcgt tccgcgaggg tgtcgcaact      19140
gacatcacgg tcctccagct tcagaagcac aatgacttcc gcgttgctct ggagaccatg      19200
aaggacatca ccgagcgcct ggcgtttgca ttcctgctga actccgcagt gcagcgcaac      19260
ggcgaacggg tgaccgcaga agaagtccgc tacatggcga acgagttgga gtctgcgctg      19320
ggtggtatct actccatcct ctcgcaagag ttccaactgc cgctcatcaa gcggatcatg      19380
taccagatgg aacggcagaa gcgtctgccc gtccttcccg aagggaccgt caagccaatc      19440
atcgtgactg gcatcgaggc cctcggacgt ggaaacgacc tgaacaagct gatccagttc      19500
gtccagatcc ccgcacaggc agcgaatctt cctcccgaga tcgacaaggc cgacttcctc      19560
aagcgtgctg gtacggcgct ggggatcgac atgaagggtc tcgtgttgcc gcctgaggtg      19620
gtagctcaga acaaccagca ggccatgatg atgcagatga tgcagcaggg tgtgaacccc      19680
gccatcacgc aggctggaca gctaatgaaa caaggaatgc agaatgccgc gcaacccgca      19740
ggcgggcagt aaggctcccg aggccaacac tgccgaagcc cccgtggtca ccgttgaaga      19800
```

```
ctcggtggcc gaacagcaac ccaagcccgc agcgaagccg gtcaaagtga ccgaactacc   19860
tggtggcgtg aagatcgaag acttctgatg agtgtggatt ccgtagtcat caagcagccg   19920
gacgctccgg tggaagacca ggcccacatc gatgcgatgg tggccaaggt ggatgctgcc   19980
aatacttcga ccgaaccgga cactcccggg gtgcccgcag agggacgccc gcagtggctc   20040
ccggagaagt tcaagtctcc cgaggacttg gccaaggcat atgccgaact ggaaggcaag   20100
ctgggtggga agaaggatga tgccactcca cccgctgacg acaaggccgc gaagtctgac   20160
gaaaccccgg acccaagcaa ggccacccag gacgatgcct cgaaggctct ctctgagaag   20220
ggcctgagct tcgatgagtt ctccgctgag tttgcccaga agggtgaact gaccgccgag   20280
agctacgaga agctggagaa ggctggcatc ccgaaggccg tggtggacca gtacatcgct   20340
ggccagcagg ccctcgctga gtcgtaccgc aaggacgtga cctcggttgc cggtggcgat   20400
gaaagcttcg ctgagatggt cacatgggcc gctgcgaacc tctcgaagga ggagatcgcc   20460
gcgtacaaca aggccgtgga ctccggtgac atcaaccagg cgaagctggt cgtggccggt   20520
gtgtaccaga agttcgacgc tgctggccgc ggtggtgagc ctgccctggt gactggcgct   20580
ggcggtaagg tctcgggcga tgtctatgag tccctggctc agatgcagaa ggacatggcc   20640
tcgccggagt acaagaccga ccccgcattc cgcaagaagg tggagcagaa gatcgcccgc   20700
tcgaacatct tgtaaggaac catcatgatc ctggagagca tcctgggttc ggtggtggtc   20760
cccgctatca tcgacctcgt gaagggtgct ggtggggcca ttagccgcaa gttctttggt   20820
ctgtcggttg acgaccagat caagattcaa aatgccgaca tcgagaagct caaggctctc   20880
gctgccctcg acaatccgta tggcaccccc agccagtggg tggtggacct ccgcgcatcg   20940
ttccgataca tcggcgctgc cgcggtcatc gctgtcggct gtgtcaccct gtatgccggt   21000
gtccagacca acatcgaaga cgtgaaggag atgggtttcg ccctcgtggg catgcccttc   21060
ggtttcatct tcggtgaacg cctgtacctc ggcctgaggg gcaagagcaa gtaagcactg   21120
ccgggaagca gcgcattctg tacggttctg atcccgtaac cgttacccac gggatcacac   21180
tgccattgaa gtgaaaggtc ctagccgcac tgcgctcctg cgcggtggct ctgctgcatc   21240
caaagaacac cacaacagaa ccttggcccg ctgaggcgga caaccctgtg tgacgtgtga   21300
gttcccggaa ccgctcaac acgactttca actcacttcc aaaacaaaaa tggcaaacgc   21360
agttccgtct cgcctgggcc aggcaaacct ggcaggcgat ccgaaggccc tgttcctgaa   21420
ggtcttcgct ggcgaagtca tgacggcctt cgctgaaaac aacatcgtac ttcagtacgt   21480
ccgccagcgc acgattagtt ctggcaagtc ggcttgaccc aaccttatga actgggccga   21540
ctctaaacac cccgtaaatt cggtggaacc ccatgggggc aataccgagc caagacttcg   21600
cagtacgcga gatggtgtag agactagaca cggggaaccc acaaagacct gcgcatgttg   21660
caacgtcgag aagcccgccc gtgagttcta taaaaaggac gcacagacag gaaggctcga   21720
tggaatttgc aagtcctgcc gaatcatcaa gacccgagag aaaaacttag gggtcactga   21780
agatgactat cggcggatgt atcatgtcca gggcggtcga tgtggaatct gccaacggcg   21840
cttgtactca aagaggtaca agagtttgc agtggaccat gatcacgaga caggaaaagt   21900
ccgtggcttg ttgtgccata attgcaaccg cggattaggc atgttccgag acgacctgac   21960
tgcgcttagg cgtgctatcg actgggttaa ggtatagtcc gatcctcaca gcaatgtgag   22020 tagggggaagc agttccccgt aattggtaag gctaccgccg cgtaccacac gcccggtaac   22080
gaaatcaacg gcagcaacat cgcccacaac gaagtggtca tcaccatcga tgacctgctg   22140
```

| | |
|---|---|
| ctggccaaca ccttcatcgc caacatcgat gaagcgatga accactacga tgttcgttcg | 22200 |
| gtctattcga gcgaactcgg caaggccctg gccaaccagc ttgaccgcca cctgctgcaa | 22260 |
| ctggctgtcc tggccgcccg ctctgctgcc cgtatcacgg gcgaacaggg tggttcggtc | 22320 |
| atcaccgatg ctgctgccgg taccgactcg aacgcactgg tcgcggacat cttctccgcg | 22380 |
| gctcagaagc tcgatgagaa ggatgtcccg gctgatggcc gtgtgtgctt cctgcttccg | 22440 |
| gcccaatact acgccctggc acagaacacc aagattctga acaaggattg ggtggtgcc | 22500 |
| ggtgtgtatg cggatggcaa ggtcctccgt gtggccggtg tggagatcgt gaagacgaac | 22560 |
| cacctgccga acacgaacat cgcttcgggt tcgaccgcgg ctggtactgg cgataagtac | 22620 |
| attggcaact tcacgaccac cgttggtgtg gtcacccaga agtccgccct gggcaccgtg | 22680 |
| aagctcatgg acctggcgat ggagtctgaa taccagattc agcgtcaggg caccctgatg | 22740 |
| gtcgccaagt acgcaatggg tcacggcgtt ctggctccgc aagcggctgt cgaaatcaag | 22800 |
| accgcataag cgtcccctca agcctcggga ggttctcttc aagagttcct cctggggctt | 22860 |
| tttttctgc tctcaaggat caccaattgg caaccaagac tcaaactgat cgcgccaagg | 22920 |
| acggtcagga tttcttccag cttccggcct acaaggacac gcccacggtc accgtgaatg | 22980 |
| gcaccgcccg tgctcgcacg actgtcccga gtggcgtcca gctggcaacc cctgcggctc | 23040 |
| aggatgacat cgtagcgatc acgttcaact cggctgaccc tgggaatacc cgccgcgagg | 23100 |
| tcttcacccc ggccactggc gcaaccatca caccaccga ttctgcatc gaggcccgca | 23160 |
| ttgtacccgc aggcaccatt gcggccctca ccatcaccct cccccgaac ccctcgaagg | 23220 |
| aaggccagca gttccgtgct gtcaccacgc agaccatcac cgcggtgacc tggactggtg | 23280 |
| gctctcgtct caacgctccc accacgctag ccgctggccg tgctgccacc ttcgagtgga | 23340 |
| gcgtggcgaa gcaggagtgg gtcttcatca actaaggaaa acgcatgacc accatcgtca | 23400 |
| ctccgaccac ggagcttgag gcggtcaacc tgatgctcga tgtcatcggg gagagcccaa | 23460 |
| tcagcaccct ggagaacagc gctgtggtgg acgcggtgaa ggccaaggcg gtcctctccg | 23520 |
| aggtgtcccg cgctgtacaa acgaagggct ggcacttcaa caccgagaag gggttcgagc | 23580 |
| tagtccccac ggtcttcgag aaggagatca tcgtccccgc caactgcctg cgcattgata | 23640 |
| cggtctaccc ggacgagggc atcgatgcag ttcaccgtgg cactcgcctc tatgaccgcc | 23700 |
| gcaggcacac ctaccagttc gacaagagtg tgaaggtgga catggtggtc aacctccaat | 23760 |
| tcgaggaact cccggaatcc gcccgccgct acatcgccat ccgtgccgca cgggtcttcc | 23820 |
| aggcccgcat agtgggctct gagagcctct accagttcac cgcagaggac gagagggacg | 23880 |
| cccgagcgga cctcaagaag gctgagggca tcacggggga ctacaacatt ctgacggaca | 23940 |
| gctgggctgt tcgtcgcgtc atcgatcgct gatatgcccc tcgtttcttc ttccatcgcc | 24000 |
| aacatggtga acggggtctc tcagcaaccc ttcacgctgc gtctcgcgtc tcaagctgag | 24060 |
| ttgcaggaga acggcctcag taccgtggct caggggttga agaagaggcc cccaaccaag | 24120 |
| cacatcaaac gcctcggcag tgccatcacc ggctctgcct acatccacac catcaaccgt | 24180 |
| gactctgtgg agcggtatga ggtggtcatc acgaacggtg acctgaaggt ctacgacacg | 24240 |
| gcagggaacc agaagacggt gaacttcccg aatgggaagg cgtacctgaa ctccacggac | 24300 |
| cctgctacgt ccttcagggc cgtcactgtg gcggactaca cgtttatcgt gaacaagaag | 24360 |
| actgtcaccg cggccagtgc cacgaactcc ccaacgcggc ccttcgagtc cctcgcaaac | 24420 |
| gtgaaggttg ggctctactc gaagacctac accatcaccg tctccggtgt gggcacggcc | 24480 |
| acctatagta cccccgatgg caccgttgcg gcccacgcgg cacagatcac cacggactac | 24540 |

```
atcgccaacc agcttgcgaa tggtctcatt accctcggtg gattcacctc agtgaaccag   24600
gtgggctccg tcatctacat cgcccggccc accgattaca ccatctccgc aacagatggg   24660
tataacaacg cggccctgaa cgtgattaag gggacggtgc agaggttctc ggaccttccc   24720
gcgaatgcga acttccagga cttcactgtg gagatcgcag gggacaacac ctcggagtcc   24780
gataactatt gggtcaagtt tgacaagacc gggaacaact ccggtgtctg gcgcgagacc   24840
atcaagccag gcatctcggt tggtcttagt cccagcacga tgccgtgggt actggtccgt   24900
gagtcggacg gcacgttcac cttcaaaccc atctcctgga cgaaccggct ggtgggtgat   24960
gaagactccg ctccacaccc atcgtttgtg gccgcacca tccaggatgt gttcttctac   25020
cggaaccgcc tgggcttcat cgcggatgag gctgtggtga tgtcggaggc tggccagttc   25080
ttcaacttct acccgaccac ggtgacgcaa ctcctggatt ccgaccgcat cgacgtatca   25140
gcatcccaca cgaaagtctc gaacctgaac ttcgcggtgg ccttcaacaa ggacctcctg   25200
ctgttctcct cgcagactca gttctcggtg gaatcaggtg acctcctgac acccaagagc   25260
gtctccatca agcccaccac ggagttcgag tgcagcaccc ttgcgcctcc cgttgggatt   25320
ggacgcaacg tctacttcgc ggtccctaag ggtgagttcg agggcttccg tgagttctac   25380
gtagcggaca acgcaggcac caatgatgcg gctgagatca ccggccacgt cccgaagtac   25440
atcccgaagg gggcctacaa gatcgctgcg gctctcaacg aggacttctt cgtggtgctg   25500
acttcagggg aacccaacgc gatgtatgcg tacaagttct actggaacag caacgagaag   25560
ctccaaagct cctggtccaa gtggaccttc ccgagcacgg acacgattct ccacgcggag   25620
ttcatccagt cggaactgtt catcctcatc aaccggcccg atggtctcta cctggagaag   25680
ctcagtgtgg ctctcgggga catcgggacg aacgagccct acaacgtcca cctgaccgc   25740 aagctgacgg tgccgaaagc aagcctcacg tatgacggca cgtacaccat catctcctcc   25800
gcggctctcc cgtggaaccc aacggatgga acgtacacgg cagtggtggc caccagtcag   25860
ccgcagaagg ctggcgtcct ctacccggtc atttgggatg ggacgaacgc caagattctc   25920
ggtaaccgtg tggactccga cctcatcgtt ggtaggcgct acgccttccg ctatcgcttc   25980
tcgccgctac tggtccgcca gcagtccggc cagggccaga aggcggacac ggttgcacgt   26040
ctccagattc gcaacatgca agtcaacttc tcggagagtg gcaacttcca ggcaaaggtc   26100
acgccttacg ggcgggacac ctacacgtac acctactcag gaaagaccct cgggctgcct   26160
tcggcaaaca tcggggccat cggaattgaa gatggcaagt tccggttccc ggtgatgtcg   26220
cagaacacca ccgtggacat cgaactcttc tcggactcgc cgctcccctg cgccttcttg   26280
agtgcagatt gggaaggcta ctatgtccga cgaagccagg cggtctaaac catacgtccg   26340
tcctgcaaca cgcgaagact gcatcatcct cgcaaggaac ctccgacagg aagacgcgga   26400
ggagatcgct catgtgaacg gtctccccgc ggagatgaat ctcttgctgg ggttccgcac   26460
ctccgctcga ctttatgcgg tggtgtgggg ggatgagacc gtggccgtgt cggcatcgg   26520 gggagtgcct ggcgtcatcg gcttccctg gatgctcgct tcgccctccc tctcgaaaat   26580
ccgcaagagc ttcctgaggg agtgccgcgg gtacgtggag gggatgctcc aggagtatcg   26640
ccacctggag aactacgtgt gggcaaagaa cgaagtccac atccagtggc tcaagtggct   26700
ggggttcgag ttcgagccag cagcaccatt cggtatcaat gacgaaccct tcacagatt   26760 ttataggagc atgtgatgtg cggaccagcc gcagttccaa tcgccatgct gggtatcagc   26820
gctgtgggca ctgccgcttc gattagcgcg cagtcgcagc agcagaaggc acaggatgcc   26880
```

```
ttcaaccagc gccagtatga aaacgacatg accgcgtacc gaggcaacct cgccaacatc    26940
gaggtgcaac ggaaccaggc gcgggaagat gcagtagcgc agaagcagca gaacgacatg    27000
gcaggaaggc gcgcaacagc aaccgccacg actgccgcag gtgaggcggg tgtctcaggc    27060
gcctcggtgg atgcactgct gcgggacctc gctggccagg ctgcctacga caacaccaac    27120
gtggatgaga actatctgcg ccaggacagg gctctgaacg cccagcgtga aacgccttc     27180 aacagcactg caagccagat caaccagctt cgcccctcga tgtccccgga ctatctcggc    27240
gctggtctcc gcattggcca ggctgctgcg ggtgcttaca gccagtacca gcagaacctc    27300
gactacgagc ggaaccagag cgtcccacgc cgaggagcat aaatggcacg agttcagaca    27360
gactatcgaa cccgaggtac agggcttcag acatctcgt ccccaatgct tcagccgcag    27420
caggcagggt tagacaatgg tgccgctgag tctgccgcac ggctggccca ggcgttgggg    27480
gctgttgacc tgtctccgct ggtaaccgcc aagcgatacc aggatgtgga ggaggcggag    27540
aaggcacggg cctacgccaa ctccctcacc gtggaggagc ttgggaagca gatcaaggat    27600
gggaccctca tggcgtccca ttcgcctgtc ttcagggcaa cggtcgaaca catccacggt    27660
gagaacacgc tcaacacgtt cgagcgggac acactctcga agctcacccg cggggaactg    27720
aagttcgaca ccccgcaggc catggatgag tacctcacga agtaccgcaa cgaggccctc    27780
acgggatcca gcaagttcac cactgcgggc ttcgataagg gctacggcac gttccgtgag    27840
cgagccatcg cggttaacgt gaaggtggcc gatgaagagg ccgtgaagcg cggcagccag    27900
gaggcctcgg acaacctcgg caacctgacc ctgcaagtca ccgacccgat gtacaagggt    27960
gacgctgcgc aggccatcgt ggaccgctac cagcttcttc ggaagacctc tctgctgcgt    28020
gacgatgccg cgaaggaagc tctctcgggt gtcgctgcga accttgcagc ctccggcaac    28080
aaggccctcc tgggttctct gctggacaag aagttggaca gcggtgtctc cgtcaaggcc    28140
gctttggggg acctgaaggc catccagttc acgcaacacg ctgaacgtga gtatgaccag    28200
gcgcagcacc aacggattga cgttgagatt cgtccgttcg tggagcaggc cgacaagggt    28260
gaactgaagc gggatgcctt cgacaagtgg ggggccgcga atgagaagta cgtcaccacc    28320
cccaccatcc acgccatcat caagggcaac gaagcggcca tcgagcggca acagaagctc    28380
atcgctcaga acgccctcct ggcccaggcc gaagcaacac aggctcaggc aacgcaggca    28440
gcccgcacgg ccatcgacca gggcaacctg gcgttcctcc cgcagcagaa ggtgatgaca    28500 cctcagggg aacagaagaa cttcgatacg aaggccgctg ctgtcccgta catccaggaa    28560
cggattgcac gggagaacat gccgttcggt aagcaggtgg agttctggtc caccaacggg    28620
gtggagaatc ccgagtggga gaaacagatc aagggtggcc tctcgaacct cgcctccgcg    28680
ggctggacct tcgatggcaa gaccattggc caactgaaca accagggcca ggccgcaatc    28740
gacaccttca tccgcatcaa cagcaccaac cccggctacg ctgagaagtt ggtgggcggt    28800
gacaaggact acaagaagct ctccgacatc cagttcctca tggagaaggg cggcttcccg    28860
aacgtcaacg atgctgcggc actcatcaac cagattgacc gcgctgacat caaggcatcg    28920
gactacggtt cgatgaagca gaaggtggcc tcctcggtgg acgatgtggt gaaccagcat    28980
tggtactcag gcgccaccag ttggttcagt ggcctcttcg gcaatgacca ggtgaacctc    29040
accgctgtct ccgctgacat cgccgcaggg gctgaactcc tggtgatgtc tggccaggtg    29100
cccgatgcga acgccgcggt gaaggccacg gtgaataccc tggcgaaccc cgcagtcacc    29160
acgcggatca caatacgct ctacttcaac aaggaccttc cggtggtccc gaagggcgag    29220
gacaccgggc agtggatggg gcggttcatc aaggacgttc cccagcagat cgccaaggcg    29280
```

```
aacaacctcg gtgatgctcg cctggagccg aaccagtacg gaggcttcac ggcctggact   29340
ggtggtgtcc cgatgacgga cggcaccggt aaggtggtca cctacacgcg ggatgacatc   29400
tcgaagtggg tggacaacac catcaccgct gaccgccaca aggccgctgc tgatgccaac   29460
ttcaagagct accaggaccg cctcgtgaag gaactccgcg atgaaaagca gaaggacccc   29520
tacgtgatgg agcggatgtt cgacgcgact gccaacggca tgtggtggaa ccgccaactc   29580
tacagccgcg aaggctatga gcaggttctc cgtgacggca acacaggcaa gccgctcaac   29640
gaactgttcc aaatctacaa agacaaacgc ttcaaggata agtaatggcc gcatcgatcg   29700
ctctggggga tgtccagagg attacctccg agacggagaa gaagtacggg ctccctgaag   29760
ggacgctgtt caagatcgga aacatcgagt cctcgttcca ggatggccag gtgagcccga   29820
agggagccaa gggctacttc cagttcaccg atgacaccgc aaggcgctac ggcctggatg   29880
atccgttcga cttcgagaag tcatccgatg ccgcgggccg gtacatgcga gacaacctgg   29940
ccaagtacca gggcaacatg gacctgtccc tcgcggacta caacggtggc ccgaaggccg   30000
ctaaggctct cgccaagggg aagccctggg cagagacttc ggactacctg gcgaagttct   30060
acggcaacaa gtccgagccg ctctcgcagc aattcaccac gggctccgaa gtccctctta   30120
ctgcctcccc ctccgcctcc cagctatatc gagacgcacg gcagcaggag tctgagtatg   30180
gaggggttgg caataacatt ctcaatctgc ctcgtgctat tggcctgggc tttcaagtcg   30240
ataattcggt ctacaatttc tggcaggagc gaggactctc cagcgtagac cccgacttcc   30300
gctgggacga tgacttctcg aagcagatgc ttgatggggt ccctgagcgt cattggggat   30360
acctgctgca atccaagtcg aagcaggaag cggaactccg ccgtgcccgt ctgttggaca   30420
cgatggagaa ggaagtcgaa ctctccaaga tgggtgtggc cggtttcggt ggtcgcctgg   30480
tgggcaacct ggtggatcta cctacgctca tctcgttcgt ccctgggttc ggtggtgcgg   30540
gcctcctcac gaccacttca cgcatcgcca atgctgcccg catggctgcc ctcggtgctg   30600
ctacgaacgt agccttcgat gctgcaacga tgcagttccg ccccacggcc accccggatg   30660
acctctacat ctccgctgcg atgggcctgg gtctcggtgc tgtctggtgg ctctcggtga   30720
atcctgcccg cctggccgcg caacgtctcg ctgctgagaa ccgccgcctc ggtgagttcg   30780
gtctccgtga atccggcaag gcgcagatca aggagcttgg cgacaacggc ttcaacttcg   30840
gtgctggccg tgaggagttc gcacggcgca tccaaggcaa gcccgatgag ccggtggaga   30900
tcaagtaccc aggcggtgca atcgtgctgc cgcggggcga tggtgagcct ccgaagattt   30960
tccaccctgg tgatcccccct gaggttcgca agccaggaa catcaacgag ccgcttcctc   31020
ccgaagctcc tccagctact cctccggcca ccggcccggt tgctcccaag gctcctccag   31080
cagaggcacc taagggcaag ggctggacct ccgagtggga cgctccgcgg tacgcctcag   31140
gcggtggcaa cgagcaactc ctcgtgctgc ctccggcaaa gcgtgtgagt cagttggctg   31200
agtatgtccg ccagttctcg aagaacgggg acatcgtgag ggtgatggac cgggtgctga   31260
agggcatcga cctccgcaag ttggagttca aggtcatcga gaagggtcag cgtttcggcc   31320
agcgtgacat ggacaacgaa atcctcggcg cgaagggcgc tgtaggtact ccgcgaggtt   31380
ccattggtga caacatcata atgttcctgc ggggccactc gtgggagatg cctggtgtca   31440
acccgatgca cacggtgggt ctcaacgagg agacgttcgt tcacgaactc gttcacgttg   31500
ccaccgtcta caagctccgc ggtgttgagc ctggcatggg tgtacgcatc acggaccctg   31560
ttgtgcgcag ggctgctgat gacctggcga acctccacgg ggacatcctc gaccacgcca   31620
```

```
ggcaaacctt cggggccaac tggaaaggtg aactccaggg acgcctcggt gccaacctgg   31680
agaacgagaa ggaactcatc gcctatggtc tgacgaaccg gaacttccag gagtggctca   31740
agacggtgcc cgttgagggt ggccctgaga agaacctgtg ggaccgcttc gtgcattccc   31800
tgcgcaagct cctgggcatc ggcccgaagg aacacaacgc cttcacccgg ctgatcgaac   31860
tgtccgcccc tctcacgaag aagggcgact tcgttgagcg catcaagacg aacccagagt   31920
tggaagcaac gggtgggttt gttgacgctg acaccgtgaa ggccgcgaac gaagctgacc   31980
tggctccggt ctatggctgg ggtctcggcc tggagaacag gctgggtggt gctaaggctc   32040
cctccgctgt tcgtcagttg gcctcgaagc tgttcggcac caccatcggc tacaaggaca   32100
acgcggtggt gaagctcaac gcttgggacg acaccacgaa gtgggctgac tcctgggccg   32160
tggagatgcg caagggcacc tatccgcagt tcgaggagtg gctcaagggc tctcagtaca   32220
agtggcacga agggcaag gcgttcgatg acttcggcgc acaggtgtcc aactacatcc   32280
gcggcttcga gggtgattac ccaccgcagg tggtcaaggc tggcgagcac atgcgcaaga   32340
ccctggccaa cgtggtggac tacatcaaca gcccactgaa ggacgaaggc cgagccaaga   32400
ttggtctcac cgagacggac atccgagacc cggagaccgg caaggtggag cgggtaggga   32460
cgctggagaa gaacccgaac tacctcccgc gcaagcacga catcaacaag tggaactcga   32520
tggtctccaa cttcggcagg gatgccgtgg aagggtggtg ggcacgggcc taccaggctg   32580
gccgtgaggg aatctctgac gaggccgctg cgaagtgggc caagtggtat gtccgcacgg   32640
tggaggaggc tcacgccaac cgcactcagg acatgctcga tgacctcctg aagggcaccg   32700 ataggacgc cctgaagaac tccctgatgc tcaacgagg ctactccgaa gcggaggctc   32760
tgcggatcat ggacgacatg attcctggta gggccaccga tgcaggccgc acgatggcca   32820
gcctgaagca ccgcaacacc atccgggaaa cgcacaccga gcagtggacc acgaaggacg   32880
ggacgaagat ggaggtgagt ctgaacgact tcatccactc gaacgccttc gacgtggttg   32940
agccgtacct ccgcaggacc gcgggcagtg tggcgctggc caagcatctc gacatctaca   33000
agatggggga cattgaccgc gttatcgctg aggccaccgg caacaagctt gggcaggagt   33060
tcaagtccac ccccgatatt cagaagctcc gcaaggacct gaagttcgcc ttcgagcgag   33120
tccaagggct tcccctggag gagttctcca cgctgaacaa gagcctggag atgtggcgca   33180
acttcaacgt tatccgcctg atgggtggag cagtctggaa ccaggccacc gaactcagcc   33240
agatcatcgg cacgatgggg tggaagacta cgcttgcggc tctccctgag cttcgagcac   33300
tgcgccgtga catcgccacc ggcaaggccc gcatgacat cctggaccac ctggagaaca   33360
ccattggtgg cgtagggtcc gagtacgtgg cccgcctgga gttcaaggct ggtgacgatt   33420
gggtccgcaa caaggggac accaggttca accgctggct ggactctgct gacaccggca   33480
ccaggaagct ggcgaaaggt gtgctggatt acaccggcat gactccgctg atgattcagc   33540
agaagcgtgt ccacgcgatt gcgttggtga accacttcgt caacgtggcg aacggcaagg   33600
ctgctgggtt cctcacgaag gatcgcctgg cctggatggg tatgagcgcg gatgacttcg   33660
gcaaggtcct gtctggcatc aagcagttca ccaagcccgc tgatggtgag ttctcgaaga   33720
ccttcaagat ggacttcgcg ggctggcaga aggcggaccc ggagagctac tcgaagttca   33780
tgacggccat ccaccgtgaa tcccgcaggg tcatccagga aacgacctg ggctccatga   33840 tcccgctcat gggcaccacg ctgggcaaga cggtcttcca gttcatgaac ttctcgatgc   33900
acggctggaa caagtcgctg atgttcgcca tgaaccaccg cgactggtcc acactgtcca   33960
ccgtacttca cggctcactc ttcgcgtcca tcgcctacat ggggcggacg ctgctgggtg   34020
```

```
ccggtggcat ggaagcggac aagcgccagc agtatctcga caagcggatg tccgttggcc   34080
agatcgttac caacagcttc gggcgcatct ctcaggcgtc cgtgctgccc aacatgttcg   34140
acaccatctc accgtatccg ctgttcagcg gaatgcggac cacgagtgac ctctccagtc   34200
tggcatcgaa cccgacctac caggccatca acggactcat ctcgatgaag aagctgattc   34260
ggaatggtgt gtcggatgag taccaaacca cggagaagga catccgcacc tggggcaggc   34320
tactgcctct caacaacgtc ttcccggtga ccacgttcct gaaccacctg gcgaacgatt   34380
atccgcacgg cgaaaagcaa caataaacgg gtagccctcg gcacgaccgg gggcaacctc   34440
ttttggagaa tagatagtgc cttacagtta cgttcttctc tcggggaacg gctctgcgac   34500
caacttcggc ttcagcttcg gttatctcag caagttccac atcggagtga aggtgaacgg   34560
tgtagtcacc accttcacct gggtgacgga cttcaccatt ggcatcacac cggcccggc    34620 caacggtgca gtcatcgagg ttcgacggac gactccgttg aatcaacccg ccgtggactg   34680
gtcagatggg tccacgctca ccgaagcgga catggacctc aacactcggt tctctctgta   34740
cactgctcag gaggccgctg atggtgttgc agcatccatc actcagaact ccctgggca    34800 gtgggacggc cagaaccgca gggccgtcaa cttcgcagac ccggttgatc cacaagacct   34860
ggtgaacaag cgatacttcg aggacgtgta cacacctcag ttggacgcga aggtcaccga   34920
agccaccaac caggccaaca cgcggcctc cagcgccgcc actgcgcagg gctatgctct    34980
cgctgcggac aactccgcgg acctcgctgc ggccctcctg gcgaccttca aaggccagta   35040
cctcggtgcc cttgcatcta accccacgct ggacggtaac ggccagccgg tgactgctgg   35100
tgacctctac ttcagcacca ccgataacct gatgaaggtg tacaccgggt ccgcgtggat   35160
caacgctggg tcaaccgtcc agtccaccat caaacgtcct gtcacaccca tcgtggcaac   35220
cgcaggccag accgtgttcc cggtgtctgg tgggtacgac gccccataca ttctcgtgtt   35280
tgtgaatggg gttgaggtgg cttctccaga tgtggacgtg actaacggca gcaccatcgt   35340
attctccagc ggcctgactg ctggagataa agtggattac gcagcgtttg gtgcgttcca   35400
ggtggccaac ccggttatcg atgggaccag cgccgcagac ttcatcaaga cacgcaatgc   35460
ccgtgtagtt acctctattg ccgacctgaa ggccctcaat aagaacacct acaacttcgt   35520
tctcgtcact ggcttctatg cttcagggga tggtggcggc ggtttcttcc ttcaggttcc   35580
cacgatgccc accaacggta tcgttcaggt cgggaatgac ggaggcatct ggcagttggt   35640
ggttgatcgg gattatgttt ccgcgaaaca actcggtgcg agactggacg gttcaacgga   35700
tgactcctct ctcctgaaca acgccaagtc cactctcgat gctcttggta agaggctgta   35760
tatcccgtct ggggtttgca gaatctcaac agcaatcact ccaccaaagg ctggtgtgtt   35820
tggggatagt cctcaagcgt ccatcatcca gtgtaacaac tgctctgcat tcctattccc   35880
agcaaatttt gggctctctc gtccggcttg tgtcattgag aagttgggga ttcagtccta   35940
cagcaacacc tgcgatgggc tatacgcttt ccgtgcccct ggggtggcat ctggagcatc   36000
gcccgtctac aacagcggcc taactgttag ggatgttgag attggtacgg gcggacgatt   36060
cggtggcggt ttctcactga aggacttctt ccgagtgaac gtagagaaca ttggcatgac   36120
tgatgtgagt tccgccgtat tgctcaccgg gtcagttgtg caggcagtat tccgaaatgt   36180
caccgcaaac ggtgataacg caccaactgt tcttaaccgg tatggtttcc aaacagccgc   36240
agcttcctat tccagcggta cgctaggtcc tgaacacatt agtacgtggg attgcagctt   36300
cattcgctat acacgcggtg ttcaacacga tgctgggctc atggtctcgt tcaacaatac   36360
```

-continued

```
ggacctggaa actttcacac acggcttcta tctctcgcag ccctgcactg tgcgtggtgg      36420
tattagcgcc ccggctccgg cagcttcagg gactgctgcg tggattgggc ttttcaaagc      36480
tatttctgat tttgacgtag ccaacggcac tctgatcgat gaccttgaga tcaacacgct      36540 aaacaccccca ggaactccag cctcttcgta tggggttctc attggcaaca atgtgaataa      36600
gtgcattggt actacaatcc gtagtcccag gattcgaggt aacactagtt caatggtcgg      36660
tgggattgtc gctaatctag ctggaggtga catcgttatc gaggatgcca tcatcaacg      36720 cagtgtggtt actggaacta cggtgtctgt gaacaatgct tcctatgcaa gggttgtggg      36780
caatcgaagc gccaccggtg ggactgtaaa tggttccctg tcaatcacag ataacggtgt      36840
tggttccatt ggtgatgttc gtggaaatga gtttgccacc attaccaaca ccctcaatgc      36900
ctattccggt acatggacgc ctggaacaat tcctaacgga acaccagcag caacaacggt      36960
ggccgtccct ggcgcagtgg ttggtgacaa agtagtggtc ggcctttcca gcctgaccgg      37020
atcggccaac tgcatcattt ccggctatgt gtcttccacc ggaaatgtgg ctgtcctgtt      37080
gtataacgtc tctggtgcat cacagacgat tccctccggg actctccagg taacagtcct      37140
caagtcgtaa tcaagatgtc cctctaggtt tccctggag ggacttcctc tttcaaggaa      37200
aggtatgagc aatgcgctca acgtaagtaa gctggccaca ctcacggcaa cagaaatcaa      37260
agcataacca acaagaagt aatcatgccg aacatcgaca aagacgtaca aaggatgct      37320 ctgaaggagg ccctcacgga gtggctggac aagcagttcg ccacattcgg gaagtgggcc      37380
ttgcggtcca tcctggccgc tgccttctca gtcctcatgt acctgtacct gacttctcaa      37440
ggctggcacc gctgatatga ccgaaaagac caccgcttcc gaaaaggagc ttggcgaagt      37500
tcacaacgag atggccgcat ggtgcctgga catcctcaag ggaatcccgg tcaccgacaa      37560
agacggtaac ctcgtgattg aggatgggag agttgttcgt ctccctccgg ctcctgccta      37620
cctcaacgtc attcgccagt tcctcaagga aacgacatc caggctgaac ccgccaaggg      37680
ctcctcgatg ggtgacctct cggacctccc ggtgttcgag gatgacaacg ttgtgcctct      37740
caagtctcaa tcgaaataaa cgcgattaga ggccctcaga gcgatttaa gcctccaagg      37800 tagggtagcc tatccgggca cctgatcgcg tcctgtgggg ccatctcgca agccaagaat      37860
gaaaataaca actgccgagg tttcggcaaa acgctgcccg aagtgcggcg aagaaaaaca      37920
cctctccgag ttacacgcga atcacaccaa gaggggcggc cacaacacca tctgcaagct      37980
ctgcatgaag caggtggcac gagactggcg caacacacct ccgggccgct ccaagcagat      38040
gtggacgacc tcaaagaaac gtgcggagga gaggggctgg gagttcaacc taaccccga      38100 gtggattcag gaacgcctcg aagctggcgt gtgtgaggcc accggattc ccttggagat      38160 gtccgcggag gagttcaaag gctacggcca cttccgtcca tggacccct cactcgaccg      38220 agacgatcca acgaaagggt acacaaccga caacgtgaag gttgtgtgct ggatgtacaa      38280
ccaggccaaa ggcgtaagca tgcacgaagc cgtcctaaga atggcccgtg ccctcgtagc      38340
gaatgacaac taaacaacac ccagcacaga aagactttcg cgtctttatg ttcatggtgt      38400
ggcgccacct caatctcccc gaacccacac cagtccaata tgacatcgcc cactacttgc      38460
aacacggacc acgccgttca gtcatcgaag cgttccgtgg tgtaggtaag tcctggatca      38520
cctccgcctt agtttgctgg gttctgtgga acgacccaca gaagaaaatc ctggtcatct      38580
ccgcctcgaa ggaacgagca gatgccttct ctaccttcgt gaagcggctc atcaacgagc      38640
ttcccgttct ccagcacttg aagcctaagg cggaccagcg agactcgatg atttccttcg      38700
atgttggtcc cgcaactcct gaccactccc cctcggtcaa gtccgttggt atcaacgggc      38760
```

```
agatcactgg ttctcgtgcc gacatcatca tcgctgatga cgttgaggtt cccaataact   38820
ccgccacgca gatgatgcgc gacaagctct ctgaggcggt gaaggaaatg gatgcggtca   38880
tcaaaccgct ccagacctcc cgcatcatct atctgggcac gcctcagacg gagatgtcgc   38940
tgtacaacgc tctccctgag cgtggatacg aagcccgcat ctggccagcg ctgtaccccg   39000
agcttcacct cgtggccaac tacaagggcc gcctggctcc attcatcacg cgggctctgg   39060
aggccgataa gagtctcgta ggtgctccta cggaccccag gcggttcaac gagactgacc   39120
tgttggagcg taaggcgtcc tatggacgtg ctggcttcgc tctccagttc atgctcgaca   39180
cgagcctcag cgatggtgac cgctacccgc tgaagatcgc ggacctcatc gtccagaacc   39240
tcaaccccac gatggcccat gtgaagatcg cctgggctgc tgcacctgaa gtttgcatca   39300
acgatctccc cgcggtggcc ctcacggggt accgctacta ccggcccatg tggacggacc   39360
agcagatgtc cgagtacacg ggctgtgtca tggccatcga cccctcgggc cgtggtgctg   39420
acgagaccgg ctacgccatc atcaagattc tcgcaggcaa cctcttcctg gtggccgcgg   39480
gtggactctc cggtggctac tcagatgaaa ctctggagac cctggcgaga ctcgctaaga   39540
cccaccaggt gaaccacgtc atcatcgagg ccaacttcgg tgatggcatg tacaccaagc   39600
tcatcactcc attcttcggg aaggtgggac acaaggtcct ggtggaggag gtgaagcact   39660
ccacgcagaa ggaagcccgt atcatcgaca cccttgagcc tgtgctctcg actcatcgtc   39720
tcatcgttga ccagaaggtc atcgagaacg acttcaggac ggcagagcag gacatcaagt   39780
acagcctgtt ctaccagatg acccggatca cccgagacaa gggtgccctg gctcatgatg   39840
accgtctcga tgcactggcc atcgctgttg cctactggac ggagcatatg tccagggaca   39900
acgataaggc cgctgctgcg atcaaggaca aggcgctgaa ggatgaactg aagaagttcg   39960
ttcacggtgt ccttgggagc aaacccaagc gaacctcgtg gatgtcctcg aactcaggct   40020
ccaggtgaca ttcggtgcca cataggaga acctacgtg ggttcttcgg gggcttcatc   40080
cgtagctgat atggatgcca cacaccgtgt ggactcggga aacctcagtg tgtggtgatg   40140
tagtcgctgc attctaggac acccgttagt ctccctattc ctcatctcta tgggggggtag  40200 gggggctaac ttaggtgttc ctagtgttga tgatatagcc actgagatgt caacctcagt   40260
gtcccttaag ttgtctctta gggttgcatt aaggagacat catcaccatc atctcccata   40320
aggtcatcct ccccatgttc actctactag tcctcctctc aggtgtcccc gtggtgttcc   40380
ttctgggtct cgttctgtat ggcctgttgg acaactgatg gtgtccctga agtgccccct   40440 taggggaaa acttccgacg caaaaatttg aaagccccac tcgaaattcg acgcgggcag   40500 attcccccg tgcccctcc gcggcccggc cctcgtggcc cctgccgacc cacctccggg   40560
caccctccag gctgtacgct ccgctgactc c                                  40591
```

<210> SEQ ID NO 2
<211> LENGTH: 41117
<212> TYPE: DNA
<213> ORGANISM: T7-like viruses
<220> FEATURE:
<223> OTHER INFORMATION: /host="Ralstonia solanacearum"
    /aisolate="vRsoP-WM2"
    /isolation_source="Cayo river, Badajoz, Espana"
    /note="Genome of the virus vRsoP-WM2"
<220> FEATURE:
<221> NAME/KEY: misc_feature
<222> LOCATION: 8340..8805
<223> OTHER INFORMATION: /note="insertion with regard to vRsoP-WF2 and
    vRsoP-WR2"

```
<400> SEQUENCE: 2
ccccatgttc actctactag tcctcctctc aggtgtcccc gtggtgttcc ttctgggtct      60
cgttctgtat ggcctgttgg acaactgatg gtgtccctga agtgccccct aggggggaaaa    120 cttccgacgc aaaaatttga aagcccccact cgaaattcga cgcgggcaga ttccccccgt    180
gccccctccg cggcccggcc ctcgtggccc ctgccgaccc acctccgggc accctccagg    240
ctgtacgctc cgctgactcc tggcacatct tctggcacac tctgccgtaa ctccctgatt    300
actaagggga tgcactagct tacgaagcta ctgcgaccca ataagcctca cgcatgagca    360
ctcactggct cactcgtggg gcttttttttt ctattctgtc cccatttccg cgcccccctg    420
ttcggccatc agtttgcttt ggtttctcct agggtttccc ctaagtgtct ccttggcgtg    480
catcgctacg attctcccaa cggcccactt gcggcccacc actggagaac atcatgcaac    540
tgcaatactt ccgcgacttg gcaatcggca cagcgttcac tatcgctggc acgccctacg    600
tgaagaaaag cgcacggact gcgtacaccg ctcccggcca ccctgggcat tgggaaggcc    660
gctggttctg gtttggtcag actgaactgg taatggccta agggagcaca ccatgagcaa    720
agtccgagca ctcgcctact tcttcgctgc aaccacgctc gcactcacct acgtgggcgc    780
aagggcagca catgcggcca tctcaagcct cctcgtgatg cacctgcatt gatcccactc    840
agaacaccct ccttggcggc aaagccgcta cagaagcctc cagatcaacg tctgggggct    900
tttttgtttg ctcctggggc tgacctacct gcgtcccact gcgtggctcc tagggcttcc    960
tatcgttcct tcggagcaac gctcctgata tcggaactat tgcagtgatt gaaaaataca   1020
attgggcagt ctccgatgtt tcgtatgtaa ttcggtctca ccaggggggac acgcccctga   1080 agacaaaaaa gcgtgggacc ggggcggacg ccagcagtca gggacaaccc gagtcaatcc   1140
aagagtaagc acattgcgag tccttccagt gtgctcatca ctggagagac atcatgcaat   1200
cattcaccct gaacattggc cttatcccga gcaagaaatc ttcgcgtacc gctcgcatca   1260
ctgcatcgga agttaaggcc gcacttcgtg gcgctggctt cttcgtgtcg ggctttcgca   1320
tggcccagtc ggccaccgag cctaccgcag tggtccgcgt gatcgcacgt cagccaatga   1380
gctatcacca agcgctctac aacgtgtccc tggcgctggt gcaggactgc atcgcggttg   1440
tccctgacac ggtacggggc gcgttgattg gcccggatgc ggctgagtgg ggtgagttca   1500
atccggccta cttcatcccg tttgatgtcg aaccgcaggc aatcgctgcg tgacacttag   1560 ggtgccccctt caggggctcc aggagtagcc gcattgcgct gtgcagtgcg cctatcactg   1620
gaggacaaca tgtacggaaa cttttgacccg agcacgaacg catggccgtt cagtgtggag   1680
tttgtggacg ctgtaggctg gcaagtggag gacaaccggg accccaccaa tgtcgtggtg   1740
atggtcgctg gtctcacctt cgaggaagcc aaacagcgcg cgtctgaact caacctgaac   1800
cacttccggg ggtcctgaca tgccgactct caaggaagcg agcgtgaatg ctcagagacc   1860
acgcggaggc gtccaagcgt ggagcgtagg ggacacctac ccggtcactg tagtgggcct   1920
gggcaatggc cccgcgtgc aatggtacgc ggagaacctg cacacgggcg aacgtggccc   1980
cgtgcgagat gcccagggtg atgcagtggt ggaccagtat cgtctttggg cggagttcaa   2040
cagaaatcgc ctacaggcgt aattcggtgg ccctgttcat gtgtcgtgaa cagggctcca   2100
ggagtgaacg cattcaatcg tgagtgcggt catcactgga gaatgcaaca tgcaaacgaa   2160
agaacagcgc atcgaactaa tcgccgcgat gtttggtgag caagaaacgg gcctgatcgg   2220
taagcaactc cgcgtgctgg ataactccca aagcgggggcg ttctacaatg ttggtgatgt   2280
cggtaccgta gtcctcgtgg acgatgacgg tgaaatctgg gtggactttg gcccggatgg   2340
```

```
cttcaaaggc gatggtacgg catacccggt ctgggccgct ggttcgctgg gcgcagacga   2400
ccatgagttt ctggaaaact gacatgggcg tcatctggca cgaactcatc tacgccctgg   2460
gagccctcgt ggttgtcggg gtcctcattc tgatcctcac cgagggagac tgacatcatg   2520
cgcacctttg caatcgactt catgctcaac ggcaagcgcg ttgggcgtga ctacgtgacg   2580
gcttccaacg agaagcaagc caccatcatc gcagaacgca ctgcacccgt gacgctgtat   2640
gacgaggttg tggtcgcacc gctgtgatgg accatcgggc tcccttgtgg agccccagg    2700
agtggaccct ttcaattccg agagtgtcca tcactggaga gaatcatgtc ggacaaagcc   2760
aagcaatcca tcgagttcgt tcgcaacggc ctgggcgagg aaaacttcaa caagctcctg   2820
agcatcacgg gagtacgtga catcgaactg gctgccgcgt tcctggcgac caccaaggag   2880
gagcgtgact ctgtgaagac aggtgacgac ctcatgcgcc tgctgggccg caagcacgct   2940
gagaaccgcg tggccatggc tctggtgcgc gcgggtgtgc cggtggagga tgccgtgtct   3000
ttcgtgcgtg aaaccgctgc aagcctgtaa gccccaaggt gccccttagg gggcctctag   3060
gagtgagccg ctggaatcgt ccgaagtctc atcactggag atcgctatgt ctgcacaagc   3120
cgaacaaacc caaaccgccc cgaccatcat cgccctgctg tctgctgcga atatggctca   3180
gacgggcccc ggcgtcttcg ctggcgtcat caaccaagcc acacctgagg agcgcgcggg   3240
tgtgaagaac atgaaggacc tcctggcgct gtacttcaag gttcatgcgc gagtggtggc   3300
cgaaatctcc gcggaagtgg aagccaccac ggaccatcgg gctcctctgg tggacctgtc   3360
cgacttcgct gagaccctgg cggagtactt cagccgtgcc gatgaagtgg tgccggaagg   3420
cgtcacgctg caataacgct gggtgccccg aaagggctc caggagtgga tgtcttcatt   3480
gtgaggacct ccatcactgg agaaagcaat ggcacagatg cgcgcctggg tctacaaggc   3540
gcactggagg cggcacctgg ccgcgcaagg catcgtcctg cgcaaatacg aggtggacaa   3600
ggagtacatg caccgcggca tgacgcaggc catcttccgc cgcaacaaag cgaagttggt   3660
ggccgagtac acggagttct gacatggaca tcgtagacga actggagata ggaccctctt   3720
acgtcctgaa ctcggacgag aagtggctcc gcaagagagc cgctgaggaa atccgcaggc   3780
tccgaaagca actggcggac gctggttggg ctctcgaagc ggcccgtgaa ctcgaagacc   3840
aacgagacaa cggggggtgg ctatgaaacc cgctgacggt caacccaagc gcttcaagct   3900
gcacaccaag tatccccaca acaggtccga gggtttgact catcggacca acaagggac    3960
cgcgcttcaa gttctaccga agaggtaacg ccatgaagat cactctgaca ctggaggaca   4020
ccgctgatgg tgtcgctgtg aactggaccg aggagcaatc tgaagctcag aacaaaccca   4080
gcgagagcct ggccaccatc atcgctgcca gttcattct tgagataaat caatctcacc    4140
gtatgggaat tttacggctg tccggcactg cattgggcgc agatcgcgca tagctagtat   4200
gaggtgtgtt gcgtagagtg cgaaccagtt ttatttggtt cgccatgccc gcatccagaa   4260
gctcatcgca acagtagagg agtagcaatg ccggtcatca aacgcgggaa caagtaccag   4320
gccagtgtgg gctctggtac tgatcgctgg cgcaagatgt tcgacaccca ggaggaggcg   4380
gagaccgcag aactggcaga gaagctgcgc aggaaggccg ctgggaagga cgagaagggg   4440
gctacaagct ccgcaaatgg ggcgaaggta cagaagaccc taaaggaggc ttacgaccgc   4500
accttggccc tgatttggaa gggcaccgct gcggagaaga cccacatcat caactcgaac   4560
tccgtgatgg cggagttggg caaggacacg ctcctgtccg acatcgccac cgaggacgta   4620
acggagatga tcctggctct ggaggagaag ggcaactcag cagcacggt gaacaagaag    4680
```

```
ctgtcctgcc tgtccatgat cctcaagacc gcctcggatg agtggcctgg gtgcatcgtg    4740
gagatgccca agctgaagcg gcgcaaggag gggtctcacc ggctccggtg gatcaacgag    4800
gccgaggaga agcggatgct ggaggccgcg gagcacctgg ggctctacga cctccgggac    4860
tacatcatcg ttggcatcga caccgggttc cgccgcggag aactcctcgg gttccccctg    4920
aaggactacc agggcggtct catgatcctc cacgatggtg agaccaagag cggcaagggg    4980
cgcgccatcc cggtcaccaa gcgggtccac gagatcatcc agcggaggag caactactcg    5040
tacctcttcc aggactacac ggtccacaag ctgcgttggc agttcgacca actgaagctc    5100
cacatggggc tccaggagga cacgcagttc gtggtccaca ccctgcggca cacctgtgcc    5160
agccggatgg ttcaacgtgg ggtgcccctg aaggtggtcc aggagtggat gggtcacgcc    5220
accatcgcca cgaccatgcg ctacgcgaag ctagctccga gcagcctgct gatggcgaag    5280
aaggccctgg aggaagaacc ccaggaactc acattcattc ctccccgca gatggatgtg     5340 gtggagcttc acgacttcta aggaaaggaa ttgaacacc tcagagagac gttcaaggga     5400
aaggtacaga gacaggcagg acgagatggg tgctgggttt ggcaaggctc taagacggac    5460
aggggatatg ggaacctgtg ggacccaaaa accaagaagc ctgtctcagc acatcgactg    5520
tcctaccaac tccacaaggg acaaatcccg gaggggttga tggttctcca ccggtgcgat    5580
aacagggctt gtgtgaaccc aaagcacctg tttgtgggga ccgcccagga caatacggtt    5640
gacatgtacc tgaagggtag aggaacagtt ccacattagg ttccacataa ggataaccct    5700
gaagggaaac ctaatgtgta aatcctaagt gtttatcttc atagatagac actattaatg    5760
atatctactt agagagaaca ctttagttga cactatgact acccaacaag tggacaacga    5820
gaacgaagac ctggtgacta ttcagcttcg tctcgaagaa gagatgaccc agcggggagc    5880
agaccggtac atccgggggg tatccaaggc catcgagaag ggccgtgagg atgacaccgc    5940
ctacggcaag caaatcctgg ccgggaggtt ggcgaagctg gcccaggcca tcgctgagtg    6000
gaaggcggag gtggcctctg gtaagcctgg ccggaagcac tcggcctgga agctcatcaa    6060
ggacacggac gacaacatcc tcgccttcct ggccctcaag cacgttctct cggggggtctc   6120 cgcagtccgc accgtccagt acgtggccgt ggccatcggc accgcggtgg aggacgagat    6180
gcggttcgcc aaggtccgtg aggcggagcg gaagaagttt gagcagctag tcaccggggc    6240
agcgaagcgg accagccagc actacaagca cgtctacgcc acccgcgtgg ctgaggacgt    6300
gacggagtgg gacaagtggt cccggactga ccgcctccac gtgggggtca agctcctgga    6360
cctcctgatg cagtccatcg gcctggtgga ggtgtccacg aacctggaca cagcgagca    6420 ggggctcaag tacgtgaagg ccctcccgga gaccctggag tggatcgaac ggaagaacga    6480
ggtgaccgcc ctgctgcgcc cggtctatga gccgatggtg gttcagccgc gggattggac    6540
caacccgttc gatggcggct acctgtcctc gaacatcaag ccgctgaagc tggtgaagac    6600
gaagaacaag gcgtacctgg aggaactccg cggcgctgac atgcccatcg tctacgaggc    6660
agtgaacgcc atccagcgca cggcctggca gatcaactcc caggttctca cggtgatgcg    6720
gcacctgtgg gactcaggct ccgagcttgg tggtcttccc cctcgggagg gactgccgat    6780
gccaccgaag ccctacgaca tcgacaccaa cgatgactcg aagaaggcgt accgcatcgc    6840
cgcagcgaag gtccacatgg agaacctctc cattctgggc cagcgcatcg gcttttgacat   6900 ggccctgggc attgcgggcc gctacgagaa gtaccggcgc atctacttcc cgtaccagtt    6960
ggacttccgg gggcgcatct acgcggtccc gcacctgaac ccgcagggt ccgactacca     7020 gaaggctctc ctcagattcg ccaacgggaa accgctgggc tccgaggggt ggaagtggtt    7080
```

```
ggccatccac ggtgcgaacc tggcgggcta tgacaaggtg agtttggagg accgcgtgga   7140
gtgggtcctg gagaacgaag atgagattct cagaatcgca agtgatccct acgaccatcg   7200
tggttgggca tcggaagtgg gggggttaa gatcgacaag ccctggcagt ttcttgcctt    7260
ctgctttgag tgggctgggt tcgttgagca tggtgagtcg ttcgtatcaa agctgcccgt   7320
ggctatggac ggttcatgct ctggcatcca gcacttcagc gcgatgctcc gggacgaacg   7380
aggcggggcc gcagtcaacc tcgtacccca ggacctccca gccgatgtct atagagccgt   7440
cgctgagaga gtcattgaac aggctgaaag tgatctcgct cacggttccg aggacgaact   7500
gaagcacaac ggccagggca tcgcttacct gtctgagggc tccaagacca tcgcccagca   7560
gtggatcaag ttcggcatca cccgcaaggt caccaagcgg agcgtgatga cgctggccta   7620
cggctccaag gagtacggct tcaaggagca actcatggag gacatcctgt ggccagcgaa   7680
gagggcagcg atgcggcctg atgggtccat cgacacggag aagttcccgt tcagcgggga   7740
tggctaccgt gcggctctct ggatggcgaa ggcaatctgg aacgcggtga acgcagtgct   7800
ggtgaaagct ggcgaggcga tgcactggct ccaggaggtg gcagcactgg ccgcgaagga   7860
ggaactgcct gtccgctgga caaccccggt ggggttcccg gtgatgcagg cgtatccggc   7920
cctggaggca cgtagggtga agaccgccat caacggcatg gtgctgaagc tcctcatgaa   7980
ccaggagaag gactccctgg acaagcggaa gcaggggcag ggcatctcgc caacttcgt    8040
ccactcctgc gatgcggcgc acctgatgct cacggtggtc cgcgcgaagc aggaaggtat   8100
ccagaacttc gccatgatcc acgactcctt cgggaccacc gcgggtgacg tggaggagat   8160
gtatcgggtg gtccgcgaga gcttcgtgga gatgtactcc gaggtgcgcg tcctggaaga   8220
cttccgggat gagatcgcgg agcaactttc cgagaaggcc agggccaaga tgcctgatct   8280
accggcccgc ggcctcctgg agttgtctcg tgtgtgcgag agccggtact gttttgcgta   8340
gactgtttca catttgcaac tattccttat gagtgagtgt aagaagtgcg gggttgcctt   8400
ggtgccaggt gagaactggt atccgtccct cgcaaagaag aacaaccagg tgtgtaagcg   8460
gtgtcacacg gcacggagcg aggcgaagcg gattgaagac cgcgagacca acctcccgaa   8520
gtggatgctg cgaaacgcca ggaatcgggc caaggcacag ggactccat tcgacctgga    8580
ggagtcggac atccaaattc cgctcctctg tcccgtgctg ggcatcccgc tggaagtctc   8640
acgcgggcac ttcacggaca actccccggc tctggacaag ttcatcccgg agcttgggta   8700
cgtgaagggc aacgtggccg tcatttctca gaaggccaac gtgatgaagt ccaacgccac   8760
cattcaggag gtggaggcac tggccgcgtg gatgcgtagt cgcgcctgaa cccctccaca   8820
tctggaagag ttgagccggg ggaacgatta ggtgccacac atggataaac cagccgccgt   8880
tccccggtg gcctctcccg agacaaccga tggaacgcaa cgaacacgaa gtatcggacc     8940
agtacgagtc cgcacttggc cgcgcgattg ctcagtggcg caccggacgg cccatcccga   9000
tgacactcgc cgctgaactg atgcaacagg ctatgacgt atccgccctg gaagcacgtc    9060
acatgacctg aaccaacaat ggcagaaaag aaacaacgca acccgagctt cacctcgccg   9120
cgcggcatcg cccgctaccc ggccctcaac aagcccgact acggcaacga acagttcccg   9180
aagccggatg gtgagtacaa ggtccaactc atcctgagcg aggccgaggc ccagccgctc   9240
atcgagaagc tccagccgct ctatgacgcg gccatcgagg aaggcaaggc gaagttcaag   9300
gaactgaagg tggagcagcg caagaagctg ggcgcgctga aggagaacga cctctacgcc   9360
accgagtacg accaggagac cgaggagccg accggcaacc tcatcttcaa gttcacgatg   9420
```

```
caggccggcg gcaagaacaa gaagggtgag ccgtggtctc gcaagcccgc gctgttcgac    9480
gcgaagggca agccgctgcc gaagaatgca ccggccatct ggggcggttc ggaagtcaag    9540
gtctcgttcg aggccgctcc gtacttcatc cccggcacgg gtgctgctgg tctgaagctg    9600
cgtctccagg cagcgcaggt gctcgaactg gtgactggtg gccagcgcag tgccgatgcc    9660
tacggcttcg gtgccgaaga cggctacgag gcagacgaca acaatgaaga gggcgatgaa    9720
gccccggaca ctgatggcaa gagcggcagc ggcgaagacg agttctaaat cactgactgc    9780
caaacaggtg gccctgaagt acggcttcag gagcggcctg gaagagaaga tcgccgcgga    9840
cctcacctcg aaagggatgg ggttcacgta tgaggagcta accatcccct tacgtgaagcc    9900 cgcgaagccc tcaaagtaca caccggactt cgaccttctc aagaacggca tcatcgtgga    9960
gtccaaggga cggttcctaa cagaggaccg ggccaagcac ctgctggtga agcccagca    10020 cccagacctg gacattcgtt tcgttttctc gaattcaaag gcaaagatca acaagcgaag    10080
cccgaccacc tatgcgatgt ggtgcgagaa aaacggcttc gcatatgcgg acaagagcgt    10140
gcccgaggca tggctcaaag agccgccgaa cctgaagtcc ctaacagcca tcgagaggct    10200
gcggggagca tgacatggca tacacttcca acaccaagaa gcgggcaagc acggactacc    10260
tggtggtcca ttgctccgca acgaagccct ccgctgacat cggagccgcg gacatcgacc    10320
gctggcaccg gaagcagggg tggcgctgca tcggctacca cttcgtcatc cgccgtgatg    10380
gcaccatcga agaaggccgt tacgctgacg ttatcggcgc acacgtagaa ggccacaacg    10440
agaactccct gggcatctgc ctggcgggtg gtgtctccga gaaggatgtg aacgttgccg    10500
agaacaactt cacgcccgag cagttcgcca gcttacagaa gctcctgacg gacctccgag    10560
cgaagtatcc caaggccacc atccagggtc accgcgattt ccctggtgtg gcgaagtcgt    10620
gccctccttt cagtgcgaag gattgggcca agcaaaacgg tttctgacac accacgagga    10680
gcaaccatga aggcatggcg taaagaaccc aatcagggcg cagtccgtat tggtcgcaag    10740
accatcaacg cgaagcgtgt gatgaacaag ttcaaaccga gcatggtcaa ccatggctcc    10800
gtcctgtttc agcggatgat gctccaggcc ggtatctggg cgctctaacc taaaccatct    10860
ccagtggtac ttcgggccgg tccttcgggc tggccccct tttatgctca agatttgtaa    10920
gaggtgcggt gaatgcaagc cgtttagcga cttttcacaaa gcacccgcag gaaaattcaa    10980
gctccagtca tattgcaagc agtgcaagaa ggaatacacg cgggacactg gagctaacat    11040
cctaccctcc attcgtcaga gagcacgaaa gcagggagtc cccttctcgc ttaccaaaga    11100
gaacctccca cccatccccg aagtgtgccc ggtcttaggg gttcccccttc gacggacact    11160 cggctttgcg gacgacaact cgccatcgct ggatcgattg atccctgagc ttgggtacgt    11220
gcctgggaat gttgagtgga tgagctaccg agctaatcga atcaagaacg actcaaccta    11280
tgaagaactc gaaagggtca ctgcctgggt ccgagagcga gtttctacga cacatcccat    11340
gtgagggctg cggttcctca gacgggaaca gtctcttcag tgatgggcac cagtggtgct    11400
tcgtctgtga aacctacgtg cccggtgatg gcagcgaacc aacaatagga acaacgaaga    11460
agcggatgga agggctgcta accggggagt ttcgcccct actgaaacgg aagatcaccg    11520
aggagacggc gcgcaagttc tcgtatcaag tcggtgagtt caagggaaag acggtgcaac    11580
tcgcgccgta ctttgacaat gcaggtgtga tggtggctca gaaggtccga ttcccggaca    11640
aggagttcac cgtagttggg gatggcaagg ccatctctgg aatcctcttt ggccagaacc    11700
tatgggctcc tggcggaaag aagatcgtgg tcaccgaagg cgagatcgat gccatgtcgg    11760
tgagccaagc gcagggcaac aaatggcctg tggtctccgt accaaacgga gcacaaggcg    11820
```

```
cgaagaagtc gcttcagaag gcactcgaat acctggagag ctttgatgaa gtgattttga   11880
tgttcgattc cgatgatgca ggcaagaagg ccgctgctga gtgcgcggag ttgttctcgc   11940
ccggcaagtg caagatcgcg tccatcccga tgaaggacgc caacgaattg ctgaaggctg   12000
gccgtgagca ggagatcatc actgcaatct ggcaggccaa ggagtaccgc cccgatggca   12060
tcatctcggg agcggaactg tgggaggcgg tgtcagcatc tcaggatatc gtagagtccg   12120
ttccgtaccc ctgggacgca ctgaatgaag tcacgaaagg cgcgcgtaca ggcgagcttg   12180
tgactctcac tgcgggttcc ggcatcggca atctgccgt ggtacgcgag atcgctcacc    12240
acctcctgag gcgtggagag acggttggca tgttgatgct cgaagagaac ccgaagcgca   12300
ccgcgctggg tctcattagc atctccctca acaggcctct ccacatagac cgtgaaggtg   12360
tcagcaagga tcaactgaag gtagctttcg atgatacggt aggctctggc cgactattcc   12420
tctacgacca cttcggctcc agcgacatcg acaacctggt gtcccgtgtc cgcttcatgg   12480
cgaagggcct ggggtgcaag tgggtcatcc tcgaccacct gagcattgtt gtctctggcc   12540
tcggtgacgg agacgaacgg cgactcatcg acaacgcaat gacgatgctg cgtaccctcg   12600
tggaggagac cggcatcggc atgtttgtgg tgtcacacct ccgccgaccg gagggtgacc   12660
gcggccacga acagggagca cgtacctcgc tcacccaact ccgcggttcc catagcatcg   12720
cgcaactgtc ggacatggtg attggtctcg aacggaacca gcaggtgag aacccgaacg    12780 tcaccacgct ccgtgtgctg aagaaccgct tctccggtga gaccggtgag gccgggttcc   12840
tgctgtacga ccgggagacc ggacgcctgg aagagacgga cgcacctgct gcgcccttca   12900
aagacgaaac caaatcggac gttcagtccg agttctaacc aaaggttaca tcatgagtct   12960
gatttcgctg ttcacgcagt ccgctgctga ccaacgtgct gccgcgcccc gtgctgcccg   13020
tgtccgcgcc aagatcgcgg acctgatcga ctaagcggga gtctctgtga tcgatgacac   13080
ccgcctccaa gagttccgag aaatcctcga tgtagtccgc tgggagttcc ccggttcaca   13140
ccccgtgatt gggggcgggg ctctccgcga ttcctaccat ggtcgcccaa tcaaggacgt   13200
ggacgtgttc atgcgcaggc gtgaccacga gacgctgaac tcggaactca cccgcttcat   13260
ccgcccgccg atcctcgtgg cccacggcta tggccgtccc gacatgcacg gcgcatggga   13320
cctgatgcag tccgttgctg gctacgaggt gcaactcatc ctcgcggact tcgagaacct   13380
ggaagacctg gccggtacgt tcgacctggg gattgcccga gccaccttcg atggtgaccg   13440
gctgttcctc catccggact tcctccagga ctccacggat aaggtcttcc gcatccgtcg   13500
cgcggacaac ctgttcgaga aggcgcgaag cctgaagcgc atcaagcggc tggcagagaa   13560
gtacccggac ttttcaacac cggacttcga gcattgccct gtctgcgcac aacccatcat   13620
cgagttccgc aatgctgcca gcgtccgaga gcaccaaatc tccgggctct gccagcaatg   13680
ccagtactcg gtgttcgaca aggactgacc atgaacacct tcctcattct cctggtcctc   13740
atcggaggcc aaatcgaagg ccgcgtgatc gctgagttcg acactccccg tgagtgcgaa   13800
gcagcgaagg aacacgtgag ggtcatcaac caaccccctg tcgtcgcgtc cacgttggtg   13860
tgcgcaaggg atggccgcgc gtaatcacca aggacggtat gaagctattc gacattgaaa   13920
caaacggtct gctggatacc gtcaccaagg ttcactgtct cgtcatcaag gatcgcacca   13980
ccgggaggaa gttccgctgc atccccgcag gcttcccgat gcaagcggac atgaccatcg   14040
agcaagggct ggagcttctc aagtccggcc ccatcggtgg ccacggaatc ctcaggtacg   14100
acatcccggt cctggagaag ctgtacccgg acttcaccta cgacaaggac caggtgttcg   14160
```

```
acaccctggt ggccgcgcgt ctcatctgga cgcacatcaa ggacatcgac aacgggctcc   14220
tcaaaaagaa gcaaatcccc ggctccctct acggctccca ctcgctgaa gcctggggtt    14280 accgcctgaa gctccagaag ggcgagtacg cggctgagtt caaggcgcgc atggggggacg   14340 cttacgaggg gggcatggag tggcgagagc tttctcctga gatgctcgac tactgcgacc    14400
tggacgtgga tgtcacggac gcactgttcg accggatcga aggcaagaac tactccgcgg    14460
aggcgctgga gcttgagcac cgcatcgcct ggctgatggc tcaacaggaa cgcaatgggt    14520
tcccgtttga cgtgacgaag gccagcgcgt tgtacgccaa gctcgcgcaa cgccggggcg    14580
aactggagcg agaactgaaa gagttcttcc gtttctggtt cgctccggct ggaacagtga    14640
ctccgaaggt tggaaacaag gcgcgaggaa ctgtagccgg tgtcccgtac accaaggtga    14700
agatcgtgga gttcaacccc ggctcccgcg accacatcgc taatcgcctt gtcacgctct    14760
acggctggaa accggaggtg ttcaccgatg gcggtaagcc tcgggttgat gaagatgtga    14820
tggcacgcct ggactacccg cccacgaaac tcctcacgga atacctgctg gtctccaaga    14880
gaatctctca gctagctgaa ggtgaccaag cgtggctcaa ggttgtacgt gacggaaaga    14940
ttcatggctc cgtgaatccg aatggcgcgg ttacaggaag atgcacgcac gctttcccga    15000
acgtggccca ggtgccagcc gtaggttccc cctatggtga ggagtgccgg ggattgttcg    15060
gggcacctaa gggttggctg ctggttggct ccgatgcttc cggggttggag cttcgctgtc    15120 tagcccactt catggccagg cacgatggcg gcaagtatgg aaaggtgatc cttgagggag    15180
acatccacac ggagaatcag aaggccgctg gactgcccac acgaaacaac gcgaagacct    15240
tcatctacgc gttcctctac ggagccgggg acgccaagat tggtaagatc gttggtaagg    15300
acgctgctga aggaaagaag ctcaaggccg cgttcctgaa gaagacccccc gcactcaaga    15360 agctcctcga agctgtccgt gagtctgcca agcgcggcta cctggttggc ctcgacaagc    15420
gacaactcca tgtccgctct cagcacgccg cattgaacac cctgctgcaa tccgcaggtg    15480
ccctcatctg caagtattgg gttgtccgca cggcagagcg aatggaagct ctgggctaca    15540
agcacggatg ggatggggac ttcgcgttcg tcgcctatat ccacgatgag cagcaggttg    15600
cagtacgaaa tgaggaagtc gccaaggtcc tcgttgagca ggttgcattg gccatgaagg    15660
acgccgaagc gtgggccgga ttccggtgcc cgctggcctg tgagtccaag gtcggtacgg    15720
attgggcttc aacacactaa agtaatcaga caccaacatg agcatgttcc gagacgacct    15780
actcaaagaa gtcctctacg aggcgttcaa gactcccttc aagctccagt ccgacttcgc    15840
ccgagagttc gctcaggaag tcgccgctct ggcctcgatg ggatacatct cgacctacga    15900
ggggccgcag cagttcggca agaagtggcg cgtcaccggc atcggcctgg acaagctgcg    15960
caagctgggg atgctgtgag tgaagcccta cgcccccatt cgctgaggat catgggccgg    16020
aagttccggg tctcttacaa ggatgacctg gacggtgacc tgggatactg cgaacccacc    16080
aagtgtaaga tcgagattga gaacgggcag caccccgtgg aggaggccga tacggtcctc    16140
catgaggtgc ttcacgcggt gttctatctg atggacattg ggctctccgc ggaggaggag    16200
gagcacgtgg tccgtaaggt tgtcaccgga ctcacccagg tattccagga caaccccgg     16260 ctcctgacct acttggcaaa cgccaagtga tggaccatat agccaagttt gattctctcc    16320
aggaggaact catgacggac aagaagtgga ccatcacggt taacgtggac accccgagg     16380 gccaccggga gcggaccatc gagttccccc accggcccac cgaggaggag cttggtctca    16440
agctggcgca gttcttcagc cggatgaact tccgattcaa cgaacacctg aaggaggtga    16500 agggggtgtgc gctcctgaca cctcggagac cgtatgaaag tagcgctgat tgatgctgac    16560
```

```
gttctggtct tccaggcggc tgtagtcgct gagaaggcaa ccgattgggg ggacggtgtt   16620
tggaccctcc acgcagacga gggtgacgga gaacgaatcg ttcgccagtc cgtcatcacc   16680
ctccaggaga agaccggtgc ggataaggtc atcctggcat tctccgatga ggagaactgg   16740
cgcaaggcca tactgcccac ctacaaggcc aaccgagcgg gttcccgcca gccgatcatc   16800
cgcgcgcatc tgaagcggtg ggcttccgac gaatacgaga gcttcacccg gccaaccctc   16860 gaagggatg acgtgctggg catcctggcc acccgcgagg gcaagccagg cgagaacttc   16920
atcgtgtgct ccatcgacaa ggacatgcga accatccctg gcacccactt caacttcggc   16980
aagaacgaag agttcgtggt gacggaggag ggggcagact actggcatct cttccagacc   17040
ctcacgggtg accggtgga tggctacgca ggctgtcccg gcattggccc ggtggccgcg   17100
aagaagattc tcgacaagag ccccacctgg ggtgccgtgg tctctgccta cgacaaggca   17160
ggcttcggtg aagaggaagc tctcgtgcag gcccgagtgg cgcgcatctg ccgcgctgaa   17220
gactacgact tcaagaagaa acaagttcga ctgtggaccc caaagaaatc ctgaaagaac   17280
tggaacagca gcaacgccgc aagttcgaga aaggccctct caccggcaaa cgcgccgatg   17340
tcatcatcat ggacgacatc caggacacca aggacaccaa cccgaaggac gccatcggct   17400
ccaccaagct ccccctcgac ctcgttcctg actcgctctc ggtcttcgcc gcgctggcgt   17460
tcaccgaggt gccaccaag tacggtgcct acaactggcg tgtcgctggt gtccgtgcgt   17520
ccatctacaa ggccgcgctg gagcgtcacc tgaagaagtg gtggaacggt gagtgggccg   17580
acccgaagac gaaggtgccg cacctggcca gcgtcatcgc gtgtgctgcg atcatcctgg   17640
acgcggacct cgcaggcaag ttgacggatg accgccctcc ggcaatcgac ctgagttcct   17700
tcatcgactc ccttgaggag accgtgaagc acctcaagga actgcacaag gacaagaacc   17760
cgaagcacta caccgaactc aacgtatgaa cccgaagcga aacactctga ccggctgggt   17820
catctatgat gcagagcggg cgactggccg aagcaccgcg attgcgctga gtcttctagg   17880
caaggccatt gcaaatccag gtgtggccgt acaaatccga gaacatcacg gtactcgtcc   17940
ggctgacgag agtctgatgc gcctgatgcg ggatatggtc tttcggctgg gcctcaaggg   18000
catgacgttc agccagaacc tgactgtgac gttcaacctt tgggagcctg tgtgagccag   18060
agccgaaagg gctctctcat tgaggccctc atcaacaccg caatcggctt cgggatcaac   18120
ttcacggcga acctcatcat cctcccactg ttcggcttca ccagtttgac ggtgcagacg   18180
aacctggtga ttggcgtggt ctacacgctc atctccgtgg tgcggagtta cgtggttcgc   18240
cgctggttca acgcacacat cgtccgagcc gccaagaaac tctcaggggc ctgaaggtct   18300
ctttaggttc cacaatagga gaatcaaatt ggcgaacgac aagtttccgc cgattcccaa   18360
agaattactt gaggcgcttg agaagcggtt cccggagaca ccactcgaaa atatcgggtc   18420
tgtggatcaa cttcgattgg ctcagggtga gctacgtgtt gtccggtttc tccgagccca   18480
attcgagaag cagaccaaga acatttttgga gaacacatag tgtgcatgtc tcaaccgtcc   18540
gccccacctc cggccccacc gccaccgcca cctccgcccc cgcccgtcga tccgattccg   18600
gtccaacctg cgcagcaaac cggtggagcg gtgaccagcg gcaagagcaa gggacgcgac   18660
tccctccgta tcgacctggc ccagaagaca tcggtggtg cgccggtct gaacatcccg   18720 atgtaacgaa gggcagggat ggaacaagaa aagaaaacct gcgcctccct ctaccagaaa   18780
ctcaccaccg accgagaccc gttcctgaag cgggcctacg actgcgccga actgacgatt   18840
ccctccttgc ttcctcgtga gggacacaac ggctccacca aactcgtcac tccgtggcag   18900
```

```
ggcattggtg ctcgtggggt gaacaacctc gcatccaaac tcctgctgac gcagcttcct   18960
cccggaactc ctccgttcaa gttgtcgatt gacgacttca cgctggagga actgacgaag   19020
caggaaggga tgcgggcgaa ggtagaggag gggctcaaca agatcgaacg cgcggttcag   19080
actgagatcg aagcgaacta catccgcgtg gctgccttcg aggcgctgaa gcatctcatc   19140
gttagtggca atgccctgct gtacattccg cctgaaggtg gactgagagt attccacctg   19200
gaccgctacg ttgtccgccg tgacccgatg ggcaacgtgc tggacatcat caccaaggag   19260
aacgtctccc gagacgcact ccccgacaac ctcgtcctcc ctgatgacac cgaggagaac   19320
caggagcccg cggctggtac gaaggatgtg gagctttaca cccacgtcta tcgccagggc   19380
cgcaggtgga aggtctacca ggaagtcaag ggtgtccgca ttcccggcac cgagggttcg   19440
tacccgctcg ataagagccc gtggattccc gttcgcttca cgcagatcga cggtgagagc   19500
tacggacgcg gttacgtgga ggagtacatc ggggacctga agagtctcga aggactctcc   19560
caggccatcg ttgagggctc cgctgccgca gcgaagatcc tgttcctggt gaacccgaat   19620
ggcaccacgg acatggctga cgtgtccgag gctgagaacg gtgcgttccg cgagggtgtc   19680
gcaactgaca tcacggtcct ccagcttcag aagcacaatg acttccgcgt tgctctggag   19740
accatgaagg acatcaccga gcgcctggcg tttgcattcc tgctgaactc cgcagtgcag   19800
cgcaacggcg aacgggtgac cgcagaagaa gtccgctaca tggcgaacga gttggagtct   19860
gcgctgggtg gtatctactc catcctctcg caagagttcc aactgccgct catcaagcgg   19920
atcatgtacc agatggaacg gcagaagcgt ctgcccgtcc ttcccgaagg gaccgtcaag   19980
ccaatcatcg tgactggcat cgaggccctc ggacgtggaa cgacctgaa caagctgatc   20040 cagttcgtcc agatcgccgc acaggcagcg aatcttcctc ccgagatcga caaggccgac   20100
ttcctcaagc gtgctggtac ggcgctgggg atcgacatga agggtctcgt gttgccgcct   20160
gaggtggtag ctcagaacaa ccagcaggcc atgatgatgc agatgatgca gcagggtgtg   20220
aaccccgcca tcacgcaggc tggacagcta atgaaacaag gaatgcagaa tgccgcgcaa   20280
cccgcaggcg ggcagtaagg ctcccgaggc caacactgcc gaagcccccg tggtcaccgt   20340
tgaagactcg gtggccgaac agcaacccaa gcccgcagcg aagccggtca agtgaccga   20400 actacctggt ggcgtgaaga tcgaagactt ctgatgagtg tggattccgt agtcatcaag   20460
cagccggacg ctccggtgga agaccaggcc cacatcgatg cgatggtggc caaggtggat   20520
gctgccaata cttcgaccga accggacact cccgggatgc ccgcagaggg acgcccgcag   20580 tggctccccgg agaagttcaa gtctcccgag gacttggcca aggcatatgc cgaactggaa   20640
ggcaagctgg gtgggaagaa ggatgatgcc actccacccg ctgacgacaa ggccgcgaag   20700
tctgacgaaa ccccggaccc aagcaaggcc acccaggacg atgcctcgaa ggctctctct   20760
gagaagggcc tgagcttcga tgagttctcc gctgagtttg cccagaaggg tgaactgacc   20820
gccgagagct acgagaagct ggagaaggct ggcatcccga aggccgtggt ggaccagtac   20880
atcgctggcc agcaggccct cgctgagtcg taccgcaagg acgtgacctc ggttgccggt   20940
ggcgatgaaa gcttcgctga tggtcaca tgggccgctg cgaacctctc gaaggaagag   21000
atcgccgcgt acaacaaggc cgtggactcc ggtgacatca accaggcgaa gctggtcgtg   21060
gccggtgtgt accagaagtt cgacgctgct ggccgcggtg gtgagcctgc cctggtgact   21120
ggcgctggcg gtaaggtctc gggcgatgtc tatgagtccc tggctcagat gcagaaggac   21180
atggcctcgc cggagtacaa gaccgacccc gcattccgca agaaggtgga gcagaagatc   21240
gcccgctcga acatcttgta aggaaccatc atgatcctgg agagcatcct gggttcggtg   21300
```

```
gtggtccccg ctatcatcga cctcgtgaag ggtgctggtg gggccattag ccgcaagttc   21360
tttggtctgt cggttgacga ccagatcaag attcaaaatg ccgacatcga gaagctcaag   21420
gctctcgctg ccctcgacaa tccgtatggc accccagcc agtgggtggt ggacctccgc    21480
gcatcgttcc gatacatcgg cgctgccgcg gtcatcgctg tcggctgtgt caccctgtat   21540
gccggtgtcc agaccaacat cgaagacgtg aaggagatgg gtttcgccct cgtgggcatg   21600
cccttcggtt tcatcttcgg tgaacgcctg tacctcggcc tgaggggcaa gagcaagtaa   21660
gcactgccgg gaagcagcgc attctgtacg gttctgatcc cgtaaccgtt acccacggga   21720
tcacactgcc attgaagtga aggtcctag ccgcactgcg ctcctgcgcg gtggctctgc    21780
tgcatccaaa gaacaccaca acagaacctt ggcccgctga ggcggacaac cctgtgtgac   21840
gtgtgagttc ccggaagccg ctcaacacga ctttcaactc acttccaaaa caaaaatggc   21900
aaacgcagtt ccgtctcgcc tgggccaggc aaacctggca ggcgatccga aggccctgtt   21960
cctgaaggtc ttcgctggcg aagtcatgac ggccttcgct gaaaacaaca tcgtacttca   22020
gtacgtccgc cagcgcacga ttagttctgg caagtcggct tgacccaacc ttatgaactg   22080
ggccgactct aaacaccccg taaattcggt ggaaccccat gggggcaata ccgagccaag   22140
acttcgcagt acgcgagatg gtgtagagac tagacacggg gaacccacaa agacctgcgc   22200
atgttgcaac gtcgagaagc ccgcccgtga gttctataaa aaggacgcac agacaggaag   22260
gctcgatgga atttgcaagt cctgccgaat catcaagacc cgagagaaaa ccttaggggt   22320
cactgaagat gactatcggc ggatgtatca tgtccagggc ggtcgatgtg aatctgcca    22380 acggcgcttg tactcaaaga ggtacaagag ttttgcagtg gaccatgatc acgagacagg   22440
aaaagtccgt ggcttgttgt gccataattg caaccgcgga ttaggcatgt tccgagacga   22500
cccgactgcg cttaggcgtg ctatcgactg ggttaaggta tagtccgatc ctcacagcaa   22560
tgtgagtagg ggaagcagtt ccccgtaatt ggtaaggcta ccgccgcgta ccacacgccc   22620
ggtaacgaaa tcaacggcag caacatcgcc cacaacgaag tggtcatcac catcgatgac   22680
ctgctgctgg ccaacacctt catcgccaac atcgatgaag cgatgaacca ctacgatgtt   22740
cgttcggtct attcgagcga actcggcaag gccctggcca accagcttga ccgccacctg   22800
ctgcaactgg ctgtcctggc cgcccgctct gctgcccgta tcacgggcga acagggtggt   22860
tcggtcatca ccgatgctgc tgccggtacc gactcgaacg cactggtcgc ggacatcttc   22920
tccgcggctc agaagctcga tgagaaggat gtcccggctg atggccgtgt gtgcttcctg   22980
cttccggccc aatactacgc cctggcacag aacaccaaga ttctgaacaa ggattgggt    23040 ggtgccggtg tgtatgcgga tggcaaggtc ctccgtgtgg ccggtgtgga gatcgtgaag   23100
acgaaccacc tgccgaacac gaacatcgct tcgggttcga ccgcggctgg tactggcgat   23160
aagtacattg gcaacttcac gaccaccgtt ggtgtggtca cccagaagtc cgccctgggc   23220
accgtgaagc tcatggacct ggcgatggag tctgaatacc agattcagcg tcagggcacc   23280
ctgatggtcg ccaagtacgc aatgggtcac ggcgttctgg ctccgcaagc ggctgtcgaa   23340
atcaagaccg cataagcgtc ccctcaagcc tcgggaggtt ctcttcaaga gttcctcctg   23400 gggcttttttt ttctgctctc aaggatcacc aattggcaac caagactcaa actgatcgcg   23460
ccaaggacgg tcaggatttc ttccagcttc cggcctacaa ggacacgccc acggtcaccg   23520
tgaatggcac cgtccgtgct cgcacgactg tctcgagtgg cgtccagctg caacccctg    23580 cggctcagga tgacatcgta gcgatcacgt tcaactcggc tgaccctggg aatacccgcc   23640
```

```
gcgaggtctt caccccggcc actggcgcaa ccatcacacc caccgagttc tgcatcgagg    23700
cccgcattgt acccgcaggc accattgcgg ccctcaccat caccttcccc ccgaacccct    23760
cgaaggaagg ccagcagttc cgtgctgtca ccacgcagac catcaccgcg gtgacctgga    23820
ctggtggctc tcgtctcaac gctcccacca cgctagccgc tggccgtgct gccaccttcg    23880
agtggagcgt ggcgaagcag gagtgggtct tcatcaacta aggaaaacgc atgaccacca    23940
tcgtcactcc gaccacggag cttgaggcgg tcaacctgat gctcgatgtc atcggggaga    24000
gcccaatcag caccctggag aacagcgctg tggtggacgc ggtgaaggcc aaggcggtcc    24060
tctccgaggt gtcccgcgct gtacaaacga agggctggca cttcaacacc gagaagggot    24120
tcgagctagt ccccacggtc ttcgagaagg agatcatcgt ccccgccaac tgcctgcgca    24180
ttgatacggt ctaccgggac gagggcatcg atgcagttca ccgtggcact cgcctctatg    24240
accgccgcag gcacacctac cagttcgaca agagtgtgaa ggtggacatg gtggtcaacc    24300
tccaattcga ggaactcccg gaatccgccc gccgctacat cgccatccgt gccgcacggg    24360
tcttccaggc ccgcatagtg ggctctgaga gcctctacca gttcaccgca gaggacgaga    24420
gggacgcccg agcggacctc aagaaggctg agggcatcac gggggactac aacattctga    24480
cggacagctg ggctgttcgt cgcgtcatcg atcgctgata tgcccctcgt ttcttcttcc    24540
atcgccaaca tggtgaacgg ggtctctcag caacccttca cgctgcgtct cgcgtctcaa    24600
gctgagttgc aggagaacgg cctcagtacc gtggctcagg ggttgaagaa gaggccccca    24660
accaagcaca tcaaacgcct cggcagtgcc atcaccggct ctgcctacat ccacaccatc    24720
aaccgtgact ctgtggagcg gtatgaggtg gtcatcacga acggtgacct gaaggtctac    24780
gacacggcag ggaaccagaa gacggtgaac ttcccgaatg ggaaggcgta cctgaactcc    24840
acggaccctg ctacgtcctt cagggccgtc actgtggcgg actacacgtt tatcgtgaac    24900
aagaagactg tcaccgcggc cagtgccacg aactccccaa cgcggccctt cgagtccctc    24960
gcaaacgtga aggttgggct ctactcgaag acctacacca tcaccgtctc cggtgtgggc    25020
acggccacct atagtacccc cgatggcacc gttgcggccc acgcggcaca gatcaccacg    25080
gactacatcg ccaaccagct tgcgaatggt ctcattaccc tcggtggatt cacctcagtg    25140
aaccaggtag gctccgtcat ctacatcgcc cggcccaccg attacaccat ctccgcaaca    25200
gatgggtata caacgcggc cctgaacgtg attaagggga cggtgcagag gttctcggac    25260
ctccccgcga atgcgaactt ccaggacttc actgtggaga tcgcagggga caacacctcg    25320
gagtccgata actattgggt caagtttgac aagaccggga caactccgg tgtctggcgc    25380
gagaccatca agccaggcat ctcggttggt cttagtccca gcacgatgcc gtgggtactg    25440
gtccgtgagt cggacggcac gttcaccttc aaacccatct cctggacgaa ccggctggtg    25500
ggtgatgaag actccgctcc acacccatcg tttgtgggcc gcaccatcca ggatgtgttc    25560
ttctaccgga accgctgggg cttcctcgcg gatgaggcgg tggtgatgtc ggaggctggc    25620
cagttcttca acttctaccc gaccacggtg acgcaactcc tggattccga ccgcatcgac    25680
gtatcagcat cccacacgaa agtctcgaac ctgaacttcg cggtggcctt caacaaggac    25740
ctcctgctgt tctcctcgca gactcagttc tcggtggaat caggtgacct cctgacaccc    25800
aagagcgtct ccatcaagcc caccacggag ttcgagtgca gcacccttgc gcctcccgtt    25860
gggattggac gcaacgtcta cttcgcggtc cctaagggtg agttcgaggg cttccgtgag    25920
ttctacgtag cggacaacgc aggcaccaat gatgcggctg agatcaccgg ccacgtcccg    25980
aagtacatcc cgaagggggc ctacaagatc gctgcggctc tcaacgagga ctttcagggg    26040
```

```
aacccaacgc gatgtatgcg tacaagttct actggaacag caacgagaag ctccaaagct    26100
cctggtccaa gtggaccttc ccgagcacgg acacgattct ccacgcggag ttcatccagt    26160
cggaactgtt catcctcatc aaccggcccg atggtctcta cctggagaag ctcagtgtgg    26220
ctctcgggga catcgggacg aacgagccct acaacgtcca cctggaccgc aagctgacgg    26280
tgccgaaagc aagcctcacg tatgacggca cgtacaccat catctcctcc gcggctctcc    26340
cgtggaaccc aacggatgga acgtacacgg cagtggtggc caccagtcag ccgcagaagg    26400
ctggcgtcct ctacccggtc atttgggatg ggacgaacgc caagattctc ggtaaccgtg    26460
tggactccga cctcatcgtt ggtaggcgct acgccttccg ctatcgcttc tcgccgctac    26520
tggtccgcca gcagtccggc cagggccaga aggcggacac ggttgcacgt ctccagattc    26580
gcaacatgca agtcaacttc tcggagagtg gcaacttcca ggcaaaggtc acgccttacg    26640
ggcgggacac ctacacgtac acctactcag gaaagaccct cgggctgcct tcggcaaaca    26700
tcggggccat cggaattgaa gatggcaagt tccggttccc ggtgatgtcg cagaacacca    26760
ccgtggacat cgaactcttc tcggactcgc cgctcccctg cgccttcttg agtgcagatt    26820
gggaaggcta ctatgtccga cgaagccagg cggtctaaac catacgtccg tcctgcaaca    26880
cgcgaagact gcatcatcct cgcaaggaac ctccgacagg aagacgcgga ggagatcgct    26940
catgtgaacg gtctccccgc ggagatgaat ctcttgctgg ggttccgcac ctccgctcga    27000
ctttatgcgg tggtgtgggg ggatgagacc gtggccgtgt tcggcatcgg gggagtgcct    27060
ggcgtcatcg gcttccctg gatgctcgct tcgccctccc tctcgaaaat ccgcaagagc    27120
ttcctgaggg agtgccgcgg gtacgtggag gggatgctcc aggagtatcg ccacctggag    27180
aactacgtgt gggcaaagaa cgaagtccac atccagtggc tcaagtggct ggggttcgag    27240
ttcgagccag cagcaccatt cggtatcaat gacgaaccct ttcacagatt ttataggagc    27300
atgtgatgtg cggaccagcc gcagttccaa tcgccatgct gggtatcagc gctgtgggca    27360
ctgccgcttc gattagcgcg cagtcgcagc agcagaaggc acaggatgcc ttcaaccagc    27420
gccagtatga aaacgacatg accgcgtacc gaggcaacct cgccaacatc gaggtgcaac    27480
ggaaccaggc gcgggaagat gcagtagcgc agaagcagca gaacgacatg gcaggaaggc    27540
gcgcaacagc aaccgccacg actgccgcag gtgaggcggg tgtctcaggc gcctcggtgg    27600
atgcactgct gcgggacctc gctggccagg ctgcctacga caacaccaac gtggatgaga    27660
actatctgcg ccaggacagg gctctgaacg cccagcgtga aacgccttc aacagcactg    27720 caagccagat caaccagctt cgcccctcga tgtcccggga ctatctcggc gctggtctcc    27780
gcattggcca ggctgctgcg ggtgcttaca gccagtacca gcagaacctc gactacgagc    27840
ggaaccagag cgtcccacgc cgaggagcat aaatggcacg agttcagaca gactatcgaa    27900
cccgaggtac agggcttcag gacatctcgc ccccaatgct tcagccgcag caggcagggt    27960
tagacaatgg tgccgctgag tctgccgcac ggctggccca ggcgttaggg gctgttgacc    28020
tgtctccgct ggtaaccgcc aagcgatacc aggatgtgga ggaggcggag aaggcacggg    28080
cctacgccaa ctccctcacc gtggaggagc ttgggaagca gatcaaggat gggaccctca    28140
tggcgtccca ttcgcctgtc ttcagggcaa cggtcgaaca catccacggt gagaacacgc    28200 tcaaacgtt cgagcgggac acactctcga agctcacccg cggggaactg aagttcgaca    28260
ccccgcaggc catggatgag tacctcacga agtaccgcaa cgaggccctc acgggatcca    28320
gcaagttcac cactgcgggc ttcgataagg gctacggcac gttccgtgag cgagccatcg    28380
```

```
cggttaacgt gaaggtggcc gatgaagagg ccgtgaagcg cggcagccag gaagcctcgg   28440
acaacctcgg caacctgacc ctgcaagtca ccgacccgat gtacaagggt gacgctgcgc   28500
aggccatcgt ggaccgctac cagcttcttc ggaagacctc tctgctgcgt gacgatgccg   28560
cgaaggaagc tctctcgggt gtcgctgcga accttgcagc ctccggcaac aaggccctcc   28620
tgggttctct gctggacaag aagttggaca gcggtgtctc cgtcaaggcc gctctggggg   28680
acctgaaggc catccagttc acgcaacacg ctgaacgtga gtatgaccag gcgcagcacc   28740
aacggattga cgttgagatt cgtccgttcg tggagcaggc cgacaagggt gaactgaagc   28800
gggatgcctt cgacaagtgg ggggccgcga atgagaagta cgtcaccacc cccaccatcc   28860
acgccatcat caagggcaac gaggcggcca tcgagcggca acagaagctc atcgctcaga   28920
acgccctcct ggcccaggcc gaagcaacac aggctcaggc aacgcaggca gcccgcacgg   28980
ccatcgacca gggcaacctg gcgttcctcc cgcagcagaa ggtgatgaca cctcagggg   29040 aacagaagaa cttcgatacg aaggccgctg ctgtcccgta catccaggaa cggattgcac   29100
gggagaacat gccgttcggt aagcaggtgg agttctggtc caccaacggg gtggagaatc   29160
ccgagtggga gaaacagatc aagggtggcc tctcgaacct cgcctccgcg ggctggacct   29220
tcgatggcaa gaccattggc caactgaaca accagggcca ggccgcaatc gacaccttca   29280
tccgcatcaa cagcaccaac cccggctacg ctgagaagtt ggtgggcggt gacaaggact   29340
acaagaagct ctccgacatc cagttcctca tggagaaggg cggcttcccg aacgtcaacg   29400
atgctgcggc actcatcaac cagattgacc gcgctgacat caaggcatcg gactacggtt   29460
cgatgaagca gaaggtggcc tcctcggtgg acgatgtggt gaaccagcat tggtactcag   29520
gcgccaccag ttggttcagt ggcctcttcg gcaatgacca ggtgaacctc accgctgtct   29580
ccgctgacat tcgccgcagg gctgaactcc tggtgatgtc tggccaggtg cccgatgcga   29640
acgccgcggt gaaggccacg gtggaatacc tggcgaaccc cgcagtcacc acgcggatca   29700
acaatacgct ctacttcaac aaggaccttc cggtggtccc gaagggcgag gacaccgggc   29760
agtggatggg gcggttcatc aaggacgttc cccagcagat cgccaaggcg aacaacctcg   29820
gtgatgctcg cctggagccg aaccagtacg gaggcttcac ggcctggact ggtggtgtcc   29880
cgatgacgga cggcaccggt aaggtggtca cctacacgcg ggatgacatc tcgaagtggg   29940
tggacaacac catcaccgct gaccgccaca aggccgctgc tgatgccaac ttcaagagct   30000
accaggaccg cctcgtgaag gaactccgcg atgaaaagca gaaggacccc tacgtgatgg   30060
agcggatgtt cgacgcgact gccaacggca tgtggtggaa ccgccaactc tacagccgcg   30120
aaggctatga gcaggttctc cgtgacggca acacaggcaa gccgctcaac gaactgttcc   30180
aaatctacaa agacaaacgc ttcaaggata agtaatggcc gcatcgatcg ctctggggga   30240
tgtccagagg attacctccg agacggagaa gaagtacggg ctccctgaag ggacgctgtt   30300
caagatcgga aacatcgagt cctcgttcca ggatggccag gtgagcccga agggagccaa   30360
gggctacttc cagttcaccg atgacaccgc aaggcgctac ggcctggatg atccgttcga   30420
cttcgagaag tcatccgatg ccgcgggccg gtacatgcga gacaacctgg ccaagtacca   30480
gggcaacatg gacctgtccc tcgcggacta caacggtggc ccgaaggccg ctaaggctct   30540
cgccaagggg aagccctggg cagagacttc ggactacctg gcgaagttct acggcaacaa   30600
gtccgagccg ctctcgcagc aattcaccac gggctccgaa gtccctctta ctgcctcccc   30660
ctccgcctcc cagctctatc gagacgcacg gcagcaggag tctgagtatg gaggggttgg   30720
caataacatt ctcaatctgc ctcgtgctat tggcctgggc tttcaagtcg ataattcggt   30780
```

```
ctacaatttc tggcaggagc gaggactctc cagcgtagac cccgacttcc gctgggacga   30840
tgacttctcg aagcagatgc ttgatggggt ccctgagcgt cattgggat acctgctgca    30900
atccaagtcg aagcaggaag cggaactccg ccgtgcccgt ctgttggaca cgatggagaa   30960
ggaagtcgaa ctctccaaga tgggtgtggc cggtttcggt ggtcgcctgg tgggcaacct   31020
ggtggatcta cctacgctca tctcgttcgt ccctgggttc ggtggtgcgg gcctcctcac   31080
gaccacttca cgcatcgcca atgctgcccg catggctgcc ctcggtgctg ctacgaacgt   31140
agccttcgat gctgcaacga tgcagttccg ccccacggcc accccggatg acctctacat   31200
ctccgctgcg atgggcctgg gtctcggtgc tgctggtggc ctctcggtga atcctgcccg   31260
cctggccgcg caacgtctcg ctgctgagaa ccgccgcctc ggtgagttcg gtctccgtga   31320
atccggcaag gcgcagatca aggagcttgg cgacaacggc ttcaacttcg gtgctggccg   31380
tgaggagttc gcacggcgca tccaaggcaa gcccgatgag ccggtggaga tcaagtaccc   31440
aggcggtgca atcgtgctgc cgcggggcga tggtgagcct ccgaagattt tccaccctgg   31500
tgatccccct gaggttcgca agccagggaa catcaacgag ccgcttcctc ccgaagctcc   31560
tccagctact cctccggcca ccggcccggt tgctcccaag gctcctccag cagaggcacc   31620
taagggcaag ggctggacct ccgagtggga cactccgcgg tacgcctcag gcggtggcaa   31680
cgagcaactc ctcgtgctgc ctccggcaaa gcgtgtgagt cagttggctg agtatgtccg   31740
ccagttctcg aagaacgggg acatcgtgaa ggtgatggac cgggtgctga agggcatcga   31800
cctccgcaag ttggagttca aggtcatcga gaagggtcag cgtttcggcc agcgtgacat   31860
ggacaacgaa atcctcggcg cgaagggcgc tgtaggtact ccgcgaggtt ccattggtga   31920
caacatcatg atgttcctgc ggggccactc gtgggagatg cctggtgtca acccgatgca   31980
cacggtgggt ctcaacgagg agacgttcgt tcacgaactc gttcacgttg ccaccatcta   32040
caagctccgc ggtgttgagc ctggcatggg tgtacgcatc acggaccctg ttgtgcgcag   32100
ggctgctgat gacctggcga acctccacgg ggacatcctc gaccacgcca ggcaaaacctt  32160
cggggccaac tggaaaggtg aactccaggg acgcctcggt gccaacctgg agaacgagaa   32220
ggaactcatc gcctatggtc tgacgaaccg gaacttccag gagtggctca agacggtgcc   32280
cgttgagggt ggccctgaga agaacctgtg ggaccgcttc gtgcattccc tgcgcaagct   32340
cctgggcatc ggcccgaagg aacacaacgc cttcacccgg ctgatcgaac tgtccgcccc   32400
tctcacgaag aagggcgact tcgttgagcg catcaagacg aacccagagt tggaagcaac   32460
gggtgggttt gttgacgctg acaccgtgaa ggccgcgaac gaagctgacc tggctccggt   32520
ctatggctgg ggtctcggcc tggagaacag gctgggtggt gctaaggctc cctccgctgt   32580
tcgtcagttg gcctcgaagc tgttcggcac caccatcggc tacaaggaca acgcggtggt   32640
gaagctcaac gcttgggacg acaccacgaa gtgggctgac tcctgggccg tggagatgcg   32700
caagggcacc tatccgcagt tcgaggagtg gctcaagggc tctcagtaca agtggcacga   32760
gaagggcaag gcgttcgatg acttcggcgc acaggtgtcc aactacatcc gcggcttcga   32820
gggtgattac ccaccgcagg tggtcaaggc tggcgagcac atgcgcaaga ccctggccaa   32880
cgtggtggac tacatcaaca gcccactgaa ggacgaaggc cgagccaaga ttggtctcac   32940
cgagacggac atccgagacc cggagaccgg caaggtggag cgggtaggga cgctggagaa   33000
gaacccgaac tacctcccgc gcaagcacga catcaacaag tggaactcga tggtctccaa   33060
cttcggcagg gatgccgtgg aagggtggtg ggcacgggcc taccaggctg gccgtgaggg   33120
```

```
aatctctgac gaggccgctg cgaagtgggc caagtggtat gtccgcacgg tggaggaggc   33180
tcacgccaac cgcactcagg acatgctcga tgacctcctg aagggcaccg atagggacgc   33240
cctgaagaac tccctgatgc tcaacggagg ctactccgaa gcggaggctc tgcggatcat   33300
ggacgacatg attcctggta gggccaccga tgcaggccgc acgatggcca gcctgaagca   33360
ccgcaacacc atccgggaaa cgcacaccga gcagtggacc acgaaggacg ggacgaagat   33420
ggaggtgagt ctgaacgact tcatccactc gaacgccttc gacgtggttg agccgtacct   33480
ccgcaggacc gcgggcagtg tggcgctggc caagcatctc gacatctaca agatggggga   33540
cattgaccgc gttatcgctg aggccaccgg caacaagctt gggcaggagt tcaagtccac   33600
ccccgatatt cagaagctcc gcaaggacct gaagttcgcc ttcgagcgag tccaagggct   33660 tccccctggag gagttctcca cgctgaacaa gagcctggag atgtggcgca acttcaacgt   33720
tatccgcctg atgggtggag cagtctggaa ccaggccacc gaactcagcc agatcatcgg   33780
cacgatgggg tggaagacta cgcttgcggc tctccctgag cttcgagcac tgcgccgtga   33840
catcgccacc ggcaaggccc gcatgacat cctggaccac ctggagaaca ccattggtgg   33900
cgtagggtcc gagtacgtgg cccgcctgga gttcaaggct ggtgacgatt gggtccgcaa   33960 caaggggac accaggttca accgctggct ggactctgct gacaccggca ccaggaagct   34020
ggcgaaaggt gtgctggatt acaccggcat gactccgctg atgattcagc agaagcgtgt   34080
ccacgcgatt gcgttggtga accacttcgt caacgtggcg aacggcaagg ctgctgggtt   34140
cctcacgaag gatcgcctgg cctggatggg tatgagcgcg gatgacttcg gcaaggtcct   34200
gtctggcatc aagcagttca ccaagcccgc tgatggtgag ttctcgaaga ccttcaagat   34260
ggacttcgcg ggctggcaga aggcggaccc ggagagctac tcgaagttca tgacggccat   34320
ccaccgtgaa tccgcagggg tcatccagga gaacgacctg ggctccatga tcccgctcat   34380
gggcaccacg ctgggcaaga cggtcttcca gttcatgaac ttctcgatgc acggctggaa   34440
caagtcgctg atgttcgcca tgaaccaccg cgactggtcc acactgtcca ccgtacttca   34500
cggctcactc ttcgcgtcca tcgcctacat ggggcggacg ctgctgggtg ccggtggcat   34560
ggaagcggac aagcgccagc agtatctcga caagcggatg tccgttggcc agatcgttac   34620
caacagcttc gggcgcatct ctcaggcgtc cgtgctgccc aacatgttcg acaccatctc   34680
accgtatccg ctgttcagcg gaatgcggac cacgagtgac ctctccagtc tggcatcgaa   34740
cccgacctac caggccatca acggactcat ctcgatgaag aagctgattc ggaatggtgt   34800
gtcggatgag taccaaacca cggagaagga catccgcacc tggggcaggc tactgcctct   34860
caacaacgtc ttcccggtga ccacgttcct gaaccacctg gcgaacgatt atccgcacgg   34920
cgaaaagcaa caataaacgg gtagccctcg gcacgaccgg gggcaacctc ttttggagaa   34980
tagatagtgc cttacagtta cgttcttctc tcggggaacg gctctgcgac caacttcggc   35040
ttcagcttcg gttatctcag caagttccac atcggagtga aggtgaacgg tgtagtcacc   35100
accttcacct gggtgacgga cttcaccatt ggcatcacac cggccccggc caacggtgca   35160
gtcatcgagg ttcgacggac gactccgttg aatcaacccg ccgtggactg gtcagatggc   35220
tccacgctca ccgaagcgga catggacctc aacactcggt tctctctgta cactgctcag   35280
gaggccgctg atggtgttgc agcatccatc actcagaact ccctggggca gtgggcggc   35340 cagaaccgca gggccgtcaa cttcgcagac ccggttgatc cacaagacct ggtgaacaag   35400
cgatacttcg aggacgtgta cacacctcag ttggacgcga aggtcaccga agccaccaac   35460
caggccaaca acgcggcctc cagcgccgcc actgcgcagg gctatgctct cgctgcggac   35520
```

```
aactccgcgg acctcgctgc ggccctcctg gcgaccttca aaggccagta cctcggtgcc   35580
cttgcatcta accccacgct ggacggtaac ggccagccgg tgactgctgg tgacctctac   35640
ttcagcacca ccgataacct gatgaaggtg tacaccgggt ccgcgtggat caacgctggg   35700
tcaaccgtcc agtccaccat caaacgtcct gtcacaccca tcgtggcaac cgcaggccag   35760
accgtgttcc cggtgtctgg tgggtacgac gccccataca ttctcgtgtt tgtgaatggg   35820
gttgaggtgg cttctccaga tgtggacgtg actaacggca gcaccatcgt attctccagc   35880
ggcctgactg ctggagataa agtggattac gcagcgtttg gtgcgttcca ggtggccaac   35940
ccggttatcg atgggaccag cgccgcagac ttcatcaaga cacgcaatgc ccgtgtagtt   36000
acctctattg ccgacctgaa ggccctcaat aagaacacct acaacttcgt tctcgtcact   36060
ggcttctatg cttcagggga tggtggcggc ggtttcttcc ttcaggttcc cacgatgccc   36120
accaacggta tcgttcaggt cgggaatgac ggaggcatct ggcagttggt ggttgatcgg   36180
gattatgttt ccgcgaaaca actcggtgcg agactggacg gttcaacgga tgactcctct   36240
ctcctgaaca acgccaagtc cactctcgat gctcttggta agaggctgta tatcccgtct   36300
ggggtttgca gaatctcaac agcaatcact ccaccaaagg ctggtgtgtt tggggatagt   36360
cctcaagcgt ccatcatcca gtgtaacaac tgctctgcat tcctattccc agcaaatttt   36420
gggctctctc gtccggcttg tgtcattgag aagttgggga ttcagtccta cagcaacacc   36480
tgcgatgggc tatacgcttt ccgtgcccct ggggtggcat caggagcatc gcccgtctac   36540
aacagcggcc taactgttag ggatgttgag attggtacgg gcggacgatt cggtggcggt   36600
ttctcactga aggacttctt ccgagtgaac gtagagaaca ttggcatgac tgatgtgagt   36660
tccgccgtat tgctcaccgg gtcagttgtg caggcagtat tccgaaatgt caccgcaaac   36720
ggtgataacg caccaactgt tcttaaccgg tatggtttcc aaacagccgc agcttcctat   36780
tccagcggta cgctaggtcc tgaacacatt agtacgtggg attgcagctt cattcgctat   36840
acacgcggtg ttcaacacga tgctgggctc atggtctcgt tcaacaatac ggacctggaa   36900
actttcacac acggcttcta tctctcgcag ccctgcactg tgcgtggtgg tattagcgcc   36960
ccggctccgg cagcttcagg gactgctgcg tggattgggc ttttcaaagc tatttctgat   37020
tttgacgtag ccaacggcac tctgatcgat gaccttgaga tcaacacgct aaacacccca   37080
ggaactccag cctcttcgta tggggttctc attggcaaca atgtgaataa gtgcgttggt   37140
actacaatcc gtagtcccag gattcgaggt aacactagtt caatggtcgg tgggattgtc   37200
gctaatctag ctggaggtga catcgttatc gaggatgcca tcatcaacgg cagtgtggtt   37260
actggaacta cggtgtctgt gagcaatgct tcctatgcaa gggttgtggg caatcgaagc   37320
gccaccggtg ggactgtaaa tggttccctg tcaatcacag ataacggtgt tggttccatt   37380
ggtgatgttc gtggaaatgc gtttgccacc attaccaaca ccctcaatgc ctattccggt   37440
acatggacgc ctggaacaat tcctaacgga acaccagcag caacaacggt ggccgtccct   37500
ggcgcagtgg ttggtgacaa agtagtggtc ggcctttcca gcctgaccgg atcggccaac   37560
tgcatcattt ccggctatgt gtcttccacc ggaaatgtgg ctgtcctgtt gtataacgtc   37620
tctggtgcat cacagacgat tccctccggg actctccagg taacagtcct caagtcgtaa   37680
tcaagatgtc cctctaggtt tcccctggag ggacttcctc tttcaaggaa aggtatgagc   37740
aatgcgctca acgtaagtaa gctggccaca ctcacggcaa cagaaatcaa agcataacca   37800
aacaagaagt aatcatgccg aacatcgaca aagacgtaca gaaggatgct ctgaaggagg   37860
```

```
ccctcacgga gtggctggac aagcagttcg ccacattcgg gaagtgggcc ttgcggtcca   37920
tcctggccgc tgccttctca gtcctcatgt acctgtacct gacttctcaa ggctggcacc   37980
gctgatatga ccgaaaagac caccgcttcc gaaaaggagc ttggcgaagt ccacaacgag   38040
atggccgcat ggtgcctgga catcctcaag ggaatcccgg tcaccgacaa agacggtaac   38100
ctcgtgattg aggatgggag agttgttcgt ctccctccgg ctcctgccta cctcaacgtc   38160
attcgccagt tcctcaagga caacgacatc caggctgaac ccgccaaggg ctcctcgatg   38220
ggtgacctct cggacctccc ggtgttcgag gatgacaacg ttgtgcctct caagtctcaa   38280
tcgaaataaa cgcgattaga ggccctcaga gcgattttaa gcctccaagg tagggtagcc   38340
tatccgggca cctgatcgcg tcctgtgggg ccatctcgca agccaagaat gaaaataaca   38400
actgccgagg tttcggcaaa acgctgcccg aagtgcggcg aagaaaaaca cctctccgag   38460
ttacacgcga atcacaccaa gagggacggc cacaacacca tctgcaagct ctgcatgaag   38520
caggtggcac gagactggcg caacacacct ccgggccgct ccaagcagat gtggacgacc   38580
tcaaagaaac gtgcggagga gaggggctgg gagttcaatc taaccccga gtggattcag    38640 gaacgcctcg aagctggcgt gtgtgaggcc accgggattc ccttggagat gtccgcggag   38700
gagttcaaag gctacggcca cttccgtcca tggacccct cactcgaccg agacgatcca    38760
acgaaagggt acacaaccga caacgtgaag gttgtgtgct ggatgtacaa ccaggccaaa   38820
ggcgtaagca tgcacgaagc cgtcctaaga atggcccgtg ccctcgtagc gaatgacaac   38880
taaacaacac ccagcacaga aagactttcg cgtctttatg ttcatggtgt ggcgccacct   38940
caatctcccc gaacccacac cagtccaata tgacatcgcc cactacttgc aacacggacc   39000
acgccgttca gtcatcgaag cgttccgtgg tgtaggtaag tcctggatca cctccgcctt   39060
agtttgctgg gttctgtgga acgacccaca gaagaaaatc ctggtcatct ccgcctcgaa   39120
ggaacgagca gatgccttct ctaccttcgt gaagcggctc atcaacgagc ttccgttct    39180 ccagcacttg aagcctaagg cggaccagcg agactcgatg atttccttcg atgttggtcc   39240
cgcaactcct gaccactccc cctcggtcaa gtccgttggt atcaacgggc agatcactgg   39300
ttctcgtgcc gacatcatca tcgctgatga cgttgaggtt cccaataact ccgccacgca   39360
gatgatgcgc gacaagctct ctgaggcggt gaaggaaatg gatgcggtca tcaaaccgct   39420
ccagacctcc cgcatcatct atctgggcac gcctcagacg gagatgtcgc tgtacaacgc   39480
tctccctgag cgtggatacg aagcccgcat ctggccagcg ctgtaccccg agcttcacct   39540
cgtggccaac tacaagggcc gcctggctcc attcatcacg cgggctctgg aggccgataa   39600
gagtctcgta ggtgctccta cggaccccag gcggttcaac gagactgacc tgttggagcg   39660
taaggcgtcc tatggacgtg ctggcttcgc tctccagttc atgctcgaca cgagcctcag   39720
cgatggtgac cgctacccgc tgaagatcgc ggacctcatc gtccagaacc tcaacccac    39780 gatgcccat gtgaagatcg cctgggctgc tgcacctgaa gtttgcatca acgatctccc    39840
cgcggtggcc ctcacgggtg accgctacta ccggcccatg tggacggacc agcagatgtc   39900
cgagtacacg ggctgtgtca tggccatcga cccctcgggc cgtggtgctg acgagaccgg   39960
ctacgccatc atcaagattc tcgcaggcaa cctcttcctg gtggccgcgg gtggactctc   40020
cggtggctac tcagatgaaa ctctggagac cctggcgaga ctcgctaaga cccaccaggt   40080
gaaccacgtc atcatcgagg ccaacttcgg tgatggcatg tacaccaagc tcatcactcc   40140
attcttcggg aaggtgggac acaaggtcct ggtggaggag gtgaagcact ccacgcgaaa   40200
ggaagcccgt atcatcgaca cccttgagcc tgtgctctcg actcatcgtc tcatcgttga   40260
```

-continued

```
ccagaaggtc atcgagaacg acttcaggac ggcagagcag gacatcaagt acagcctgtt    40320
ctaccagatg acccggatca cccgagacaa gggtgccctg gctcatgatg accgtctcga    40380
tgcactggcc atcgctgttg cctactggac ggagcatatg tccagggaca acgataaggc    40440
cgctgctgcg atcaaggaca aggcgctgaa ggatgaactg aagaagttcg ttcacggtgt    40500
ccttgggcgc aaacccaagc gaacctcgtg gatgtcctcg aactcaggct ccaggtgaca    40560
ttcggtgcca cataggaga accctacgtg ggttcttcgg gggcttcatc cgtagctgat    40620
atggatgcca cacaccgtgt ggactcggga aacctcagtg tgtggtgatg tagtcgctgc    40680
attctaggac acccgttagt ctccctattc ctcatctcta tggggggta ggggggctaa    40740 cttaggtgtt cctagtgttg atgatatagc cactgagatg tcaacctcag tgtcccttaa    40800
gttgtctctt agggttgcat taaggagaca tcatcaccat catctcccat aaggtcatcc    40860
tccccatgtt cactctacta gtcctcctct caggtgtccc cgtggtgttc cttctgggtc    40920
tcgttctgta tggcctgttg gacaactgat ggtgtccctg aagtgcccct tagggggaaa    40980
acttccgacg caaaaatttg aaagccccac tcgaaattcg acgcgggcag attccccccg    41040 tgcccctcc gcggccggc cctcgtggcc cctgccgacc cacctccggg caccctccag    41100
gctgtacgct ccgctga                                                   41117
```

<210> SEQ ID NO 3
<211> LENGTH: 40589
<212> TYPE: DNA
<213> ORGANISM: T7-like viruses
<220> FEATURE:
<223> OTHER INFORMATION: /host="Ralstonia solanacearum"
      /isolate="vRsoP-WR2"
      /isolation_source="Yator river, Alpujarras, Granada, Espana"
      /note="Genome of the isolate vRsoP-WR2"

<400> SEQUENCE: 3

```
gacaactgat ggtgtccctg aagtgccccc ttagggggaa aacttccgac gcaaaaattt      60
gaaagcccca ctcgaaattc gacgcgggca gattcccccc gtgcccccc gcggccggc     120 cctcgtggcc cctgccgacc cacctccggg caccctccag gctgtacgct ccgctgactc     180
ctggcacatc ttctggcaca ctctgccgta actccctgat tactaagggg atgcactagc     240
ttacgaagct actgcgaccc aataagcctc acgcatgagc actcactggc tcactcgtgg     300 ggctttttt tctattctgt ccccatttcc gcgcccccct gttcggccat cagtttgctt     360
tggtttctcc tagggtttcc cctaagtgtc tccttggcgt gcatcgctac gattctccca     420
acggcccact tgcggcccac cactggagaa catcatgcaa ctgcaatact tccgcgactt     480
ggcaatcggc acagcgttca ctatcgctgg cacgccctac gtgaagaaaa gcgcacggac     540
tgcgtacacc gctcccggcc accctgggca ttgggaaggc cgctggttct ggtttggtca     600
gactgaactg gtaatggcct aagggagcac accatgagca agtccgagc actcgcctac     660 ttcttcgctg caaccacgct cgcactcgcc tacgtgggcg caaggcagc acatgcggcc     720 atctcaagcc tcctcgtgat gcacctgcat tgatcccact cagaacaccc tccttggcgg     780
caaagccgct acagaagcct ccagatcaac gtctgggggc ttttttgttt gcccctgggg     840
ctgacctacc tgcgtcccac tgcgtggctc ctagggcttc ctatcgttcc ttcggagcaa     900
cgctcctgat atcggaacta ttgcagtgat tgaaaaatac aattgggcag tctccgatgt     960
ttcgtatgta attcggtctc accaggggga cacgcccctg aagacaaaaa agcgtgggac    1020
cggggcggac gccagcagtc agggacaacc cgagtcaatc caagagtaag cacattgcga    1080
```

```
gtccttccag tgtgctcatc actggagaga catcatgcaa tcattcaccc tgaacattgg   1140
ccttatcccg agcaagaaat cttcgcgtac cgctcgcatc actgcatcgg aagttaaggc   1200
cgcacttcgt ggcgctggct tcttcgtgtc gggctttcgc atggcccagt cggccaccga   1260
gcctaccgca gtggtccgcg tgatcgcacg tcagccaatg agctatcacc aagcgctcta   1320
caacgtgtcc ctggcgctgg tgcaggactg catcgcggtt gtccctgaca cggtacgggg   1380
cgcgttgatt ggcccggatg cggctgagtg gggtgagttc aatccggcct acttcatccc   1440
gtttgatgtc gaaccgcagg caatcgctgc gtgacactta gggtgcccct tcaggggctc   1500
caggagtagc cgcattgcgc tgtgcagtgc gcctatcact ggaggacaac atgtacggaa   1560
actttgaccc gagcacgaac gcatggccgt tcagtgtgga gtttgtggac gctgtaggct   1620
ggcaagtgga ggcaaccgg gaccccacca atgtcgcggt gatggtcgct ggtctcacct    1680
tcgaggaagc caaacagcgc gcgtctgaac tcaacctgaa ccacttccgg gggtcctgac   1740
atgccgactc tcaaggaagc gagcgtgaat gctcagagac cacgcggagg cgtccaagcg   1800
tggagcgtag gggacaccta cccggtcact gtagtgggcc tgggcaatgg ccccgcgtg    1860
caatggtacg cggagaacct gcacacgggc gaacgtggcc ccgtgcgaga tgcccagggt   1920
gatgcagtgg tggaccagta tcgtcttggg gcggagttca acagaaatcg cctacaggcg   1980
taattcggtg gccctgttca tgtgtcgtga acagggctcc aggagtgaac gcattcaatc   2040
gtgagtgcgg tcatcactgg agaatgcaac atgcaaacga agaacagcg catcgaacta    2100
atcgccgcga tgtttggtga gcaagaaacg ggcctgatcg gtaagcaact ccgcgtgctg   2160
gataactccc aaagcggggc gttctacaat gttggtgatg tcggtaccgt agtcctcgtg   2220
gacgatgacg tgaaatctg ggtggactttt ggcccggatg gcttcaaagg cgatggtacg   2280
gcatacccgg tctgggccgc tggttcgctg ggcgcagacg accatgagtt tctggaaaac   2340
tgacatgggc gtcatctggc acgaactcat ctacgccctg ggagccctcg tggttgtcgg   2400
ggtcctcatt ctgatcctca ccgagggaga ctgacatcat gcgcacccttt gcaatcgact   2460
tcatgctcaa cggcaagcgc gttgggcgtg actacgtgac ggcttccaac gagaagcaag   2520
ccaccatcat cgcagaacgc actgcacccg tgacgctgta tgacgaggtt gtggccgcac   2580
cgctgtgatg gaccatcggg ctcccttgtg gagcccccag gagtggaccc tttcaattcc   2640
gagagtgtcc atcactggag agaatcatgt cggacaaagc caagcaatcc atcgagttcg   2700
ttcgcaacgg cctgggcgag gaaaacttca acaagctcct gagcatcacg ggagtacgtg   2760
acatcgaact ggctgccgcg ttcctggcga ccaccaagga ggagcgcgac tctgtgaaga   2820
caggtgacga cctcatgcgc ctgctgggcc gcaagcacgc tgagaaccgc gtggccatgg   2880
ctctggtgcg cgcgggtgtg ccggtggagg atgccgtgtc tttcgtgcgt gaaaccgctg   2940
ctagcctgta agccccaagg tgcccttag ggggcctcta ggagtgagcc gctggaatcg    3000
tccgaagtct catcactgga gatcgctatg tctgcacaag ccaaacaaac ccaaaccgcc   3060
ccgaccatca tcgccctgct gtctgctgcg aatatggctc agacgggccc cggcgtcttc   3120
gctggcgtca tcaaccaagc cacacctgag gagcgcgcgg tgtgaagaa catgaaggac   3180
ctcctggcgc tgtacttcaa ggttcatgcg cgagtggtgg ccgaaatctc gcggaagtg    3240
gaagccacca cggaccatcg ggctcctctg gtggacctgt ccgacttcgc tgagaccctg   3300
gcggagtact tcagccgtgc cgatgaagtg gtgccggaag cgtcacgct gcaataacgc    3360
tgggtgcccc gaaagggct ccaggagtgg atgtcttcat tgtgaggacc tccatcactg    3420
```

```
gagaaagcaa tggcacagat gcgcgcctgg gtctacaagg cgcactggag gcggcacctg    3480
gccgcgcaag gcatcgtcct gcgcaaatac gaggtggaca aggagtacat gcaccgcggc    3540
atgacgcagg ccatcttccg ccgcaacaaa gcgaagttgg tggccgagta cacggagttc    3600
tgacatggac atcgtagacg aactggagat aggaccctct tacgccctga actcggacga    3660
gaagtggctc cgcaagagag ccgctgagga aatccgcagg ctccgaaagc aactggcgga    3720
cgctggttgg gctctcgaag cggcccgtga actcgaagac caacgagaca acggggggctg   3780 gctatgaaac ccgctgacgg tcaacccaag cgcttcaagc tgcacaccaa gtatcccac    3840 aacaggtccg agggtttgac tcatcggacc aacaagggga ccgcgcttca agttctaccg    3900
aagaggtaac gccatgaaga tcactctgac actggaggac accgctgatg gtgtcgctgt    3960
gaactggacc gaggagcaat ctgaagctca gaacaaaccc agcgagagcc tggccaccat    4020
catcgctgcc aagttcattc ttgagataaa tcaatctcac cgtatgggaa ttttacggct    4080
gtccggcact gcattgggcg cagatcgcgc atagctagta tgaggtgtgt tgcgtagagt    4140
gcgaaccagt tttatttggt tcgccatgcc cgcatccaga agctcatcgc aacagtagag    4200
gagtagcaat gccggtcatc aaacgcggga acaagtacca ggccagtgtg ggctctggta    4260
ctgatcgctg gcgcaagatg ttcgacaccc aggaggaggc ggagaccgca gaactggcag    4320
agaagctgcg caggaaggcc gctgggaagg acgagaaggg ggctacaagc tccgcaaatg    4380
gggcgaaggt acagaagacc ctaaaggagg cttacgaccg caccttggcc ctgatttgga    4440
agggcaccgc tgcggagaag acccacatca tcaactcgaa ctccgtgatg gcggagttgg    4500
gcaaggacac gctcctgtcc gacatcgcca ccgaggacgt aacggagatg atcctggctc    4560
tggaggagaa gggcaactca ggcagcacgg tgaacaagaa gctgtcctgc ctgtccatga    4620
tcctcaagac cgcctcggat gagtggcctg ggtgcatcgt ggagatgccc aagctgaagc    4680
ggcgcaagga ggggtctcac cggctccggt ggatcaacga ggccgaggag aagcggatgc    4740
tggaggccgc ggagcacctg gggctctacg acctccggga ctacatcatc gttggcatcg    4800
acaccgggtt ccgccgcgga gaactcctcg ggttcccccct gaaggactac cagggcggtc    4860
tcatgatcct ccacgatggt gagaccaaga gcggcaaggg gcgcgccatc ccggtcacca    4920
agcgggtcca cgagatcatc cagcggagga gcaactactc gtacctcttc caggactaca    4980
cggtccacaa gctgcgttgg cagttcgacc aactgaagct ccacatgggg ctccaggagg    5040
acacgcagtt cgtggtccac accctgcggc acacctgtgc cagccggatg gttcaacgtg    5100
gggtgcccct gaaggtggtc caggagtgga tgggtcacgc caccatcgcc acgaccatgc    5160
gctacgcgaa gctagctccg agcagcctgc tgatggcgaa gaaggccctg gaggaagaac    5220
cccaggaact cacattcatt cctcccccgc agatggatgt ggtggggctt cacgacttct    5280
aaggaaagga attggaacac ctcagagaga cgttcaaggg aaaggtacag agacaggcag    5340
gacgagatgg gtgctgggtt tggcaaggct ctaagacgga caggggatat gggaaccctgt   5400 gggacccaaa aaccaagaag cctgtctcag cacatcgact gtcctaccaa ctccacaagg    5460
gacaaatccc ggaggggttg atggttctcc accggtgcga taacagggct tgtgtgaacc    5520
caaagcacct gtttgtgggg accgcccagg acaatacggt tgacatgtac ctgaagggta    5580
gaggaacagt tccgcattag gttccacata aggataaccc tgaagggaaa cctaatgtgt    5640
aaatcctaag tgtttatctt catagataga cactattaat gatatctact tagagagaac    5700
actttagttg acactatgac tacccaacaa gtggacaacg agaacgaaga cctggtgact    5760
attcagcttc gtctcgaaga agagatgacc cagcggggag cagaccggta catccggggg    5820
```

```
gtatccaagg ccatcgagaa gggccgtgag gatgacaccg cctacggcaa gcaaatcctg    5880
gccgggaggt tggcgaagct ggcccaggcc atcgctgagt ggaaggcgga ggtggcctct    5940
ggtaagcctg gccggaagca ctcggcctgg aagctcatca aggacacgga cgacaacatc    6000
ctcgccttcc tggccctcaa gcacgttctc tcggggtct ccgcagtccg caccgtccag    6060
tacgtggccg tggccatcgg caccgcggtg gaggacgaga tgcggttcgc caaggtccgt    6120
gaggcggagc ggaagaagtt tgagcagcta gtcaccgggg cagcgaagcg gaccagccag    6180
cactacaagc acgtctacgc cacccgcgtg gctgaggacg tgacggagtg ggacaagtgg    6240
tcccggactc accgcctcca cgtggggtc aagctcctgg acctcctgat gcagtccatc    6300
ggcctggtgg aggtgtccac gaacctggac aacagcgagc aggggctcaa gtacgtgaag    6360
gccctcccgg agaccctgga gtggatcgaa cggaagaacg aggtgaccgc cctgctgcgc    6420
ccggtctatg agccgatggt ggttcagccg cgggattgga ccaacccgtt cgatggcggc    6480
tacctgtcct cgaacatcaa gccgctgaag ctggtgaaga cgaagaacaa ggcgtacctg    6540
gaggaactcc gcggcgctga catgcccatc gtctacgagg cagtgaacgc catccagcgc    6600
acggcctggc agatcaactc ccaggttctc acggtgatgc ggcacctgtg ggactcaggc    6660
tccgagcttg gtggtcttcc ccctcgggag ggactgccga tgccaccgaa gccctacgac    6720
atcgacacca acgatgactc gaagaaggcg taccgcatcg ccgcagcgaa ggtccacatg    6780
gagaacctct ccattctggg ccagcgcatc ggctttgaca tggccctggg cattgcgggc    6840
cgctacgaga gtaccggcg catctacttc ccgtaccagt tggacttccg ggggcgcatc    6900
tacgcggtcc cgcacctgaa cccgcagggg tccgactacc agaaggctct cctcagattc    6960
gccaacggga aaccgctggg ctccgagggg tggaagtggt tggccatcca cggtgcgaac    7020
ctggcgggct atgacaaggt gagtttggag gaccgcgtgg agtgggtcct ggagaacgaa    7080
gatgagattc tcagaatcgc aagtgatccc tacgaccatc gtggttgggc atcggaagtg    7140 ggggggggtta agatcgacaa gccctggcag tttcttgcct tctgctttga gtgggctggg    7200
ttcgttgagc atggtgagtc gttcgtatca aagctgcccg tggctatgga cggttcatgc    7260
tctggcatcc agcacttcag cgcgatgctc cgggacgaac gaggcggggc cgcagtcaac    7320
ctcgtacccc aggacctccc agccgatgtc tatagagccg tcgctgagag agtcattgaa    7380
caggctgaaa gtgatctcgc tcacggttcc gaggacgaac tgaagcacaa cggccggggc    7440
atcgcttacc tgtctgaggg ctccaagacc atcgcccagc agtggatcaa gttcggcatc    7500
acccgcaagg tcaccaagcg gagcgtgatg acgctggcct acggctccaa ggagtacggc    7560
ttcaaggagc aactcatgga ggacatcctg tggccagcga gagggcagc gatgcggcct    7620 gatgggtcca tcgacacgga gaagttcccg ttcagcgggg atggctaccg tgcggctctc    7680
tggatggcga aggcaatctg gaacgcggtg aacgcagtgc tggtgaaagc tggcgaggcg    7740
atgcgctggc tccaggaggt ggcagcactg gccgcgaagg aggaactgcc tgtccgctgg    7800
acaaccccgg tggggttccc ggtgatgcag gcgtatccgg ccctggaggc acgtagggtg    7860
aagaccgcca tcaacggcat ggtgctgaag ctcctcatga accaggagaa ggactccctg    7920
gacaagcgga agcaggggca gggcatctcg cccaacttcg tccactcctg cgatgcggcg    7980
cacctgatgc tcacggtggt ccgcgcgaag caggaaggta tccagaactt cgccatgatc    8040
cacgactcct tcgggaccac cgcggtgac gtggaggaga tgtatcgggt ggtccgcggg    8100
agcttcgtgg agatgtactc cgaggtgcgc gtcctggaag acttccggga tgagatcgcg    8160
```

```
gagcaacttt ccgagaaggc caagcgaag atgccgccgc tacccgagcg cggtctcctg    8220
gagttgtctc gcgtctgcga gagccgctat tgctttgcct gaaccttcc acatctggaa    8280
gagttgagcc gggggaacga ttaggtgcca cacatggata aaccagccgc cgttcccccg    8340
gtggcctctc ccgagacaac cgatggaacg caacgaacac gaagtatcgg accagtacga    8400
gtccgcactt ggccgcgcga ttgctcagtg gcgcaccgga cggcccatcc cgatgacact    8460
cgccgctgaa ctgatgcaac agggctatga cgtatccgcc ctggaagcgc gtcacatgac    8520
ctgaaccaac aatggcagaa aagaaacaac gcaacccgag cttcacctcg ccgcgcggca    8580
tcgcccgcta cccggccctc aacaagcccg actacggcaa cgaacagttc ccgaagccgg    8640
atggtgagta caaggtccaa ctcatcctga gcgaggccga ggcccagccg ctcatcgaga    8700
agctccagcc gctctatgac gcggccatcg aggaaggcaa ggcgaagttc aaggaactga    8760
aggtggagca gcgcaagaag ctgggcgcgc tgaaggagaa tgacctctac gccaccgagt    8820
acgaccagga gaccgaggag ccgaccggca acctcatctt caagttcacg atgcaggccg    8880
gcggcaagaa caagaagggt gagccgtggt ctcgcaagcc cgcgctgttc gacgcgaagg    8940
gcaagccgct gccgaagaat gcaccggcca tctgggcgg ttcggaagtc aaggtctcgt    9000
tcgaggccgc tccgtacttc atccccggca cgggtgctgc tggtctgaag ctgcgtctcc    9060
aggcagcgca ggtgctcgaa ctggtgactg gtggccagcg cagtgccgat gcctacggct    9120
tcggtgccga agacggctac gaggcagacg acaacaatga gagggcgat gaagcccgg    9180
acactgatgg caagagcggc agcggcgaag acgaattcta aatcactgac tgccaaacag    9240
gtggccctga agtacggctt caggagcggc ctggaagaga gatcgccgc ggacctcacc    9300
tcgaaagggg cggggttcac gtatgaggag ctaaccatcc cttacgtgaa gcccgcgaag    9360
ccctcaaagt acacaccgga cttcgaccctt ctcaagaacg gcatcatcgt ggagtccaag    9420
gggcggttcc taacagagga ccgggccaag cacctgctgg tgaaagccca gcacccagac    9480
ctggacattc gtttcgtttt ctcgaattca aaggcaaaga tcaacaagcg aagcccgacc    9540
acctatgcga tgtggtgcga gaaaaacggc ttcgcatatg cggacaagag cgtgcccgag    9600
gcatggctca aagagccgcc gaacctgaag tccctagcag ccatcgagag gctgcgggga    9660
gcatgacatg gcatacactt ccaacaccaa gaagcgggca agcacggact acctggtggt    9720
ccattgctcc gcaacgaagc cctccgctga catcggagcc gcggacatcg accgctggca    9780
ccggaagcag gggtggcgct gcatcggcta ccacttcgtc atccgccgtg atggcaccat    9840
cgaagaaggc cgttacgctg acgttatcgg cgcacacgta gaaggccaca cgagaactc    9900
cctgggcatc tgcctggcgg gtggtgtctc cgagaaggat gtgaacgttg ccgagaacaa    9960
cttcacgccc gagcagttcg ccagcttaca gaagctcctg acggacctcc gagcgaagta   10020
tcccaaggcc accatccagg gtcaccgcga tttccctggt gtggcgaagt cgtgcccctc   10080
cttcagtgcg aaggattggg ccaagcaaaa cggtttctga cacaccacga ggagcaacca   10140
tgaaggcatg gcgtaaagaa cccaatcagg gcgcagtccg tattggtcgc aagaccatca   10200
acgcgaagcg tgtgatgaac aagttcaaac cgagcatggt caaccatggc tccgtcctgt   10260
ttcagcggat gatgctccag gccggtatct gggcgctcta acctaaacca tctccagtgg   10320
tacttcgggc cggtccttcg ggctggcccc ccttttatgc tcaagatttg taagaggtgc   10380
ggtgaatgca agccgtttag cgactttcac aaagcacccg caggaaaatt caagctccag   10440
tcatattgca agcagtgcaa gaaggaatac acgcgggaca ctggagctaa catcctaccc   10500
tccattcgtc agagagcacg aaagcaggga gtcccttct cgcttaccaa agagaacccc   10560
```

| | | | | | |
|---|---|---|---|---|---|
| ccacccatcc | ccgaagtgtg | cccggtctta | gggattcccc | ttcgacggac | actcggcttt | 10620
| gcggacgaca | actcgccatc | gctggatcga | ttgatccctg | agcttgggta | cgtgcctggg | 10680
| aatgttgagt | ggatgagcta | ccgagctaat | cgaatcaaga | acgactcaac | ctatgaagaa | 10740
| ctcgaaaggg | tcactgcctg | ggtccgagag | cgagtttcta | cgacacatcc | catgtgaggg | 10800
| ctgcggttcc | tcagacggga | acagtctctt | cagtgatggg | caccagtggt | gcttcgtctg | 10860
| tgaaacctac | gtgcccggtg | atggcagcga | accaacaata | ggaacaacga | agaagcggat | 10920
| ggaagggctg | ctaaccgggg | agtttcgccc | cctactgaaa | cggaagatca | ccgaggagac | 10980
| ggcgcgcaag | ttctcgtatc | aagtcggtga | gttcaaggga | aagacggtgc | aactcgcgcc | 11040
| gtactttgac | aatgcaggtg | tgatggtggc | tcagaaggtc | cgattcccgg | acaaggagtt | 11100
| caccgtagtt | ggggatggca | aggccatctc | tggaatcctc | tttggccaga | acctatgggc | 11160
| tcctggcggg | aagaagatcg | tggtcaccga | aggcgagatc | gatgccatgt | cggtgagcca | 11220
| agcgcagggc | aacaaatggc | ctgtggtctc | cgtaccaaac | ggagcacaag | gcgcgaagaa | 11280
| gtcgcttcag | aaggcactcg | aatacctgga | gagctttgat | gaagtgattt | tgatgttcga | 11340
| ttccgatgat | gcaggcaaga | aggccgctgc | tgagtgcgcg | gagttgttct | cgcccggcaa | 11400
| gtgcaagatc | gcgtccatcc | cgatgaagga | cgccaacgaa | ttgctgaagg | ctggccgtga | 11460
| gcaggagatc | atcactgcaa | tctggcaggc | caaggagtac | cgccccgatg | catcatctc | 11520
| gggagcggaa | ctgtgggagg | cggtgtcagc | atctcaggat | atcgtagagt | ccgttccgta | 11580
| ccctgggac | gcactgaatg | aagtcacgaa | aggcgcgcgt | acaggcgagc | ttgtgactct | 11640
| cactgcgggt | tccggcatcg | gcaaatctgc | cgtggtacgc | gagatcgctc | accacctcct | 11700
| gaggcgtgga | gagacggttg | gcatgttgat | gctcgaagag | aacccgaagc | gcaccgcgct | 11760
| gggtctcatt | agcatctccc | tcaacaggcc | tctccacata | gaccgtgaag | gtgtcagcaa | 11820
| ggatcaactg | aaggtagctt | tcgatgatac | ggtaggctct | ggccgactat | tcctctacga | 11880
| ccacttcggc | tccagcgaca | tcgacaacct | ggtgtcccgt | gtccgcttca | tggcgaaggg | 11940
| cctggggtgc | aagtgggtca | tcctcgacca | cctgagcatt | gttgtctctg | gcctcggtga | 12000
| cggagacgaa | cggcgactca | tcgacaacgc | aatgacgatg | ctgcgtaccc | tcgtggagga | 12060
| gaccggcatc | ggcatgttgg | tggtgtcaca | cctccgccga | ccggagggtg | accgcggcca | 12120
| cgaacaggga | gcacgtacct | cgctcaccca | actccgcggt | tcccatagca | tcgcgcaact | 12180
| gtcggacatg | gtgattggtc | tcgaacggaa | ccagcagggt | gagaacccga | acgtcaccac | 12240
| gctccgtgtg | ctgaagaacc | gcttctccgg | tgagaccggt | gaggccgggt | tcctgctgta | 12300
| cgaccgggag | accggacgcc | tggaagagac | ggacgcacct | gctgcgccct | tcaaagacga | 12360
| aaccaaatcg | gacgttcagt | ccgagttcta | accaaaggtt | acatcatgag | tctgatttcg | 12420
| ctgttcacgc | agtccgctgc | tgaccaacgt | gctgccgcgc | ccgtgctgc | ccgtgtccgc | 12480
| gccaagatcg | cggacctgat | cgactaagcg | ggagtctctg | tgatcgatga | cacccgcctc | 12540
| caagagttcc | gagaaatcct | cgatgtagtc | cgctgggagt | tccccggttc | acacccgtg | 12600
| attgggggcg | gggctctccg | cgattcctac | catggtcgcc | caatcaagga | cgtggacgtg | 12660
| ttcatgcgca | ggcgtgacca | cgagacgctg | aactcggaac | tcacccgctt | catccgcccg | 12720
| ccgatcctcg | tggcccacgg | ctatggccgt | cccgacatgc | acggcgcatg | ggacctgatg | 12780
| cagtccgttg | ctggctacga | ggtgcaactc | atcctcgcgg | acttcgagaa | cctgaaagac | 12840
| ctggccggta | cgttcgacct | ggggattgcc | cgagccacct | tcgatggtga | ccggctgttc | 12900

```
ctccatccgg acttcctcca ggactccacg gataaggtct tccgcatccg tcgcgcggac   12960
aacctgttcg agaaggcgcg aagcctgaag cgcatcaagc ggctggcaga gaagtacccg   13020
gacttttcaa caccggactt cgagcattgc cctgtctgcg cacaacccat catcgagttc   13080
cgcaacgctg ccagcgtccg agagcaccaa atctccgggc tctgccagca atgccagtac   13140
ttggtgttcg acaaggactg accatgaaca ccttcctcat tctcctggtc ctcatcggag   13200
gccaaatcga aggccgcgtg atcgctgagt tcgacactcc ccgtgagtgc gaagcagcga   13260
aggaacacgt gagggtcatc aaccaacccc ctgtcgtcgc gtccacgttg gtgtgcgcaa   13320
gggatggccg cgcgtaatca ccaaggacgg tatgaagcta ttcgacattg aaacaaacgg   13380
tctgctggat accgtcacca aggttcactg tctcgtcatc aaggatcgca ccaccgggag   13440
gaagttccgc tgcatccccg caggcttccc gatgcaagcg acatgaccca tcgagcaagg   13500
gctggagctt ctcaagtccg gccccatcgg tggccacgga atcctcaggt acgacatccc   13560
ggtcctggag aagctgtacc cggacttcac ctacgacaag gaccaggtgt tcgacaccct   13620
ggtggccgcg cgtctcatct ggacgcacat caaggacatc gacaacgggc tcctcaaaaa   13680
gaagcaaatc cccggctccc tctacggctc ccactcgctg gaagcctggg gttaccgcct   13740
gaagctccag aagggcgagt acgcggctga gttcaaggcg cgcgtggggg acgcttacga   13800 gggggcatg gagtggcgag agctttctcc tgagatgctc gactactgcg acctggacgt   13860
ggatgtcacg gacgcactgt tcgaccggat cgaaggcaag aactactccg cggaggcgct   13920
ggagcttgag caccgcatcg cctggctgat ggctcaacag gaacgcaatg ggttcccgtt   13980
tgacgtgacg aaggccagcg cgttgtacgc caagctcgcg caacgccggg gcgaactgga   14040
gcgagaactg aaagagttct tccgtttctg gttcgctccg gctggaacag tgactccgaa   14100
ggttggaaac aaggcgcgag gaactgtagc cggtgtcccg tacaccaagg tgaagatcgt   14160
ggagttcaac cccggctccc gcgaccacat cgctaatcgc cttgtcacgc tctacggctg   14220
gaaaccggag gtgttcaccg atggcggtaa gcctcgggtt gatgaagatg tgatggcacg   14280
cctggactac ccgcccacga aactcctcac ggaatacctg ctggtctcca agagaatctc   14340
tcagctagct gaaggtgacc aagcgtggct caaggttgta cgtgacggaa agattcatgg   14400
ctccgtgaat ccgaatggcg cggttacagg aagatgcacg cacgctttcc cgaacgtggc   14460
ccaggtgcca gccgtaggtt cccccctatgg tgaggagtgc cggggattgt tcggggcacc   14520
taagggttgg ctgctggttg ctccgatgc ttccggggttg gagcttcgct gtctagccca   14580
cttcatggcc aggcacgatg gcggcaagta tggaaaggtg atccttgagg gagacatcca   14640
cacggagaat cagaaggccg ctggactgcc cacacgaaac aacgcgaaga ccttcatcta   14700
cgcgttcctc tacggagccg gggacgccaa gattggtaag atcgttggta aggacgctgc   14760
tgaaggaaag aagctcaagg ccgcgttcct gaagaagacc cccgcactca gaagctcct   14820 cgaagctgtc cgtgagtctg ccaagcgcgg ctacctggtt ggcctcgaca gcggcaact   14880 ccatgtccgc tctcagcacg ccgcattgaa cacccctgctg caatccgcag gtgccctcat   14940
ctgcaagtat tgggttgtcc gcacggcaga gcgaatggaa gctctgggct acaagcacgg   15000
atgggatggg gacttcgcgt tcgtcgccta tatccacgat gagcagcagg ttgcagtacg   15060
aaatgaggaa gtcgccaagg tcctcgttga gcaggttgca ttggccatga aggacgccga   15120
agcgtgggcc ggattccggt gcccgctggc ctgtgagtcc aaggtcggta cggattgggc   15180
ttcaacacac taaagtaatc agacaccaac atgagcatgt tccagacgga cctactcaaa   15240
gaagtcctct acgaggcgtt caagactccc ttcaagctcc agtccgactt cgcccgagag   15300
```

```
ttcgctcagg aagtcgccgc tctggcctcg atgggataca tctcgaccta cgagggccg   15360
cagcagttcg gcaagaagtg gcgcgtcacc ggcatcggcc tggacaagct gcgcaagctg   15420
gggatgctgt gagtgaagcc ctacgccccc attcgctgag gatcatgggc cggaagttcc   15480
gggtctctta caaggatgac ctggacggtg acctgggata ctgcgaaccc accaagtgta   15540
agatcgagat tgagaacggg cagcaccccg tggaggaggc cgatacggtc ctccatgagg   15600
tgcttcacgc ggtgttctat ctgatggaca ttgggctctc cgcggaggag gaggagcacg   15660
tggtccgtaa ggttgtcacc ggactcaccc aggtattcca ggacaacccc cggctcctga   15720
cctacttggc aaacgccaag tgatggacca tatagcaag tttgattctc tccaggagga   15780
actcatgacg gacaagaagt ggaccatcac ggttaacgtg gacaccccg agggccaccg   15840
ggagcggacc atcgagttcc cccaccggcc caccgaggag gagcttggtc tcaagctggc   15900
gcagttcttc agccggatga acttccgatt caacgaacac ctgaaggagg tgaaggggtg   15960
tgcgctcctg acacctcgga gaccgtatga aagtagcgct gattgatgct gacgttctgg   16020
tcttccaggc ggctgtagtc gctgagaagg caaccgattg ggggacggt gtttggaccc   16080
tccacgcaga cgagggtgac ggagaacgaa tcgttcgcca gtccgtcatc accctccagg   16140
agaagaccgg tgcggataag gtcatcctgg cattctccga tgaggagaac tggcgcaagg   16200
ccatactgcc cacctacaag gccaaccgag cgggttcccg ccagccgatc atccgcgcgc   16260
atctgaagcg gtgggcttcc gacgaatacg agagcttcac ccggccaacc ctcgaagggg   16320
atgacgtgct gggcatcctg gccacccgcg agggcaagcc aggcgagaac ttcatcgtgt   16380
gctccatcga caaggacatg cgaaccatcc ctggcaccca cttcaacttc ggcaagaacg   16440
aagagttcgt ggtgacggag gaggggcag actactggca tctcttccag accctcacgg   16500
gtgacccggt ggatggctac gcaggctgtc ccggcattgg cccggtggcc gcgaagaaga   16560
ttctcgacaa gagcccccacc tggggtgccg tggtctctgc ctacgacaag gcaggcttcg   16620
gtgaagagga agctctcgtg caggcccgag tggcgcgcat ctgccgcgct gaagactacg   16680
acttcaagaa gaaacaagtt cgactgtgga ccccaaagaa atcctgaaag aactggaaca   16740
gcagcaacgc cgcaagttcg agaaaggccc tctcaccggc aaacgcgccg atgtcatcat   16800
catggacgac atccaggaca ccaaggacac caacccgaag gacgccatcg gctccaccaa   16860
gctccccctc gacctcgttc ctgactcgct ctcggtcttc gccgcgctgg cgttcaccga   16920
gggtgccacc aagtacggtg cctacaactg gcgtgtcgct ggtgtccgtg cgtccatcta   16980
caaggccgcc ctggagcgtc acctgaagaa gtggtggaac ggtgagtggg ccgacccgaa   17040
gacgaaggtg ccgcacctgg ccagcgtcat cgcgtgtgct gcgatcatcc tggacgcgga   17100
cctcgcaggc aagttgacgg atgaccgcc tccggcaatc gacctgagtt ccttcatcga   17160
ctcccttgag gagaccgtga agcacctcaa ggaactgcac aaggacaaga ccccgaagca   17220
ctacaccgaa ctcaacgtat gaacccgaag cgaaacactc tgaccggctg gtcatctat   17280
gatgcagagc gggcgactgg ccgaagcacc gcgattgcgc tgagtcttct aggcaaggcc   17340
attgcaaatc caggtgtggc cgtacaaatc cgagaacatc acggtactcg tccggctgac   17400
gagagtctga tgcgcctgat gcgggatatg gtctttcggc tgggcctcaa gggcatgacg   17460
ttcagccaga acctgactgt gacgttcaac cttgggagc ctgtgtgagc cagagccgaa   17520
agggctctct cattgaggcc ctcatcaaca ccgcaatcgg cttcgggatc aacttcacgg   17580
cgaacctcat catcctccca ctgttcggct tcaccagttt gacggtgcag acgaacctgg   17640
```

```
tgattggcgt ggtctacacg ctcatctccg tggtgcggag ttacgtggtt cgccgctggt    17700
tcaacgcaca catcgtccga gccgccaaga aactctcagg ggcctgaagg tctctttagg    17760
ttccacaata ggagaatcaa attggcgaac gacaagtttc cgccgattcc caaagaatta   17820
cttgaggcgc ttgagaagcg gttcccggag acaccactcg aaaatatcgg gtctgtggat    17880
caacttcgat tggctcaggg tgagctacgt gttgtccggt ttctccgagc ccaattcgag    17940
aagcagacca agaacatttt ggagaacaca tagtgtgcat gtctcaaccg tccgccccac    18000
ctccggcccc accgccaccg ccacctccgc ccccgcccgt tgatccgatt ccggtccaac    18060
ctgcgcagca aaccggtgga gcggtgacca gcggcaagag caagggacgc gactccctcc    18120
gtatcgacct ggcccagaag acatcgggtg gtggcgccgg tctgaacatc ccgatgtaac    18180
gaagggcagg gatggaacaa gaaaagaaaa cctgcgcctc cctctaccag aaactcacca    18240
ccgaccgaga cccgttcctg aagcgggcct acgactgcgc cgaactgacg attccctcct    18300
tgcttcctcg tgagggacac aacggctcca ccaaactcgt cactccgtgg cagggcattg    18360
gtgctcgtgg ggtgaacaac ctcgcatcca aactcctgct gacgcagctt cctcccggaa    18420
ctcctccgtt caagttgtcg attgacgact tcacgctgga ggaactgacg aagcaggaag    18480
ggatgcgggc gaaggtagag gaggggctca acaagatcga acgcgcggtt cagactgaga    18540
tcgaagcgaa ctacatccgc gtggctgcct tcgaggcgct gaagcatctc atcgttagtg    18600
gcaatgccct gctgtacatt ccgcctgaag gtggactgag agtattccac ctggaccgct    18660
acgttgtccg ccgtgacccg atgggcaacg tgctggacat catcaccaag gagaacgtct    18720
cccgagacgc actccccgac aacctcgtcc tccctgatga caccgaggag aaccaggagc    18780
ccgcggctgg tacgaaggat gtggagcttt acacccacgt ctatcgccag ggccgcaggt    18840
ggaaggtcta ccaggaagtc aagggtgtcc gcattcccgg caccgagggt tcgtacccgc    18900
tcgataagag cccgtggatt cccgttcgct tcacgcagat cgacggtgag agctacggac    18960
gcggttacgt ggaggagtac atcggggacc tgaagagtct cgaaggactc tcccaggcca    19020
tcgttgaggg ctccgctgcc gcagcgaaga tcctgttcct ggtgaacccg aatggcacca    19080
cggacatggc tgacgtgtcc gaggctgaga acggtgcgtt ccgcgagggt gtcgcaactg    19140
acatcacggt cctccagctt cagaagcaca atgacttccg cgttgctctg agaccatga    19200 aggacatcac cgagcgcctg gcgtttgcat tcctgctgaa ctccgcagtg cagcgcaacg    19260
gcgaacgggt gaccgcagaa gaagtccgct acatggcgaa cgagttggag tctgcgctgg    19320
gtggtatcta ctccatcctc tcgcaagagt tccaactgcc gctcatcaag cggatcatgt    19380
accagatgga acggcagaag cgtctgcccg tccttcccga agggaccgtc aagccaatca    19440
tcgtgactgg catcgaggcc ctcggacgtg gaaacgacct gaacaagctg atccagttcg    19500
tccagatcgc cgcacaggca gcgaatcttc ctcccgagat cgacaaggcc gacttcctca    19560
agcgtgctgg tacggcgctg gggatcgaca tgaagggtct cgtgttgccg cctgaggtgg    19620
tagctcagaa caaccagcag gccatgatga tgcagatgat gcagcagggt gtgaaccccg    19680
ccatcacgca ggctggacag ctaatgaaac aaggaatgca gaatgccgcg caacccgcag    19740
gcgggcagta aggctcccga ggccaacact gccgaagccc ccgtggtcac cgttgaagac    19800
tcggtggccg aacagcaacc caagcccgca gcgaagccgg tcaaagtgac cgaactacct    19860
ggtggcgtga agatcgaaga cttctgatga gtgtggattc cgtagtcatc aagcagccgg    19920 acgtccggt ggaagaccag gcccacatcg atgcgatggt ggccaaggtg gatgctgcca    19980
atacttcgac cgaaccggac actcccgagg tgcccgcaga gggacgcccg cagtggctcc    20040
```

```
cggagaagtt caagtctccc gaggacttgg ccaaggcata tgccgaactg gaaggcaagc    20100
tgggtgggaa gaaggatgat gccactccac ccgctgacga caaggccgcg aagtctgacg    20160
aaacccggga cccaagcaag gccacccagg acgatgcctc gaaggctctc tctgagaagg    20220
gcctgagctt cgatgagttc tccgctgagt ttgcccagaa gggtgaactg accgccgaga    20280
gctacgagaa gctggagaag gctggcatcc cgaaggccgt ggtggaccag tacatcgctg    20340
gccagcaggc cctcgctgag tcgtaccgca aggacgtgac ctcggttgcc ggtggcgatg    20400
aaagcttcgc tgagatggtc acatgggccg ctgcgaacct ctcgaaggaa gagatcgccg    20460
cgtacaacaa ggccgtggac tccggtgaca tcaaccaggc gaagctggtc gtggccggtg    20520
tgtaccagaa gttcgacgct gctggccgcg gtggtgagcc tgccctggtg actggcgctg    20580
gcggtaaggt ctcgggcgat gtctatgagt ccctggctca gatgcagaag gacatggcct    20640
cgccggagta caagaccgac cccgcattcc gcaagaaggt ggagcagaag atcgcccgct    20700
cgaacatctt gtaaggaacc atcatgatcc tgggagcat cctgggttcg gtggtggtcc    20760
ccgctatcat cgacctcgtg aagggtgctg gtggggccat tagccgcaag ttctttggtc    20820
tgtcggttga cgaccagatc aagattcaaa atgccgacat cgagaagctc aaggctctcg    20880
ctgccctcga caatccgtat ggcaccccca gccagtgggt ggtggacctc cgcgcatcgt    20940
tccgatacat cggcgctgcc gcggtcatcg ctgtcggctg tgtcaccctg tatgccggtg    21000
tccagaccaa catcgaagac gtgaaggaga tgggtttcgc cctcgtgggc atgcccttcg    21060
gtttcatctt cggtgaacgc ctgtacctcg gcctgagggg caagagcaag taagcactgc    21120
cgggaagcag cgcattctgt acggttctga tcccgtaacc gttacccacg ggatcacact    21180
gccattgaag tgaaaggtcc tagccgcact cgctcctgc gcggtggctc tgctgcatcc    21240
aaagaacacc acaacagaac cttggcccgc tgaggcggac aaccctgtgt gacgtgtgag    21300
ttcccggaag ccgctcaaca cgactttcaa ctcacttcca aaacaaaaat ggcaaacgca    21360
gttccgtctc gcctgggcca ggcaaacctg gcaggcgatc cgaaggccct gttcctgaag    21420
gtcttcgctg gcgaagtcat gacgccttc gctgaaaaca acatcgtact tcagtacgtc    21480
cgccagcgca cgattagttc tggcaagtcg gcttgaccca accttatgaa ctgggccgac    21540
tctaaacacc ccgtaaattc ggtggaaccc catgggggca ataccgagcc aagacttcgc    21600
agtacgcgag atggtgtaga gactagacac ggggaaccca caaagacctg cgcatgttgc    21660
aacgtcgaga agcccgcccg tgagttctat aaaaaggacg cacagacagg aaggctcgat    21720
ggaatttgca agtcctgccg aatcatcaag acccgagaga aaaccttagg ggtcactgaa    21780
gatgactatc ggcggatgta tcatgtccag ggcggtcgat gtggaatctg ccaacggcgc    21840
ttgtactcaa agaggtacaa gagttttgca gtggaccatg atcacgagac aggaaaagtc    21900
cgtggcttgt tgtgccataa ttgcaaccgc ggattaggca tgttccgaga cgacccgact    21960
gcgcttaggc gtgctatcga ctgggttaag gtatagtccg atcctcacag caatgtgagt    22020
aggggaagca gttccccgta attggtaagg ctaccgccgc gtaccacacg cccggtaacg    22080
aaatcaacgg cagcaacatc gcccacaacg aagtggtcat caccatcgat gacctgctgc    22140
tggccaacac cttcatcgcc aacatcgatg aagcgatgaa ccactacgat gttcgttcgg    22200
tctattcgag cgaactcggc aaggccctgg ccaaccagct tgaccgccac ctgctgcaac    22260
tggctgtcct ggccgcccgc tctgctgccc gtatcacggg cgaacagggt ggttcggtca    22320
tcaccgatgc tgctgccggt accgactcga acgcactggt cgcggacatc ttctccgcgg    22380
```

```
ctcagaagct cgatgagaag gatgtcccgg ctgatggccg tgtgtgcttc ctgcttccgg   22440
cccaatacta cgccctggca cagaacacca agattctgaa caaggattgg ggtggtgccg   22500
gtgtgtatgc ggatggcaag gtcctccgtg tggccggtgt ggagatcgtg aagacgaacc   22560
acctgccgaa cacgaacatc gcttcgggtt cgaccgcggc tggtactggc gataagtaca   22620
ttggcaactt cacgaccacc gttggtgtgg tcacccagaa gtccgccctg gcaccgtga    22680 agctcatgga cctggcgatg gagtctgaat accagattca gcgtcagggc accctgatgg   22740
tcgccaagta cgcaatgggt cacggcgttc tggctccgca agcggctgtc gaaatcaaga   22800
ccgcataagc gtcccctcaa gcctcgggag gttctcttca agagttcctc ctggggcttt   22860
tttttctgct ctcaaggatc accaattggc aaccaagact caaactgatc gcgccaagga   22920
cggtcaggat ttcttccagc ttccggccca caaggacacg cccgcggtca ccgtgaatgg   22980
caccgcccgt gctcgcacga ctgtcccgag tggcgtccag ctggcaaccc ctgcggctca   23040
ggatgacatc gtagcgatca cgttcaactc ggctgaccct gggaataccc gccgcgaggt   23100
cttcaccccg gccactggcg caaccatcac acccaccgag ttctgcatcg aggcccgcat   23160
tgtaccgcca ggcaccattg cggccctcac catcaccttc cccccgaacc cctcgaagga   23220
aggccagcag ttccgtgctg tcaccacgca gaccatcacc gcggtgaccct ggactggtgg   23280 ctctcgtctc aacgctccca ccacgctagc cgctggccgt gctgccacct tcgagtggag   23340
cgtggcgaag caggagtggg tcttcatcaa ctaaggaaaa cgcatgacca ccatcgtcac   23400
tccgaccacg gagcttgagg cggtcaacct gatgctcgat gtcatcgggg agagcccaat   23460
cagcaccctg gagaacagcg ctgtggtgga cgcggtgaag gccaaggcgg tcctctccga   23520
ggtgtcccgc gctgtacaaa cgaagggctg gcacttcaac accgagaagg ggttcgagct   23580
agttcccacg gtcttcgaga aggagatcat cgtccccgcc aactgcctgc gcattgatac   23640
ggtctacccg gacgagggca tcgatgcagt tcaccgtggc actcgcctct atgaccgccg   23700
caggcacacc taccagttcg acaagagtgt gaaggtggaa atggtggtca acctccaatt   23760
cgaggaactc ccggaatccg cccgccgcta catcgccatc cgtgccgcac gggtcttcca   23820
ggcccgcata gtgggctctg agagcctcta ccagttcacc gcagaggacg agagggacgc   23880
ccgagcggac ctcaagaagg ctgagggcat cacgggggac tacaacattc tgacggacag   23940
ctgggctgtt cgtcgcgtca tcgatcgctg atatgcccct cgtttcttct tccatcgcca   24000
acatggtgaa cggggtctct cagcaaccct tcacgctgcg tctcgcgtct caagctgagt   24060
tgcaggagaa cggcctcagt accgtggctc aggggttgaa gaagaggccc ccaaccaagc   24120
acatcaaacg cctcggcagt gccatcaccg gctctgccta catccacacc atcaaccgtg   24180
actctgtgga gcggtatgag gtggtcatca cgaacggtga cctgaaggtc tacgacacgg   24240
cagggaacca gaagacggtg aacttcccga atgggaaggc gtacctgaac tccacggacc   24300
ctgctacgtc cttcagggcc gtcactgtgg cggactacac gtttatcgtg aacaagaaga   24360
ctgtcaccgc ggccagtgcc acgaactccc caacgcggcc cttcgagtcc ctcgcaaacg   24420
tgaaggttgg gctctactcg aagacctaca ccatcaccgt ctccggtgtg ggcacggcca   24480
cctatagtac ccccgatggc accgttgcgg cccacgcggc acagatcacc acggactaca   24540
tcgccaacca gcttgcgaat ggtctcatta ccctcggtgg attcacctca gtgaaccagg   24600
tgggctccgt catctacatc gcccggccca ccgattacac catctccgca acagatgggt   24660
ataacaacgc ggccctgaac gtgattaagg ggacggtgca gaggtctcg gacctt ccgg     24720 cgaatgcgaa cttccaggac ttcactgtgg agatcgcagg ggacaacacc tcggagtccg   24780
```

```
ataactattg ggtcaagttt gacaagaccg ggaacaactc cggtgtctgg cgcgagacca   24840
tcaagccagg catctcggtt ggtcttagtc ccagcacgat gccgtgggta ctggtccgtg   24900
agtcggacgg cacgttcacc ttcaaaccca tctcctggac gaaccggctg gtgggtgatg   24960
aagactccgc tccacaccca tcgtttgtgg gccgcaccat ccaggatgtg ttcttctacc   25020
ggaaccgcct gggcttcatc gcggatgagg ctgtggtgat gtcggaggct ggccagttct   25080
tcaacttcta cccgaccacg gtgacgcaac tcctggattc cgaccgcatc gacgtatcag   25140
catcccacac gaaagtctcg aacctgaact tcgcggtggc cttcaacaag gacctcctgc   25200
tgttctcctc gcagactcag ttctcggtgg aatcaggtga cctcctgaca cccaagagcg   25260
tctccatcaa gcccaccacg gagttcgagt gcagcaccct tgcgcctccc gttgggattg   25320
gacgcaacgt ctacttcgcg gtccctaagg gtgagttcga gggcttccgt gagttctacg   25380
tagcggacaa cgcaggcacc aatgatgcgg ctgagatcac cggccacgtc ccgaagtaca   25440
tcccgaaggg ggcctacaag atcgctgcgg ctctcaacga ggacttcttc gtggtgctga   25500
cttcagggga acccaacgcg atgtatgcgt acaagttcta ctggaacagc aacgagaagc   25560
tccaaagctc ctggtccaag tggaccttcc cgagcacgga cacgattctc cacgcggagt   25620
tcatccagtc ggaactgttc atcctcatca accggcccga tggtctctac ctggagaagc   25680
tcagtgtggc tctcggggac atcgggacga acgagcccta caacgtccac ctggaccgca   25740
agctgacggt gccgaaagca agcctcacgt atgacggcac gtacaccatc atctcctccg   25800
cggctctccc gtggaaccca acggatgaaa cgtacacggc agtggtggcc accagtcagc   25860
cgcagaaggc tggcgtcctc tacccggtca tttgggatgg gacgaacgcc aagattctcg   25920
gtaaccgtgt ggactccgac ctcatcgttg gtaggcgcta cgccttccgc tatcgcttct   25980
cgccgctact ggtccgccag cagtccggcc agggccagaa ggcggacacg gttgcacgtc   26040
tccagattcg caacatgcaa gtcaacttct cggagagtgg caacttccag gcaaaggtca   26100
cgccttacgg gcgggacacc tacacgtaca cctactcagg aaagaccctc gggctgcctt   26160
cggcaaacat cggggccatc ggaattgaag atggcaagtt ccggttcccg gtgatgtcgc   26220
agaacaccac cgtggacatc gaactcttct cggactcgcc gctccctgc gccttcttga   26280 gtgcagattg ggaaggctac tatgtccgac gaagccaggc ggtctaaacc atacgtccgt   26340
cctgcaacac gcgaagactg catcatcctc gcaaggaacc tccgacagga agacgcggag   26400
gagatcgctc atgtgaacgg tctccccgcg gagatgaatc tcttgctggg gttccgcacc   26460
tccgctcgac tttatgcggt ggtgtggggg gatgagaccg tggccgtgtt cggcatcggg   26520
ggagtgcctg gcgtcatcgg cttcccctgg atgctcgctt cgccctccct ctcgaaaatc   26580
cgcaagagct tcctgaggga gtgccgcggg tacgtgaggg gatgctcca ggagtatcgc   26640 cacctggaga actacgtgtg ggcaaagaac gaagtccaca tccagtggct caagtggctg   26700
gggttcgagt tcgagccagc agcaccattc ggtatcaatg acgaacccct tcacagattt   26760
tataggagca tgtgatgtgc ggaccagccg cagttccaat cgccatgctg ggtatcagcg   26820
ctgtgggcac tgccgcttcg attagcgcgc agtcgcagca gcagaaggca caggatgcct   26880
tcaaccagcg ccagtatgaa aacgacatga ccgcgtaccg aggcaacctc gccaacatcg   26940
aggtgcaacg gaaccaggcg cgggaagatg cagtagcgca gaagcagcag aacgacatgg   27000
caggaaggcg cgcaacagca accgccacga ctgccgcagg tgaggcgggt gtctcaggcg   27060
cctcggtgga tgcactgctg cgggacctcg ctggccaggc tgcctacgac aacaccaacg   27120
```

-continued

```
tggatgagaa ctatctgcgc caggacaggg ctctgaacgc ccagcgtgag aacgccttca    27180
acagcactgc aagccagatc aaccagcttc gcccctcgat gtccccggac tatctcggcg    27240
ctggtctccg cattggccag gctgctgcgg gtgcttacag ccagtaccag cagaacctcg    27300
actacgagcg gaaccagagc gtcccacgcc gaggagcata aatggcacga gttcagacag    27360
actatcgaac ccgaggtaca gggcttcagg acatctcgtc cccaatgctt cagccgcagc    27420
aggcagggtt agacaatggt gccgctgagt ctgccgcacg gctggcccag gcgttggggg    27480
ctgttgacct gtctccgctg gtaaccgcca agcgatacca ggatgtggag gaggcggaga    27540
aggcacgggc ctacgccaac tccctcaccg tggaggagct tgggaagcag atcaaggatg    27600
ggaccctcat ggcgtcccat cgcctgtct tcagggcaac ggtcgaacac atccacggtg     27660
agaacacgct caacacgttc gagcgggaca cactctcgaa gctcacccgc ggggaactga    27720
agttcgacac cccgcaggcc atggatgagt acctcacgaa gtaccgcaac gaggccctca    27780
cgggatccag caagttcacc actgcgggct tcgataaggg ctacggcacg ttccgtgagc    27840
gagccatcgc ggttaacgtg aaggtggccg atgaagaggc cgtgaagcgc ggcagccagg    27900
aagcctcgga caacctcggc aacctgaccc tgcaagtcac cgacccgatg tacaagggtg    27960
acgctgcgca ggccatcgtg gaccgctacc agcttcttcg gaagacctct ctgctgcgtg    28020
acgatgccgc gaaggaagct ctctcggggtg tcgctgcgaa ccttgcagcc tccggcaaca    28080
aggccctcct gggttctctg ctggacaaga agttggacag cggtgtctcc gtcaaggccg    28140 ctctgggga cctgaaggcc atccagttca cgcaacacgc tgaacgtgag tatgaccagg    28200
cgcagcacca acggattgac gttgagattc gtccgttcgt ggagcaggcc gacaagggtg    28260
aactgaagcg ggatgccttc gacaagtggg gggccgcgaa tgagaagtac gtcaccaccc    28320
ccaccatcca cgccatcatc aagggcaacg aagcggccat cgagcggcaa cagaagctca    28380
tcgctcagaa cgcccctcctg gcccaggccg aagcaacaca ggctcaggca acgcaggcag    28440
cccgcacggc catcgaccag ggcaacctgg cgttcctccc gcagcagaag gtgatgacac    28500
ctcaggggga acagaagaac ttcgatacga aggccgctgc tgtcccgtac atccaggaac    28560
ggattgcacg ggagaacatg ccgttcggta agcaggtgga gttctggtcc accaacgggg    28620
tggagaatcc cgagtgggag aaacagatca agggtggcct ctcgaacctc gcctccgcgg    28680
gctggacctt cgatggcaag accattggcc aactgaacaa ccagggccag gccgcaatcg    28740
acaccttcat ccgcatcaac agcaccaacc ccggctacgc tgagaagttg gtgggcggtg    28800
acaaggacta caagaagctc tccgacatcc agttcctcat ggagaagggc ggcttcccga    28860
acgtcaacga tgctgcggca ctcatcaacc agattgaccg cgctgacatc aaggcatcgg    28920
actacggttc gatgaagcag aaggtggcct cctcggtgga cgatgtggtg aaccagcatt    28980
ggtactcagg cgccaccagt tggttcagtg gcctcttcgg caatgaccag gtgaacctca    29040
ccgctgtctc cgctgacatt cgccgcaggg ctgaactcct ggtgatgtct ggccaggtgc    29100
ccgatgcgaa cgccgcggtg aaggccacgg tggaatacct ggcgaacccc gcagtcacca    29160
cgcggatcaa caatacgctc tacttcaaca aggaccttcc ggtggtcccg aagggcgagg    29220
acaccgggca gtgatggggg cggttcatca aggacgttcc ccagcagatc gccaaggcga    29280
acaacctcgg tgatgctcgc ctggagccga accagtacgg aggcttcacg gcctggactg    29340
gtggtgtccc gatgacggac ggcaccggta aggtggtcac ctacacgcgg gatgacatct    29400
cgaagtgggt ggacaacacc atcaccgctg accgccacaa ggccgctgct gatgccaact    29460
tcaagagcta ccaggaccgc ctcgtgaagg aactccgcga tgaaaagcag aaggacccct    29520
```

```
acgtgatgga gcggatgttc gacgcgactg ccaacggcat gtggtggaac cgccaactct    29580
acagccgcga aggctatgag caggttctcc gtgacggcaa cacaggcaag ccgctcaacg    29640
aactgttcca aatctacaaa gacaaacgct tcaaggataa gtaatggccg catcgatcgc    29700
tctggggat gtccagagga ttacctccga gacgagaag aagtacgggc tccctgaagg    29760
gacgctgttc aagatcggaa acatcgagtc ctcgttccag gatggccagg tgagcccgaa    29820
gggagccaag ggctacttcc agttcaccga tgacaccgca aggcgctacg gcctggatga    29880
tccgttcgac ttcgagaagt catccgatgc cgcgggccgg tacatgcgag acaacctggc    29940
caagtaccag ggcaacatgg acctgtccct cgcggactac aacggtggcc cgaaggccgc    30000
taaggctctc gccaaggga agccctgggc agagacttcg gactacctgg cgaagttcta    30060
cggcaacaag tccgagccgc tctcgcagca attcaccacg ggctccgaag tccctcttac    30120
tgcctccccc tccgcctccc agctatatcg agacgcacgg cagcaggagt ctgagtatgg    30180
aggggttggc aataacattc tcaatctgcc tcgtgctatt ggcctgggct ttcaagtcga    30240
taattcggtc tacaatttct ggcaggagcg aggactctcc agcgtagacc ccgacttccg    30300
ctgggacgat gacttctcga agcagatgct tgatggggtc cctgagcgtc attggggata    30360
cctgctgcaa tccaagtcga agcaggaagc ggaactccgc cgtgcccgtc tgttggacac    30420
gatggagaag gaagtcgaac tctccaagat gggtgtggcc ggtttcggtg gtcgcctggt    30480
gggcaacctg gtggatctac ctacgctcat ctcgttcgtc cctgggttcg gtggtgcggg    30540
cctcctcacg accacttcac gcatcgccaa tgctgcccgc atggctgccc tcggtgctgc    30600
tacgaacgta gccttcgatg ctgcaacgat gcagttccgc cccacggcca ccccggatga    30660
cctctacatc tccgctgcga tgggcctggg tctcggtgct gctggtggcc tctcggtgaa    30720
tcctgcccgc ctggccgcgc aacgtctcgc tgctgagaac cgccgcctcg gtgagttcgg    30780
tctccgtgaa tccggcaagg cgcagatcaa ggagcttggc gacaacgct tcaacttcgg    30840
tgctggccgt gaggagttcg cacggcgcat ccaaggcaag cccgatgagc cggtggagat    30900
caagtaccca ggcggtgcaa tcgtgctgcc gcggggcgat ggtgagcctc cgaagatttt    30960
ccaccctggt gatcccctg aggttcgcaa gccaggaac atcaacgagc cgcttcctcc    31020
cgaagctcct ccagctactc ctccggccac cggcccggtt gctcccaagg ctcctccagc    31080
agaggcacct aagggcaagg gctggacctc cgagtggac actccgcggt acgcctcagg    31140
cggtggcaac gagcaactcc tcgtgctgcc tccggcaaag cgtgtgagtc agttggctga    31200
gtatgtccgc cagttctcga agaacgggga catcgtgagg gtgatggacc gggtgctgaa    31260
gggcatcgac ctccgcaagt tggagttcaa ggtcatcgag aagggtcagc gtttcggcca    31320
gcgtgacatg gacaacgaaa tcctcggcgc gaagggcgct gtaggtactc cgcgaggttc    31380
cattggtgac aacatcatga tgttcctgcg gggccactcg tgggagatgc tggtgtcaa    31440
cccgatgcac acgtgggtc tcaacgagga gacgttcgtt cacgaactcg ttcacgttgc    31500
caccgtctac aagctccgcg gtgttgagcc tggcatgggt gtacgcatca cggaccctgt    31560
tgtgcgcagg gctgctgatg acctggccgaa cctccacggg gacatcctcg accacgccag    31620
gcaaaccttc ggggccaact ggaaaggtga actccaggga cgcctcggtg ccaacctgga    31680
gaacgagaag gaactcatcg cctatggtct gacgaaccgg aacttccagg agtggctcaa    31740
gacggtgccc gttgagggtg cccctgagaa gaacctgtgg gaccgcttcg tgcattccct    31800
gcgcaagctc ctgggcatcg gcccgaagga acacaacgcc ttcacccggc tgatcgaact    31860
```

```
gtccgcccct ctcacgaaga agggcgactt cgttgagcgc atcaagacga acccagagtt    31920
ggaagcaacg ggtgggtttg ttgacgctga caccgtgaag gccgcgaacg aagctgacct    31980
ggctccggtc tatggctggg gtctcggcct ggagaacagg ctgggtggtg ctaaggctcc    32040
ccccgctgtt cgtcagttgg cctcgaagct gttcggcacc accatcggct acaaggacaa    32100
cgcggtggtg aagctcaacg cttgggacga caccacgaag tgggctgact cctgggccgt    32160
ggagatgcgc aagggcacct atccgcagtt cgaggagtgg ctcaagggct ctcagtacaa    32220
gtggcacgag aagggcaagg cgttcgatga cttcggcgca caggtgtcca actacatccg    32280
cggcttcgag ggtgattacc caccgcaggt ggtcaaggct ggcgagcaca tgcgcaagac    32340
cctggccaac gtggtggact acatcaacag cccactgaag gacgaaggcc gagccaagat    32400
tggtctcacc gagacggaca tccgagaccc ggagaccggc aaggtggagc gggtagggac    32460
gctggagaag aacccgaact acctcccgcg caagcacgac atcaacaagt ggaactcgat    32520
ggtctccaac ttcggcaggg atgccgtgga agggtggtgg gcacgggcct accaggctgg    32580
ccgtgaggga atctctgacg aggccgctgc gaagtgggcc aagtggtatg tccgcacggt    32640
ggaggaggct cacgccaacc gcactcagga catgctcgat gacctcctga agggcaccga    32700
tagggacgcc ctgaagaact ccctgatgct caacggaggc tactccgaag cggaggctct    32760
gcggatcatg gacgacatga ttcctggtag ggccaccgat gcaggccgca cgatggccag    32820
cctgaagcac cgcaacacca tccgggaaac gcacaccgag cggtggacca cgaaggacga    32880
gacgaagatg gaggtgagtc tgaacgactt catccactcg aacgccttcg acgtggttga    32940
gccgtacctc cgcaggaccg cgggcagtgt ggcgctggcc aagcatctcg acatctacaa    33000
gatgggggac attgaccgcg ttatcgctga ggccaccggc aacaagcttg gcaggagtt    33060 caagtccacc cccgatattc agaagctccg caaggacctg aagttcgcct tcgagcgagt    33120
ccaagggctt cccctggagg agttctccac gctgaacaag agcctggaga tgtggcgcaa    33180
cttcaacgtt atccgcctga tgggtggagc agtctggaac caggccaccg aactcagcca    33240
gatcatcggc acgatggggt ggaagactac gcttgcggct ctccctgagc ttcgagcact    33300
gcgccgtgac atcgccaccg gcaaggcccc gcatgacatc ctggaccacc tggagaacac    33360
cattggtggc gtagggtccg agtacgtggc ccgcctggag ttcaaggctg gtgacgattg    33420
ggtccgcaac aaggggggaca ccaggttcaa ccgctggctg gactctgctg acaccggcac    33480
caggaagctg gcgaaaggtg tgctggatta caccggcatg actccgctga tgattcagca    33540
gaagcgtgtc cacgcgattg cgttggtgaa ccacttcgtc aacgtggcga acggcaaggc    33600
tgctgggttc ctcacgaagg atcgcctggc ctggatgggt atgagcgcgg atgacttcgg    33660
caaggtcctg tctggcatca gcagttcac caagcccgct gatggtgagt tctcgaagac    33720
cttcaagatg gacttcgcgg gctggcagaa ggcggacccg gagagctact cgaagttcat    33780
gacggccatc caccgtgaat cccgcagggt catccaggag aacgacctgg ctccatgat    33840 cccgctcatg ggcaccacgc tggcaagac ggtcttccag ttcatgaact ctcgatgca    33900 cggctggaac aagtcgctga tgttcgccat gaaccaccgc gactggtcca cactgtccac    33960
cgtacttcac ggctcactct tcgcgtccat cgcctacatg gggcggacgc tgctgggtgc    34020
cggtggcatg gaagcggaca agcgccagca gtatctcgac aagcggatgt ccgttggcca    34080
gatcgttacc aacagcttcg ggcgcatctc tcaggcgtcc gtgctgccca acatgttcga    34140
caccatctca ccgtatccgc tgttcagcgg aatgcggacc acgagtgacc tctccagtct    34200
ggcatcgaac ccgacctacc aggccatcaa cggactcatc tcgatgaaga agctgattcg    34260
```

```
gaatggtgtg tcggatgagt accaaaccac ggagaaggac atccgcacct ggggcaggct   34320
actgcctctc aacaacgtct tcccggtgac cacgttcctg aaccacctgg cgaacgatta   34380
tccgcacggc gaaaagcaac aataaacggg tagccctcgg cacgaccggg ggcaacctct   34440
tttggagaat agatagtgcc ttacagttac gttcttctct cggggaacgg ctctgcgacc   34500
aacttcggct tcagcttcgg ttatctcagc aagttccaca tcggagtgaa ggtgaacggt   34560
gtagtcacca ccttcacctg ggtgacggac ttcaccattg gcatcacacc ggccccggcc   34620
aacggtgcag tcatcgaggt tcgacggacg actccgttga atcaacccgc cgtggactgg   34680
tcagatggcc ccacgctcac cgaagcggac atggacctca acactcggtt ctctctgtac   34740
actgctcagg aggccgctga tggtgttgca gcatccatca ctcagaactc cctggggcag   34800
tgggacggcc agaaccgcag ggccgtcaac ttcgcagacc cggttgatcc acaagtactt   34860
cgaggacgtg tacacttcga ggacgtgtac acacctcagt tggacgcgaa ggtcaccgaa   34920
gccaccaacc aggccaacaa cgcggcctcc agcgccgcca ctgcgcaggg ctatgctctc   34980
gctgcggaca actccgcgga cctcgctgcg gccctcctgg cgaccttcaa aggccagtac   35040
ctcggtgccc ttgcatctaa ccccacgctg gacggtaacg gccagccggt gactgctggt   35100
gacctctact tcagcaccac cgataacctg atgaaggtgt acaccgggtc cgcgtggatc   35160
aacgctgggt caaccgtcca gtccaccatc aaacgtcctg tcacacccgt cgtggcaacc   35220
gcaggccaga ccgtgttccc ggtgtctggt gggtacgacg ccccatacat tctcgtgttt   35280
gtgaatgggg ttgaggtggc ttctccagat gtggacgtga ctaacggcag caccatcgta   35340
ttctccagcg gcctgactgc tggagataaa gtggattacg cagcgtttgg tgcgttccag   35400
gtggccaacc cggttatcga tgggaccagc gccgcagact tcatcaagac acgcaatgcc   35460
cgtgtagtta cctctattgc cgacctgaag gccctcaata agaacaccta caacttcgtt   35520
ctcgtcactg gcttctatgc ttcaggggat ggtggcggcg gtttcttcct tcaggttccc   35580
acgatgccca ccaacggtat cgttcaggtc gggaatgacg gaggcatctg gcagttggtg   35640
gttgatcggg attatgtttc cgcgaaacaa ctcggtgcga gactggacgg ttcaacggat   35700
gactcctctc tcctgaacaa cgccaagtcc actctcgatg ctcttggtaa gaggctgtat   35760
atcccgtctg ggggttgcag aatctcaaca gcaatcactc caccaaaggc tggtgtgttt   35820
ggggatagtc ctcaagcgtc catcatccag tgtaacaact gctctgcatt cctattccca   35880
gcaaatttg ggctctctcg tccggcttgt gtcattgaga agttggggat tcagtcctac   35940
agcaacacct gcgatgggct atacgctttc cgtgccctg gggtggcatc tggagcatcg   36000
cccgtctaca acagcggcct aactgttagg gatgttgaga ttggtacggg cggacgattc   36060
ggtggcggtt tctcactgaa ggacttcttc cgagtgaacg tagagaacat tggcatgact   36120
gatgtgagtt ccgccgtatt gctcaccggg tcagttgtgc aggcagtatt ccgaaatgtc   36180
accgcaaacg gtgataacgc accaactgtt cttaaccggt atggtttcca aacagccgca   36240
gcctcctatt ccagcggtac gctaggtcct gaacacatta gtacgtggga ttgcagcttc   36300
attcgctata cacgcggtgt tcaacacgat gctgggctca tggtctcgtt caacaatacg   36360
gacctggaaa cttttcacaca cggcttctat ctctcgcagc cctgcactgt gcgtggtggt   36420
attagcgccc cggctccggc agcttcaggg actgctgcgt ggattgggct tttcaaagct   36480
atttctgatt ttgacgtagc caacggcact ctgatcgatg accttgagat caacacgcta   36540
aacacccccag gaactccagc ctcttcgtat ggggttctca ttggcaacaa tgtgaataag   36600
```

-continued

```
tgcattggta ctacaatccg tagtcccagg attcgaggta acactagttc aatggtcggt    36660
gggattgtcg ctaatctagc tggaggtgac atcgttatcg aggatgccat catcaacggc    36720
agtgtggtta ctggaactac ggtgtctgtg aacaatgctt cctatgcaag ggttgtgggc    36780
aatcgaagcg ccaccggtgg gactgtaaat ggttccctgt caatcacaga taacggtgtt    36840
ggttccattg gtgatgttcg tggaaatgag tttgccacca ttaccaacac cctcaatgcc    36900
tattccggta catggacgcc tggaacaatt cctaacggaa caccagcagc aacaacggtg    36960
gccgtccctg gcgcagtggt tggtgacaaa gtagtggtcg gcctttccag cctgaccgga    37020
tcggccaact gcatcatttc cggctatgtg tcttccaccg gaaatgtggc tgtcctgttg    37080
tataacgtct ctggtgcatc acagacgatt ccctccggga ctctccaggt aacagtcctc    37140
aagtcgtaat caagatgtcc ctctaggttt cccctggagg acttcctct ttcaaggaaa    37200
ggtatgagca atgcgctcaa cgtaagtaag ctggccacac tcacggcaac agaaatcaaa    37260
gcataaccaa acaagaagta atcatgccga acatcgacaa agacgtacag aaggatgctc    37320
tgaaggaggc cctcacggag tggctggaca agcagttcgc cacattcggg aagtgggcct    37380
tgcggtccat cctggccgct gccttctcag tcctcatgta cctgtacctg acttctcaag    37440
gctggcaccg ctgatatgac cgaaaagacc accgcttccg aaaaggagct tggcgaagtc    37500
cacaacgaga tggccgcatg gtgcctggac atcctcaagg gaatcccggt caccgacaaa    37560
gacggtaacc tcgtgattga ggatgggaga gttgctcgtc tccctccggc tcctgcctac    37620
ctcaacgtca ttcgccagtt cctcaaggac aacgacatcc aggctgaacc cgccaagggc    37680
tcctcgatgg gtgacctctc ggacctcccg gtgttcgagg atgacaacgt tgtgcctctc    37740
aagtctcaat cgaaataaac gcgattagag ccctcagag cgattttaag cctccaaggt    37800
agggtagcct atccgggcac ctgatcgcgt cctgtgggc catctcgcaa gccaagaatg    37860
aaaataacaa ctgccgaggt ttcggcaaaa cgctgcccga agtgcggcga agaaaaacac    37920
ctctccgagt tacacgcgaa tcacaccaag agggacggcc acaacaccat ctgcaagctc    37980
tgcatgaagc aggtggcacg agactggcgc aacacacctc cgggccgctc caagcagatg    38040
tggacgacct caaagaaacg tgcggaggag aggggctggg agttcaacct aaccccccgag   38100
tggattcagg aacgcctcga agctggcgtg tgtgaggcca ccgggattcc cttggagatg    38160
tccgcggagg agttcaaagg ctacggccac ttccgtccat ggacccccctc actcgaccga    38220
gacgatccaa cgaaagggta cacaaccgac aacgtgaagg ttgtgtgctg gatgtacaac    38280
caggccaaag gcgtaagcat gcacgaagcc gtcctaagaa tggcccgtgc cctcgtagcg    38340
aatgacaact aaacaacacc cagcacagaa agactttcgc gtctttatgt tcatggtgtg    38400
gcgccacctc aatctccccg aacccacacc agtccaatat gacatcgccc actacttgca    38460
acacggacca cgccgttcag tcatcgaagc gttccgtggt gtaggtaagt cctggatcac    38520
ctccgcctta gtttgctggg ttctgtggaa cgacccacag aagaaaatcc tggtcatctc    38580
cgcctcgaag gaacgagcag atgccttctc taccttcgtg aagcggctca tcaacgagct    38640
tcccgttctc cagcacttga agcctaaggc ggaccagcga gactcgatga tttccttcga    38700
tgttggtccc gcaactcctg accactcccc tcggtcaag tccgttggta tcaacggca    38760
gatcactggt tctcgtgccg acatcatcat cgctgatgac gttgaggttc ccaataactc    38820
cgccacgcag atgatgcgcg acaagctctc tgaggcggtg aaggaaatgg atgcggtcat    38880
caaaccgctc cagacctccc gcatcatcta tctgggcacg cctcagacgg agatgtcgct    38940
gtacaacgct ctccctgagc gtggatacga agcccgcatc tggccagcgc tgtaccccga    39000
```

```
gcttcacctc gtggccaact acaagggccg cctggctcca ttcatcacgc gggctctgga    39060
ggccgataag agtctcgtag gtgctcctac ggacccagg cggttcaacg agactgacct     39120
gttggagcgt aaggcgtcct atggacgtgc tggcttcgct ctccagttca tgctcgacac    39180
gagcctcagc gatggtgacc gctacccgct gaagatcgcg gacctcatcg tccagaacct    39240
caacccacg atggcccatg tgaagatcgc ctgggctgct gcacctgaag tttgcatcaa     39300
cgatctcccc gcggtggccc tcacgggtga ccgctactac cggcccatgt ggacggacca    39360
gcagatgtcc gagtacacgg gctgtgtcat ggccatcgac ccctcgggcc gtggtgctga    39420
cgagaccggc tacgccatca tcaagattct cgcaggcaac ctcttcctgg tggccgcggg    39480
tggactctcc ggtggctact cagatgaaac tctggagacc ctggcgagac tcgctaagac    39540
ccaccaggtg aaccacgtca tcatcgaggc caacttcggt gatggcatgt acaccaagct    39600
catcactcca ttcttcggga aggtgggaca caaggtcctg gtggaggagg tgaagcactc    39660
cacgcagaag gaagcccgta tcatcgacac ccttgagcct gtgctctcga ctcatcgtct    39720
catcgttgac cagaaggtca tcgagaacga cttcaggacg gcagagcagg acatcaagta    39780
cagcctgttc taccagatga cccgatcac ccgagacaag ggtgccctgg ctcatgatga    39840
ccgtctcgat gcactggcca tcgctgttgc ctactggacg gagcatatgt ccagggacaa    39900
cgataaggcc gctgctgcga tcaaggacaa ggcgctgaag gatgaactga agaagttcgt    39960
tcacggtgtc cttgggagca aacccaagcg aacctcgtgg atgtcctcga actcaggctc    40020
caggtgacat tcggtgccac aataggagaa ccctacgtgg gttcttcggg ggcttcatcc    40080
gtagctgata tggatgccac acaccgtgtg gactcgggaa acctcagtgt gtggtgatgt    40140
agtcgctgca ttctaggaca cccgttagtc tccctattcc tcatctctat gggggggtagg 40200
ggggctaact taggtgttcc tagtgttgat gatatagcca ctgagatgtc aacctcagtg    40260
tcccttaagt tgtctcttag ggttgcatta aggagacatc atcaccatca tctcccataa    40320
ggtcatcctc cccatgttca ctctactagt cctcctctca ggtgtccccg tggtgttcct    40380
tctgggtctc gttctgtatg gcctgttgga caactgatgg tgtccctgaa gtgccccctt    40440
aggggggaaaa cttccgacgc aaaaatttga aagcccacct cgaaattcga cgcgggcaga   40500
ttccccccgt gccccccgc ggcccggccc tcgtggcccc tgccgaccca cctccgggca     40560
ccctccaggc tgtacgctcc gctgactcc                                      40589
```